(12) United States Patent
Mack et al.

(10) Patent No.: US 8,748,375 B2
(45) Date of Patent: Jun. 10, 2014

(54) METHODS FOR AFFECTING BODY COMPOSITION USING AMYLIN AGONISTS

(75) Inventors: Christine M. Mack, Camarillo, CA (US); Jonathan David Roth, San Diego, CA (US)

(73) Assignees: Amylin Pharmaceuticals, LLC, San Diego, CA (US); AstraZeneca Pharmaceuticals LP, Wilmington, DE (US)

( * ) Notice: Subject to any disclaimer, the term of this patent is extended or adjusted under 35 U.S.C. 154(b) by 0 days.

(21) Appl. No.: 13/256,779

(22) PCT Filed: Mar. 17, 2010

(86) PCT No.: PCT/US2010/027599
§ 371 (c)(1),
(2), (4) Date: Nov. 1, 2011

(87) PCT Pub. No.: WO2010/107874
PCT Pub. Date: Sep. 23, 2010

(65) Prior Publication Data
US 2012/0053118 A1    Mar. 1, 2012

Related U.S. Application Data

(60) Provisional application No. 61/160,956, filed on Mar. 17, 2009.

(51) Int. Cl.
*A61K 38/00* (2006.01)
*A61K 38/16* (2006.01)

(52) U.S. Cl.
USPC .............................. 514/4.8; 514/5.3; 514/21.3

(58) Field of Classification Search
None
See application file for complete search history.

(56) References Cited

U.S. PATENT DOCUMENTS

| 6,114,304 | A  | * | 9/2000  | Kolterman et al. ............ 424/9.3 |
| 2003/0026812 | A1 |   | 2/2003  | Duft et al. |
| 2004/0022807 | A1 |   | 2/2004  | Duft et al. |
| 2005/0197287 | A1 | * | 9/2005  | Mack et al. ...................... 514/12 |
| 2008/0207512 | A1 | * | 8/2008  | Roth et al. ....................... 514/12 |
| 2008/0274952 | A1 |   | 11/2008 | Soares et al. |

OTHER PUBLICATIONS

Kolterman, 1996, Diabetologia, vol. 39, pp. 492-499.*
Pramlintide. Datasheet [Online]. Convachem Corporation, [retrieved on Jul. 3, 2013]. Retrieved from the Internet:,URL:www.convachem.com/product/151126-32-8.html.*
Mack, 2010, International Journal of Obesity, vol. 34, pp. 385-395.*
Davalintide. Datasheet.*
Nicandro et al., *Clinical Pharmacology & Therapeutics* 85(Suppl. 1):S64-S65 (Feb. 2009): Use of the Continuous Reassessment Method in the First Human Study of the Amylin Mimetic AC2307 [Abstract].

* cited by examiner

*Primary Examiner* — Robert Landsman
*Assistant Examiner* — Ian Dang
(74) *Attorney, Agent, or Firm* — Womble Carlyle Sandridge & Rice LLP; Mark J. Pino; Alireza Behrooz

(57) ABSTRACT

Methods for affecting body composition include the use of amylin agonists, such as pramlintide or davalintide. Total body weight may be reduced, maintained or even increased; however, the body fat is reduced or body fat gain is prevented, while lean body mass is maintained or increased.

3 Claims, 23 Drawing Sheets

*P<0.05 compared to Vehicle - High Fat Diet group

*P<0.05 compared to the Low Fat Diet group unless otherwise noted

*P<0.05 compared to Vehicle - High Fat Diet group

*P<0.05 compared to Vehicle - High Fat Diet group

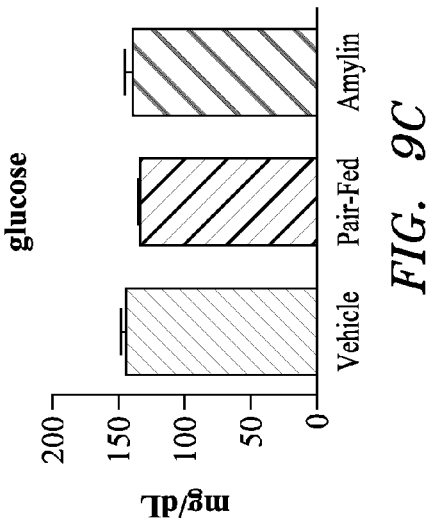
FIG. 9A
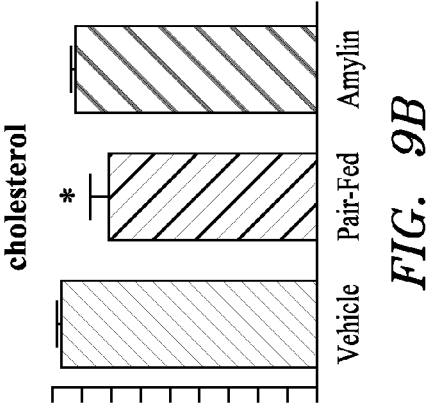
FIG. 9B
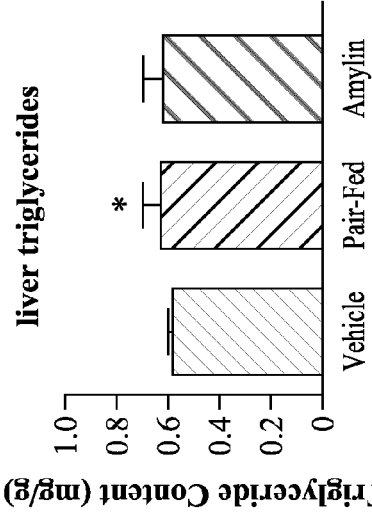
FIG. 9C
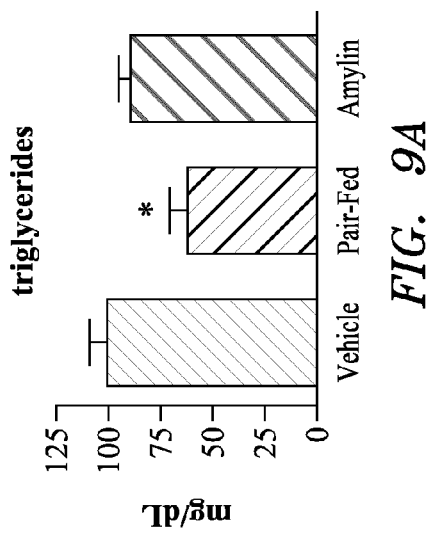
FIG. 9D
FIG. 9E
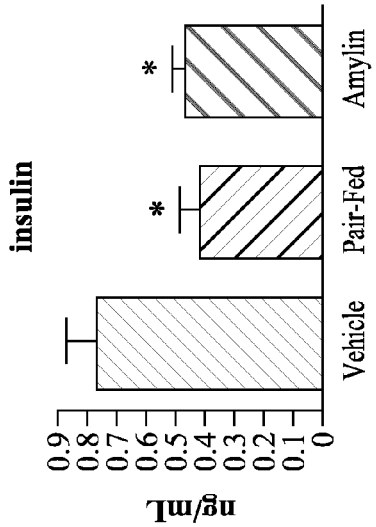
FIG. 9F
*P<0.05, compared to Vehicle

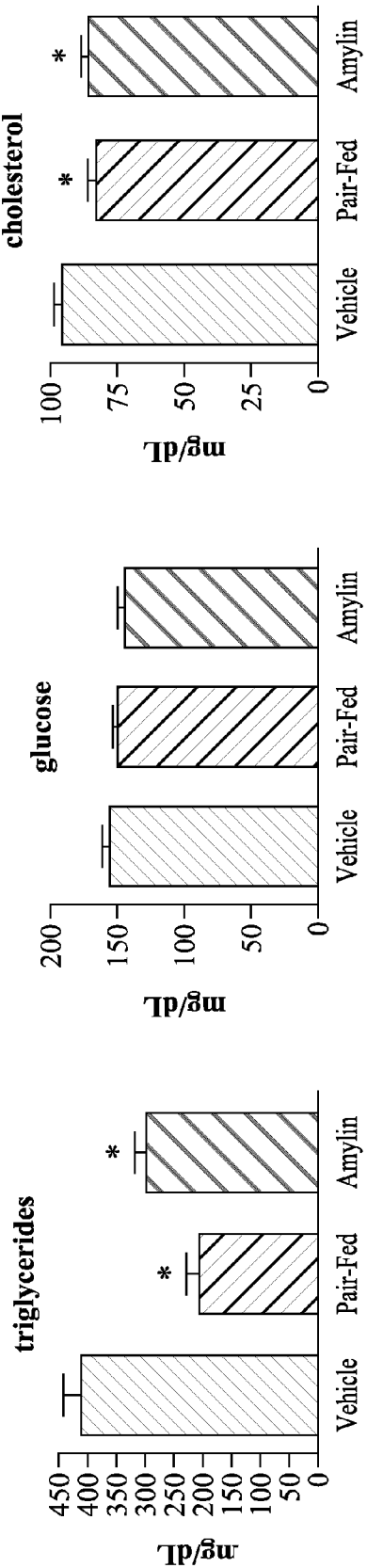
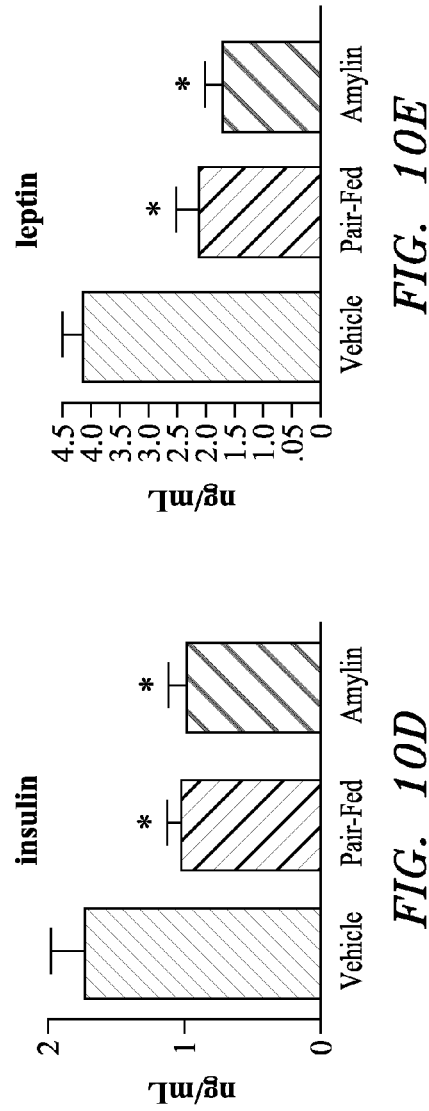
FIG. 10A FIG. 10B FIG. 10C FIG. 10D FIG. 10E
*P<0.05, compared to Vehicle

METHODS FOR AFFECTING BODY COMPOSITION USING AMYLIN AGONISTS

RELATED APPLICATIONS

This is a §371 application of PCT/US2010/027599, with an international filing date of Mar. 17, 2010, which claims benefit of priority from U.S. Ser. No. 61/160,956, filed Mar. 17, 2009, both of which are incorporated by reference in their entirety, including all tables, figures and claims.

FIELD OF THE INVENTION

The present invention relates to the fields of medicine, health and nutrition, and pharmaceutical use of peptides therein

BACKGROUND OF THE INVENTION

It is estimated that about 64% of Americans are overweight or obese (roughly about 97 million adults), and it is generally believed that these numbers are increasing. Obese or being overweight may substantially increase the risk of morbidity from hypertension; dyslipidemia; type 2 diabetes; coronary heart disease; stroke; gallbladder disease; osteoarthritis; sleep apnea and respiratory problems; and endometrial, breast, prostate, and colon cancers. Generally, higher body weights are also associated with increases in all-cause mortality. Furthermore, obesity or being overweight may cause a person to have a negative self-image.

In humans, patients who are overweight or obese are considered those with a Body Mass Index (BMI) of equal or greater than 25. BMI is a common measure expressing the relationship (or ratio) of weight-to-height. It is a mathematical formula in which a person's body weight (kilograms) is divided by the square of the person's height (meters) (i.e., $wt/(ht)^2$). Individuals with a BMI of 25 to 29.9 are considered overweight, while individuals with a BMI of 30 or more are considered obese.

According to the NIH Clinical Guidelines on the Identification, Evaluation, and Treatment of Overweight and Obesity in Adults, all adults (aged 18 years or older) who have a BMI of 25 or more are considered at risk for premature death and disability as a consequence of overweight and obesity. These health risks increase even more as the severity of an individual's obesity increases.

For these reasons, there is an enormous interest in treating obesity. Existing therapies include standard diets and exercise, very low calorie diets, behavioral therapy, pharmacotherapy involving appetite suppressants, thermogenic drugs, food absorption inhibitors, mechanical devices such as jaw wiring, waist cords and balloons, and surgery, such as gastric bypass. Jung and Chong, *Clinical Endocrinology*, 35:11-20 (1991); Bray, *Am. J. Clin. Nutr.*, 55:538 S-544S (1992).

In general, however, while loss of fat is desired, loss of lean body mass (protein) is not desired. Lean body mass is highly active metabolically and physiologically, and the size thereof is generally genetically defined and maintained. Lean body mass contains all the body protein. There is no real protein store as every protein molecule has a role in maintaining homeostasis. It is believed that loss of body protein is deleterious to the health of an individual. The majority of the protein in the lean body mass is in the skeletal muscle mass. Lean body mass is 50-60% muscle mass by weight, and the remainder is bone and tendon. Protein makes up the critical cell structure in muscle, viscera, red cells and connective tissue. Enzymes, which direct metabolism, and antibodies, which maintain immune function, are also proteins. Thus, it is desirable to prevent or minimize loss of lean body mass even while reducing body fat.

[Caloric restriction, regardless of its form, can cause catabolism of body protein and produce negative nitrogen balance. Protein-supplemented diets, therefore, have gained popularity as a means of lessening nitrogen loss during caloric restriction. Protein-sparing modified fasting has been reported to be effective in weight reduction in adolescents. Lee et al. *Clin. Pediatr.*, 31:234-236 (1992). However, these diets may produce only modest nitrogen sparing.

Amylin has been reported to regulate gastric emptying and suppress glucagon secretion and food intake, thus regulating the rate of glucose appearance in the circulation. It appears to complement the actions of insulin, which regulates the rate of glucose disappearance from the circulation and its uptake by peripheral tissues. These actions are supported by experimental findings in rodents and humans, which indicate that amylin complements the effects of insulin in postprandial glucose control by at least three independent mechanisms, all of which affect the rate of glucose appearance. First, amylin suppresses postprandial glucagon secretion. Compared to healthy adults, patients with type 1 diabetes have no circulating amylin and patients with type 2 diabetes have diminished postprandial amylin concentrations. Furthermore, infusion of an amylin specific monoclonal antibody, which bound circulating amylin, again resulted in greatly elevated glucagon concentrations relative to controls. Both of these results point to a physiological role of endogenous amylin in the regulation of postprandial glucagon secretion. Second, amylin slows gastrointestinal motility and gastric emptying. Finally, intrahypothalamic injections of rat amylin were shown to reduce feeding in rats and alter neurotransmitter metabolism in the hypothalamus. In certain studies, food intake was significantly reduced for up to eight hours following the intrahypothalamic injection of rat amylin and rat CGRP. In human trials, an amylin analog, pramlintide, has been shown to reduce weight or weight gain. Amylin may be beneficial in treating metabolic conditions such as diabetes and obesity. Amylin may also be used to treat pain, bone disorders, gastritis, to modulate lipids, in particular triglycerides, or to affect body composition such as the preferential loss of fat and sparing of lean tissue.

The hormone calcitonin (CT) was named for its secretion in response to induced hypercalcemia and its rapid hypocalcemic effect. It is produced in and secreted from neuroendocrine cells in the thyroid that have since been termed C cells. The best-studied action of CT(1-32) is its effect on the osteoclast. In vitro effects of CT include the rapid loss of ruffled borders and decreased release of lysosomal enzymes. Ultimately, the inhibition of osteoclast functions by CT results in a decrease in bone resorption. However, neither a chronic reduction of serum CT in the case of thyroidectomy nor the increased serum CT found in medullary thyroid cancer appears to be associated with changes in serum calcium or bone mass. It is thus most likely that a major function of CT(1-32) is to combat acute hypercalcemia in emergency situations and/or protect the skeleton during periods of "calcium stress" such as growth, pregnancy, and lactation (reviewed in Becker, *JCEM*, 2004, 89(4): 1512-1525 and Sexton, *Current Medicinal Chemistry*, 1999, 6: 1067-1093). Consistent with this is recent data from the calcitonin gene knockout mouse, which removes both the calcitonin and the CGRP-I peptides, that revealed that the mouse had normal levels of basal calcium-related values, but an increased calcemic response (Kurihara H, et al, *Hypertens Res.* 2003 February; 26 Suppl:S105-8).

CT has an effect on plasma calcium levels and inhibits osteoclast function and is widely used for the treatment of osteoporosis. Therapeutically, salmon CT (sCT) appears to increase bone density and decrease fracture rates with minimal adverse effects. CT has also been successfully used over the past 25 years as a therapy for Paget's disease of bone, which is a chronic skeletal disorder that may result in enlarged or deformed bones in one or more regions of the skeleton. CT is also widely used for its analgesic effect on bone pain experienced during osteoporosis, although the mechanism for this effect is not clearly understood.

Calcitonin gene related peptide (CGRP) is a neuropeptide whose receptors are widely distributed in the body, including the nervous system and the cardiovascular system. This peptide seems to modulate sensory neurotransmission and is one of the most potent endogenous vasodilatory peptide discovered to date. Reported biological effects for CGRP include: modulation of substance P in inflammation, nicotinic receptor activity at the neuromuscular junction, stimulation of pancreatic enzyme secretion, a reduction of gastric acid secretion, peripheral vasodilation, cardiac acceleration, neuromodulation, regulation of calcium metabolism, osteogenic stimulation, insulin secretion, an increase in body temperature and a decrease in food intake. (Wimalawansa, Amylin, calcitonin gene-related peptide, calcitonin and ADM: a peptide superfamily. Crit. Rev Neurobiol. 1997; 11(2-3): 167-239). An important role of CGRP is to control blood flow to various organs by its potent vasodilatory actions, as evidenced by a decrease of mean arterial pressure following intravenous administration of CGRP. The vasodilatory actions are also supported by recent analysis of homozygous knockout CGRP mice, which demonstrated elevated peripheral vascular resistance and high blood pressure caused by increased peripheral sympathetic activity (Kurihara H, et al, Targeted disruption of ADM and alphaCGRP genes reveals their distinct biological roles. Hypertens Res. 2003 February; 26 Suppl S 105-8). Thus, CGRP appears to elicit vasodilatory effects, hypotensive effects and an increase in heart rate among other actions.

Prolonged infusion of CGRP into patients with congestive cardiac failure has shown a sustained beneficial effect on hemodynamic functions without adverse effects, suggesting a use in heart failure. Other indications of CGRP use include renal failure, acute and chronic coronary artery ischemia, treatment of cardiac arrhythmia, other peripheral vascular disease such as Raynaud's phenomenon, subarachnoid hemorrhage, hypertension, and pulmonary hypertension. Preeclamptic toxemia of pregnancy and preterm labor is also potentially treatable. Recent therapeutic uses include the use of CGRP antagonists for the treatment of migraine headaches.

Amylin and calcitonin, as herein defined, includes all native and species variations. Examples of amylin and calcitonin include, but are not limited to:

```
human amylin (hAmylin)
                                      (SEQ ID NO: 1)
KCNTATCATQRLANFLVHSSNNFGAILSSTNVGSNTY rat amylin (rAmylin)
                                      (SEQ ID NO: 2)
KCNTATCATQRLANFLVRSSNNLGPVLPPTNVGSNTY salmon calcitonin (sCT)
                                      (SEQ ID NO: 3)
CSNLSTCVLGKLSQELHKLQTYPRTNTGSGTP human calcitonin (hCT)
                                      (SEQ ID NO: 4)
CGNLSTCMLGTYTQDFNKFHTFPQTAIGVGAP.
```

There are many beneficial properties of each of the peptides described herein that can be used alone or in combination to treat or prevent a variety of conditions. We have previously created new and useful peptides having multiple actions that impart improved characteristics not possessed by the existing peptides. For example, in food intake assays, amylin has been shown to have a quick onset, within 30 minutes, but its effect tapers off after 60 minutes. In contrast, salmon calcitonin has been shown to have a delayed effect, with peak levels still maintained at 240 minutes. Novel compounds that can mimic the effects of amylin and/or calcitonin and have quick onset of activity like amylin with the sustained activity of calcitonin were identified that increased the potency and efficacy of either compound alone. Moreover, the combination of certain physicochemical characteristics of amylin, calcitonin, and/or CGRP into a single modality may facilitate intervention at different points in a dysfunctional metabolic circuit. These novel compounds combine desirable activities or properties for a superior therapeutic, which resulted in compounds having at least one desirable characteristic such as higher efficacy, greater potency, greater bioavailability, fewer side effects, ease in manufacture, stability, and/or solubility.

What are described herein are novel methods for modifying body composition using such compounds and their formulations for achieving the same All documents referred to herein are incorporated by reference as though fully set forth herein and for all purposes.

SUMMARY OF THE INVENTION

In a first aspect, methods described herein include the use of an amylin agonist or amylin family peptide compound to modify body composition in a subject in need of modification of body composition, for example, reducing body fat mass but not body lean mass. The change in body composition can be measured by weight (e.g., loss or gain by grams) or by percent body fat and percent lean body mass or protein.

In another aspect, there is provided a method to modify body composition in a subject in need of modification of body composition, for example without limitation reducing body fat mass but not lean body mass, by administration of a compound as described herein, wherein a sufficient amount of such compound is administered to maintain an average plasma concentration of at least a predetermined plasma concentration criterion for an amount of time of at least a predetermined plasma concentration duration criterion.

The terms "amylin family peptide" and the like refer to novel compounds as described herein having at least an N-terminal loop region of amylin or calcitonin, and analogs thereof; an α helix region of at least a portion of an α helix region of calcitonin or analogs thereof or an α helix region having a portion of an amylin α helix region and a calcitonin α helix region or analogs thereof; and a C-terminal tail of amylin or calcitonin, or analogs thereof, with the optional proviso that the C-terminal tail of calcitonin or a calcitonin analog is not proline (Pro), hydroxyproline (Hyp), homoSerine (Hse) or derivatives of Hse.

Methods for treating obesity using amylin and amylin agonists have been described in U.S. Publication No. 2004/0022807 and U.S. Publication No. 2003/0026812, the entire contents of which are incorporated herein by reference and for all purposes. However, it has surprisingly been discovered that amylin and amylin agonists, including amylin family peptides described herein, may have a metabolic effect and may also be used to affect body composition, leading to the desirable loss of body fat, yet preserving lean body mass or minimizing its loss. And further that the desired therapeutic effects are achieved at particular plasma concentrations of drug absent serious adverse side effects, over certain periods of time, and to an unexpected degree. Unless indicated to the contrary, the terms "amylin agonist" and the like expressly include the amylin family peptides described herein having at least one amylin agonist activity as described herein.

In another aspect, methods are provided which include reducing body fat or preventing body fat gain. Other embodiments include controlling body weight and/or sculpting a body's appearance. The subjects to whom these methods may be of interest, and for whom need of treatment is evident, are those individuals who are overweight or obese. However, subjects with lean body composition, for example, body builders and other athletes, may benefit from the methods described herein as well. It may be desirable for them to reduce or maintain their body weight, e.g., to stay in a certain weight class range, yet preserve or increase their lean body mass for greater strength, stamina, endurance and/or a more muscular appearance. Such methods may also be used on any animal, particularly any mammal, more particularly any human, for which a greater lean body mass to fat ratio is desired. Examples of such use include, but are not limited to, creating a superior show dog or creating a superior racehorse.

In certain embodiments, administration of compounds contemplated herein is done peripherally and not centrally, i.e., not through the central nervous system. In a preferred embodiment, a therapeutically or prophylactically effective amount of such compound(s) is administered in a single dose, multiple doses, or continuous administration.

It is also contemplated that methods described herein include the use of amylin agonists described in U.S. Publication No. 2008/0274952, the contents of which are incorporated by reference in its entirety. These amylin agonists will generally retain, at least in part, a biological activity similar to that of native human amylin, i.e., the agonist will generally have amylin-like activity. For example, they may exhibit amylin activity in the treatment or prevention of metabolic conditions and disorders.

It is further contemplated that methods described herein can be used in combination with other forms of nutritional regimens and weight loss programs, such as those already described above, for example, those that include life-style changes that include monitoring food intake (quantity and quality) and exercising, as well as including diet drugs and surgery.

In yet another aspect, there are provided methods which can include the use of amylin and amylin agonists, including amylin family peptides described herein, to reduce the fat content in animals for consumption including producing a leaner meat source. Thus, the present methods can be used with livestock including, but not limited to, chicken, cows, pigs, sheep, and other animal of commercial value.

In yet another aspect, there is provided a method for reducing body fat or body fat gain in a subject in need of treatment while maintaining or increasing lean body mass, the method including administering to the subject an amylin agonist, wherein the amylin agonist has at least 80%, 90%, 92%, 95%, or 100% sequence identity to any of SEQ ID NOs:41 through 145, thereby reducing body fat or body fat gain while maintaining or increasing lean body mass, wherein the amylin agonist is administered in a manner sufficient to maintain an average plasma concentration of the amylin agonist of at least about 50 pg/mL for a period of time selected from the group consisting of at least about 1 hr, at least about 2 hrs, at least about 3 hrs, at least about 4 hrs, at least about 5 hrs, at least about 6 hrs, at least about 7 hrs, at least about 8 hrs, at least about 12 hrs, at least about 1 day, at least about 2 days, at least about 3 days, at least about 1 week, at least about 2 weeks, and at least about 1 month. The terms "about" and the like when used in the context of a numerical value represent +/−10% of the value, unless indicated differently. In a preferred embodiment, the amylin agonist has the structure of SEQ ID NO:138. A peptide having the structure of SEQ ID NO:138 (also known as Cmpd 3236, AC2307, and davalintide), represented by cyclo(2-7)-KCNTATCVLGRLSQELHRLQTYPRT-NTGSNTY-NH$_2$.

In yet another aspect, there is provided a method of altering a body composition of a subject in need of treatment, wherein body fat is reduced and lean body mass is maintained or increased, the method comprising administering to the subject an amylin agonist, wherein the amylin agonist has at least 80%, 90%, 92%, 95%, or 100% sequence identity to any of SEQ ID NOs:41 through 145, wherein the amylin agonist is administered in a manner sufficient to maintain an average plasma concentration of the amylin agonist of at least about 50 pg/mL for a period of time selected from the group consisting of at least about 1 hr, at least about 2 hrs, at least about 3 hrs, at least about 4 hrs, at least about 5 hrs, at least about 6 hrs, at least about 7 hrs, at least about 8 hrs, at least about 12 hrs, at least about 1 day, at least about 2 days, at least about 3 days, at least about 1 week, at least about 2 weeks, and at least about 1 month. In a preferred embodiment, the amylin agonist is SEQ ID NO:138.

In yet another aspect, there is provided a method for reducing body weight in a subject in need of, or desirous of, weight reduction, the method comprising administering to the subject an amylin agonist, wherein the amylin agonist has at least 80%, 90%, 92%, 95%, or 100% sequence identity to any of SEQ ID NOs:41 through 145, wherein the amylin agonist is administered in a manner sufficient to maintain an average plasma concentration of the amylin agonist of at least about 50 pg/mL for a period of time selected from the group consisting of at least about 1 hr, at least about 2 hrs, at least about 3 hrs, at least about 4 hrs, at least about 5 hrs, at least about 6 hrs, at least about 7 hrs, at least about 8 hrs, at least about 12 hrs, at least about 1 day, at least about 2 days, at least about 3 days, at least about 1 week, at least about 2 weeks, and at least about 1 month. In a preferred embodiment, the amylin agonist is SEQ ID NO:138.

In yet another aspect, there is provided a method for reducing caloric intake in a subject in need of reduction thereof, the method comprising administering to the subject an amylin agonist, wherein the amylin agonist has at least 80%, 90%, 92%, 95%, or 100% sequence identity to any of SEQ ID NOs:41 through 145, wherein the amylin agonist is administered in a manner sufficient to maintain an average plasma concentration of the amylin agonist of at least about 50 pg/mL for a period of time selected from the group consisting of at least about 1 hr, at least about 2 hrs, at least about 3 hrs, at least about 4 hrs, at least about 5 hrs, at least about 6 hrs, at least about 7 hrs, at least about 8 hrs, at least about 12 hrs, at least about 1 day, at least about 2 days, at least about 3 days, at least about 1 week, at least about 2 weeks, and at least about 1 month. In a preferred embodiment, the amylin agonist is SEQ ID NO:138.

In yet another aspect, there is provided a method for reducing body fat or body fat gain in a subject in need of treatment while maintaining or increasing lean body mass, the method comprising administering to the subject an amylin agonist, wherein the amylin agonist has at least 80%, 90%, 92%, 95%, or 100% sequence identity to any of SEQ ID NOs:41 through 145, thereby reducing body fat or body fat gain while maintaining or increasing lean body mass, wherein the amylin agonist is administered in a manner sufficient to maintain an integrated plasma concentration of the amylin agonist over time ($AUC_{0\text{-}inf}$) of at least about 1000 pg*h/mL. The term "AUC" (i.e., "area under the curve") as known in the art refers to the integrated area under a graph, for example without limitation, integrated concentration over time. Subscripts to the term "AUC," if present, refer to the limits of integration in the calculation of the area under the curve. The term "inf" in this context refers to extrapolated infinite time as known in the art. In a preferred embodiment, the amylin agonist is SEQ ID NO:138.

In another aspect, the amylin agonists used in the methods described herein are administered in an amount of about 1 µg/kg to about 6 µg/kg; from about 2 µg/kg to about 6 µg/kg; from about 3 µg/kg to about 5 µg/kg; from about 3.5 µg/kg to about 4.5 µg/kg; or about 4 µgkg for a single dose. The amylin agonist has at least 80%, 90%, 92%, 95% or 100% sequence identity to any of SEQ ID NOs:41 through 145; or has at least 92%, 95%, or 100% sequence identity to SEQ ID NO:138. In one embodiment the Amylin agonists are administered subcutaneously.

The details of one or more embodiments described herein are additionally set forth in the accompanying drawings and the description below. Other features, objects, and advantages of the provided methods will be apparent from the description and drawings, and from the claims. All references cited herein are incorporated by reference and for all purposes.

BRIEF DESCRIPTION OF THE DRAWINGS

FIGS. 9A-9F depict the triglyceride, cholesterol, glucose, insulin, leptin, and liver triglyceride levels in lean rats chronically administered amylin.

FIGS. 10A-10E depict the triglyceride, glucose, cholesterol, insulin, and leptin levels in DIO Levin rats chronically administered amylin.

DESCRIPTION OF THE INVENTION

Figure 1A:
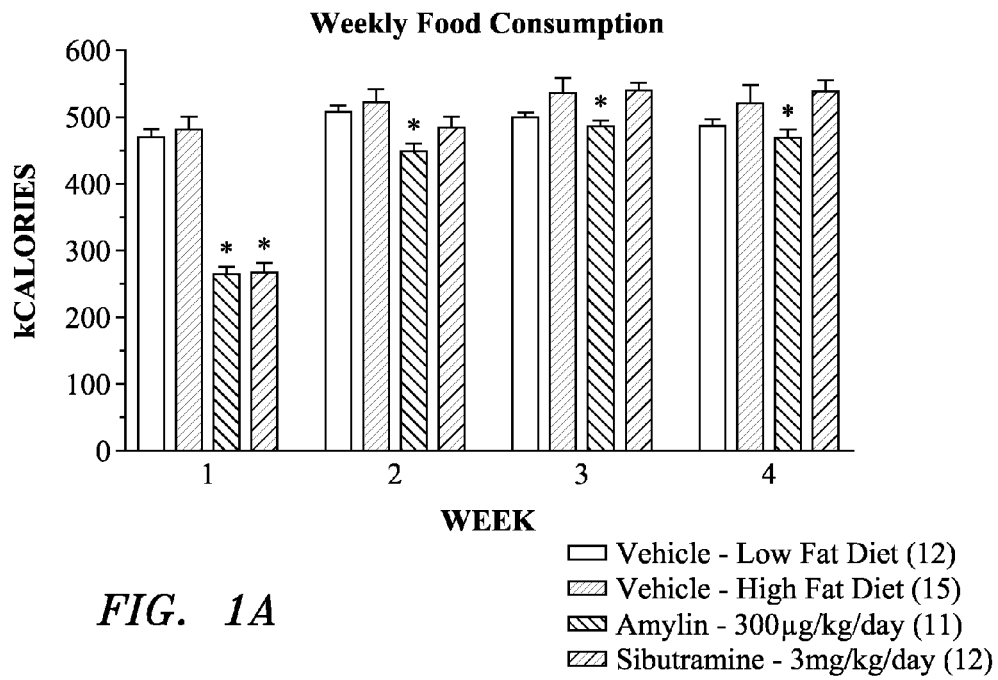
FIGS. 1A and 1B depict the effects of chronic administration of amylin or sibutramine on food consumption and body weight, respectively, in Diet-Induced Obesity (DIO) rats.
Figure 1B:
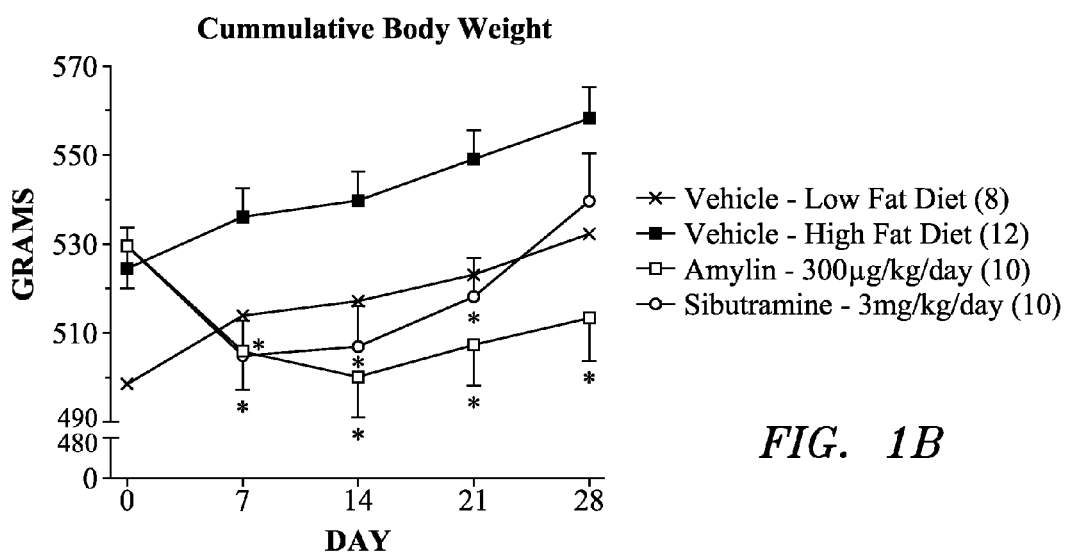

It has now been discovered that amylin, amylin agonist and amylin agonist analogs, including but not limited to the amylin family peptides described herein, and analogs and derivatives thereof, may have metabolic effects on the body and may be used to preferentially reduce body fat and spare, or increase, lean body mass. And further that the desired therapeutic effects are achieved at particular plasma concentrations of drug absent serious adverse side effects, over certain periods of time, and to an unexpected degree.

There are provided herein methods for affecting body composition by reducing body weight, maintaining body weight, or reducing body weight gain, while selectively reducing body fat or preventing body fat gain and maintaining or increasing lean body mass. In certain situations, however, it may be desirable to increase body weight, for example, through selective nutrient intake (e.g., increasing the caloric or fat content), while reducing or maintaining percent body fat, e.g., body building.

The methods described herein contemplate the administration of an effective amount of an amylin or an amylin agonist, including the amylin family peptides described herein, to a subject to affect the desired results as described in the claimed methods.

The administered amylin or amylin agonist, including the amylin family peptides described herein, may be in the form of a peptide, a prodrug, or as pharmaceutical salts thereof. The term "prodrug" refers to a compound that is a drug precursor that, following administration, releases the drug in vivo via some chemical or physiological process, for example, proteolytic cleavage, or upon reaching an environment of a certain pH.

Methods provided herein can be used on any individual in need of such methods or individuals for whom practice of the methods is desired. These individuals may be any mammal including, but not limited to, humans, dogs, cats, horses, cows, buffalo, pigs, chicken and other commercially valuable or companion animals. In one embodiment, the mammal is a human.

Body fat is represented by the total weight of a subject's fat divided by the person's total body weight. Body fat consists of both essential fat and storage fat. Essential fat is that amount necessary for maintenance of normal healthy body functioning and reproductive functions, as would be accepted by a majority of trained physicians. Typically, essential fat is 2-5% in men, and 10-13% in women. Storage fat consists of fat accumulation in adipose tissue, part of which protects internal organs in the chest and abdomen. Lean body mass can be calculated according to the following equation: lean mass=(body mass)−(fat mass+bone mass).

Many methods exist for determining the fat mass and lean mass that make up the body composition, and in the present invention body composition can be determined according to any convenient measure. In one embodiment body composition is determined utilizing DEXA (Dual Energy X-Ray Absorptiometry) technology. This methodology uses an X-Ray technique to look at the density of the body and can then estimate the amount of lean and fat tissue. The exam is precise, non-invasive, accurate, and reliable. In other embodiments hydrostatic weighing can be used to determine body composition. In yet another embodiment body mass composition can be determined by the use of calipers to measure the thickness of subcutaneous fat in multiple places on the body, such as the abdominal area, the subscapular region, arms, buttocks and thighs. These measurements are then used to estimate total body fat with a margin of error of approximately four percentage points. Bioelectric impedance is another method that can be used to determine body composition. In still another embodiment a body mass index formula can be used. These methods of determining body composition are known to those of ordinary skill in the art. The precise method used is not critical, but rather that the measurement be done in a consistent and scientific manner.

"Amylin" is meant to include polypeptides obtained or derived from any species. Thus, the term "amylin" includes the human full-length amino acid peptide, and species variations of amylin, including, e.g., murine, hamster, chicken, bovine, rat, and dog amylin.

Amylin agonists contemplated herein, including amylin family peptides as described herein, have at least one amylin-like activity. "Amylin-like activity" or "amylin activity," as used herein, can be the ability to reduce food intake, body weight, or alter body composition. "Amylin-like activity" or "amylin activity" can also be the ability to bind to, or otherwise directly or indirectly interact with, an amylin receptor or other receptor(s) with which amylin may interact to elicit a biological response, in particular altering body composition. An amylin agonist may be a peptide or a non-peptide compound and includes amylin agonist analogs. Exemplary amylin receptors and their use in methods for screening and assaying for amylin agonists are described in U.S. Pat. No. 5,264,372, incorporated herein by reference. "Amylin-like activity" or "amylin activity" may also include any one or more of those amylin activities described in U.S. Publication No. 2004/0022807, incorporated herein by reference and for all purposes. Assays for measuring amylin activity are known in the art, for example the receptor binding assays, soleus muscle assay, and gastric emptying assay, which are described in the above patent application, as well as food intake assays described in U.S. Publication No. 2008/0274952, the contents of which are incorporated by reference in its entirety and for all purposes.

By "amino acid," "amino acid residue" and the like are meant natural amino acids, unnatural amino acids, and modified amino acids. Unless stated to the contrary, any reference to an amino acid, generally or specifically by name, includes reference to both the D and the L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to homolysine, homoarginine, homoserine azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine (Orn), pentylglycine, pipecolic acid and thioproline. Additional unnatural amino acids include modified amino acid residues which are chemically blocked, reversibly or irreversibly, or chemically modified on their N-terminal amino group or their side chain groups, as for example, N-methylated D and L amino acids or residues wherein the side chain functional groups are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide, a modified amino acid of alanine. Additional residues that can be incorporated are described in Sandberg et al., *J. Med. Chem.* 41: 2481-91, 1998.

Amylin agonists useful in the methods described herein may have an amylin activity greater than or less than native amylin for a particular activity. Thus, for example, amylin agonists may have 3, 5, 10, 50, 100, 500, 1000 times or more activity than native amylin. Furthermore, while it is desirable to use an amylin agonist having similar or greater activity than native amylin, one of ordinary skill in the art would understand that agonists having less activity than native amylin would also be useful in the present methods. Such agonists, for example, may have anywhere from 2, 5, 10, 15, or 20 times less activity than native amylin. Examples of such agonists, more particularly known as amylin agonists analogs (analogs and derivatives of amylin), are described in U.S. Pat. Nos. 5,686,411, 6,114,304, 6,410,511, and 6,610,824, the contents of which are incorporated by reference in their entirety. Amylin agonist analogs also include those compounds described in U.S. Publication No. 2008/0274952, incorporated herein by reference. Amylin agonist analogs useful in the methods described herein may also include fragments of amylin such as those described in EP 289287, the contents of which are herein incorporated by reference.

Amylin agonist analogs useful in the methods provided herein include amylin agonist analogs comprising the following amino acid sequence: $^1A_1$-X-Asn-Thr-$^5$Ala-Thr-Y-Ala-Thr-$^{10}$Gln-Arg-Leu-$B_1$-Asn-$^{15}$Phe-Leu-$C_1$-$D_1$-$E_1$-$^{20}F_1$-$G_1$-Asn-$H_1$Gly-$^{25}I_1$-$J_1$-Leu-$K_1$-$L_1$-$^{30}$Thr-$M_1$-Val-Gly-Ser-$^{35}$Asn-Thr-Tyr-Z (SEQ ID NO:5) wherein $A_1$ is hydrogen Lys, Ser, Ala, des-α-amino Lys, or acetylated Lys; $B_1$ is Ala, Ser or Thr; $C_1$ is Val, Leu or Ile; $D_1$ is His or Arg; $E_{11}$s Ser or Thr; $F_1$ is Ser, Thr, Gln or Asn; $G_1$ is Asn, Gln or His; $H_1$ is Phe, Leu or Tyr; $I_1$ is Ala or Pro; $J_1$ is Ile, Val, Ala or Leu; $K_1$ is Ser, Pro, Leu, Ile or Thr; $L_1$ is Ser, Pro or Thr; $M_1$ is Asn, Asp or Gln; X and Y are independently selected residues (e.g., Cys, Ala, Asp, Ser, Lys) having side chains which are chemically bonded to each other to form an intramolecular linkage;

and Z is optional and if present is hydroxy, amino, alkylamino, dialkylamino, cycloalkylamino, arylamino, aralkylamino, alkyloxy, aryloxy or aralkyloxy; optionally provided that (a) when $A_1$ is Lys, $B_1$ is Ala, $C_1$ is Val, $D_1$ is His, $E_1$ is Ser, $F_1$ is Ser, $G_1$ is Asn, $H_1$ is Phe, $I_1$ is Ala, $J_1$ is Ile, $K_1$ is Ser, $L_1$ is Ser, and $M_1$ is Asn; (b) when $A_1$ is Lys, $B_1$ is Ala, $C_1$ is Ile, $D_1$ is Arg, $E_1$ is Ser, $F_1$ is Ser, $G_1$ is Asn, $H_1$ is Leu, $I_1$ is Ala, $J_1$ is Ile, $K_1$ is Ser, $L_1$ is Pro, and $M_1$ is Asn; (c) when $A_1$ is Lys, $B_1$ is Ala., $C_1$ is Val, $D_1$ is Arg, $E_1$ is Thr, $F_1$ is Ser, $G_1$ is Asn, $H_1$ is Leu, $I_1$ is Ala, $J_1$ is Ile, $K_1$ is Ser, $L_1$ is Pro, and $M_1$ is Asn; (d) when $A_1$ is Lys, $B_1$ is Ala. $C_1$ is Val, $D_1$ is Arg, $E_1$ is Ser, $F_1$ is Ser, $G_1$ is Asn, $H_1$ is Lea, $I_1$ is Pro, $J_1$ is Val, $K_1$ is Pro, $L_1$ is Pro, and $M_1$ is Asn; (e) when $A_1$ is Lys, $B_1$ is Ala, $C_1$ is Val, $D_1$ is His, $E_1$ is Ser, $F_1$ is Asn, $G_1$ is Asn, $H_1$ is Leu, $I_1$ is Pro, $J_1$ is Val, $K_1$ is Ser, $L_1$ is Pro and $M_1$ is Asn; or (f) when $A_1$ is Lys, $B_1$ is Thr, $C_1$ is Val, $D_1$ is Arg, $E_1$ is Ser, $F_1$ is Ser, $G_1$ is His, $H_1$ is Leu, $I_1$ is Ala, $J_1$ is Ala, $K_1$ is Leu, $L_1$ is Pro and $M_1$ is Asp; then one or more of any of $A_1$ to $M_1$ is not an L-amino acid and Z, if present, is not amino.

Suitable side chains for X and Y include groups derived from alkyl sulfhydryls which may form disulfide bonds; alkyl acids and alkyl amines which may form cyclic lactams; alkyl aldehydes or alkyl halides and alkylamines which may condense and be reduced to form an alkyl amine bridge; or side chains which may be connected to form an alkyl, alkenyl, alkynyl, ether or thioether bond. Preferred alkyl chains include lower alkyl groups having from about 1 to about 6 carbon atoms.

The term "alkyl" refers to both straight- and branched-chain alkyl groups. The term "lower alkyl" refers to both straight- and branched-chain alkyl groups having a total of from 1 to 6 carbon atoms and includes primary, secondary, and tertiary alkyl groups. Typical lower alkyls include, for example, methyl, ethyl, n-propyl, isopropyl, n-butyl, isobutyl, t-butyl, n-pentyl, n-hexyl, and the like.

The term "aryl" refers to carbocyclic aromatic groups of 6 to 14 carbon atoms such as phenyl and naphthyl, as well as heterocyclic aromatic groups containing 1 to 3 heteroatoms (nitrogen, oxygen, sulfur, etc.) such as pyridyl, triazolopyrazine, pyrimidine and the like.

The term "aralkyl" refers to an "aryl" group of 6 to 10 carbon atoms directly attached to an "alkyl" group of 1 to 4 carbon atoms and includes for example benzyl, p-chlorobenzyl, p-methylbenzyl, and 2-phenylethyl.

The term "cycloalkyl" refers to cyclic alkyl groups of 5 to 8 carbon atoms.

Biologically active derivatives of the amylin agonist analogs described herein, including the amylin family peptides described herein, are also included within the scope of amylin agonist analogs useful in the present methods in which the stereochemistry of individual amino acids may be inverted from (L)/S to (D)/R at one or more specific sites. Also included within the scope of amylin agonist analogs useful in the present methods are the agonist analogs modified by glycosylation of Asn, Ser and/or Thr residues.

Biologically active agonist analogs of amylin which contain less peptide character, as commonly judged in the art, are also included in the scope of amylin agonist analogs useful in the present methods. Such peptide mimetics may include, for example, one or more of the following substitutions for —CO—NH— amide bonds: depsipeptides (—CO—O—), iminomethylenes (—$CH^2$—NH—), trans-alkenes (—CH≈CH—), β-enaminonitriles (—C(=CH—CN)—NH—), thioamides (—CS—NH—), thiomethylenes (—S—$CH_2$— or —$CH_2$—S—), methylenes, and retro-amides (—NH—CO—).

In certain embodiments, the compounds contemplated for the methods provided herein have an amylin or amylin analog loop region, at least a portion of a calcitonin or calcitonin analog α helix region, and an amylin or amylin analog C-terminal tail. In other embodiments, the contemplated compounds have a calcitonin or calcitonin analog loop region, at least a portion of a calcitonin or calcitonin analog α helix region, and an amylin or amylin analog C-terminal tail. In still other embodiments, compounds useful in the methods described herein have an amylin or amylin analog loop region, at least a portion of an amylin or amylin analog α helix region and at least a portion of a calcitonin or calcitonin analog α helix region, and an amylin or amylin analog C-terminal tail. In yet other embodiments, compounds useful in the methods described herein have a calcitonin or calcitonin analog loop region, at least a portion of an amylin or amylin analog α helix region and at least a portion of a calcitonin or calcitonin analog α helix region, and an amylin or amylin analog C-terminal tail. In still yet other embodiments, compounds useful in the methods described herein have an amylin or amylin analog loop region, a portion or a calcitonin or calcitonin analog α helix region or at least a portion of an amylin or amylin analog α helix region and at least a portion of a calcitonin or calcitonin analog α helix region, and a calcitonin or calcitonin analog C-terminal tail.

In certain embodiments, the loop region of the compounds useful in the methods described herein may further comprise no more than one, two, three, or four modifications including substitutions, insertions, or deletions from the amylin or calcitonin loop, and analogs thereof. It is further contemplated that the contemplated compounds may have additional modifications at the N-terminal portion of the loop comprising a N-capped region, that may have hydrophobic or hydrophilic characteristics such as acetyl, isocaproyl, 3,6-dioxyoctanoic acid, or 1-amino-4,7,10-trioxa-13-tridecanamine succinimic acid, and the like known in the art. Modifications may further include one, two, three or more additional amino acids. This is an area which allows for many modifications, but would be understood by one of skill in the art based upon what is exemplified and described herein.

The terms "analog" and the like refer to a peptide with sequence derived from that of a base reference peptide, e.g., amylin and/or calcitonin, and includes insertions, substitutions, extensions, and/or deletions of the reference amino acid sequence, preferably having at least 50 or 55% amino acid sequence identity with the base peptide, more preferably having at least 70%, 80%, 90%, 92%, or 95% amino acid sequence identity with the base peptide. In one embodiment, such analogs may comprise conservative or non-conservative amino acid substitutions (including non-natural amino acids and L and D forms). Analogs include compounds having agonist and compounds having antagonist activity. Analogs, as herein defined, also include derivatives. The terms "derivative" and the like refer to a reference peptide or analogs thereof having a chemical modification of one or more amino acid side groups, α-carbon atoms, terminal amino group, or terminal carboxylic acid group. Chemical modifications contemplated herein include, but are not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the desamino, N-lower alkyl, N-di-lower alkyl, and N-acyl modifications. Modifications of the terminal amino include, without limitation, the desamino, N-lower alkyl, N-di-lower alkyl, and N-acyl modifications, such as alkyl acyls, branched alkylacyls, alkylarylacyls. Modifications of the terminal carboxy group include, without limitation, the amide, lower alkyl amide, dialkyl amide, arylamide, alkylarylamide and lower alkyl ester modifications. Lower alkyl is C1-C4 alkyl. Furthermore, one or more side groups, or terminal groups, may be protected by protective groups known to the ordinarily-skilled synthetic chemist. The α-carbon of an amino acid may be mono- or dimethylated.

In general, with respect to an amino acid sequence, the term "modification" includes substitutions, insertions, elongations deletions, and derivatizations alone or in combination. In one embodiment, an analog of a parent compound described herein contains no more than 1, 2, 3, 4, 5, 6 or 7 total number of modifications, alone or in combination, compared to the parent compound. However, an elongation at either or both termini is not viewed as a modification per se, but as a creating a molecule that contains or comprises the analog. The compounds useful in the methods described herein may include one or more modifications of a "non-essential" amino acid residue. In the context of such modification, a "non-essential" amino acid residue is a residue that can be altered, i.e., deleted or substituted, in the amino acid sequence without abolishing or substantially reducing the agonist activity of the analog polypeptide.

Substitutions include conservative amino acid substitutions. A "conservative amino acid substitution" is one in which the amino acid residue is replaced with an amino acid residue having a similar side chain, or physicochemical characteristics (e.g., electrostatic, hydrogen bonding, isosteric, hydrophobic features). The amino acids may be naturally occurring or nonnatural (unnatural). Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), β-branched side chains (e.g., threonine, valine, isoleucine) and aromatic side chains (e.g., tyrosine, phenylalanine, tryptophan, histidine). Substitutions may also include non-conservative changes.

The compounds useful in the methods described herein may also be further derivatized by chemical alterations such as amidation, glycosylation, acylation, sulfation, phosphorylation, acetylation, and cyclization. Such chemical alterations may be obtained through chemical or biochemical methodologies, as well as through in-vivo processes, or any combination thereof. Derivatives of the compounds useful in the methods described herein may also include conjugation to one or more polymers or small molecule substituents. One type of polymer conjugation is linkage or attachment of polyethylene glycol ("PEG") polymers, polyamino acids (e.g., poly-his, poly-arg, poly-lys, etc.) and/or fatty acid chains of various lengths to the N- or C-terminus or amino acid residue side chains of an AFP-6 analog. Small molecule substituents include short alkyls and constrained alkyls (e.g., branched, cyclic, fused, adamantyl), and aromatic groups. In addition, basic residues such as R and K may be replaced with homoR and homoK, citrulline (Cit), or ornithine to improve metabolic stability of the peptide. Compounds useful in the methods described herein also include acid as well as amide forms of the peptides, as known in the art.

In certain embodiments, the α helix region of the novel compounds comprise at least four consecutive amino acids of a calcitonin or calcitonin analog α helix region. In other embodiment, the α helix region comprises at least 5, 6, 7, or 8 consecutive amino acids of a calcitonin or calcitonin analog α helix region. In other embodiments, the α helix region comprises at least 10, 11, 12, 13, 14, 15, 16, 17, 18, 19, 20, 21 or more consecutive amino acids of a calcitonin or calcitonin analog α helix region. In certain embodiments, when the number of consecutive amino acids are less than 8, it is contemplated that the α helix region further comprises at least 4, 5, 6, 7, 9, 10, 11, or more consecutive amino acid of an amylin or amylin analog α helix region. In certain embodiments, it is envisioned that the less amino acids of calcitonin or calcitonin analog, the more amino acids of an amylin or amylin analog may be found in the α helix region of the novel compounds. The number of amino acids comprising the α helix region may be from about 10 to 23 amino acids. Accordingly, the α helix region may be 10, 11, 12, 13, 14, 15, 16, 17, 18, 19, 20, 21, 22, or 23 amino acids long. Moreover, the amino acids should provide for about three to about six α helical turns. It is further contemplated that the α helix region of the novel compounds may further comprise no more than one, two, three, four, five, six, seven, eight or 10 modifications including substitutions, insertions, or deletions from that of the calcitonin and/or amylin α helix region, and analogs thereof.

In certain embodiments, the C-terminal tail of the novel compounds comprise at least the last six, five, or four amino acids of either amylin or calcitonin, and analogs thereof. In certain embodiments, the C-terminal tail of the novel compounds comprise at least a portion of the C-terminal end having a β turn. In certain embodiments, the β turn is introduced by the amino acid combination of Gly-Ser. Accordingly, the novel compounds may have a C-terminal end comprising a portion of an amylin or calcitonin C-terminal tail (and analogs thereof) having Gly-Ser or starting at Gly-Ser.

In certain embodiments, the C-terminal tail of the novel compounds may further comprise no more than one, two, or three, modifications including substitutions, insertions, or deletions from the amylin or calcitonin loop, and analogs thereof. It is further contemplated that the novel compounds may have additional modifications at the C-terminal portion of the C-terminal tail which may include L-octylglycine, 4ABU (4-aminobutyric acid), 9Anc (9 aminononanoic acid, 3,6-dioxyoctanoic acid or 1-amino-4,7,10-trioxa-13-tridecanamine succinimic acid. Modification may further include one, two, three or more additional amino acids. The types of modification contemplated in this area would be understood by one of skill in the art based upon what is exemplified further in the present application.

In certain embodiments of the amylin family peptide described herein, a loop region is defined as that region found at the N-terminal end comprising at least 5 to 8 amino acids, wherein the first and last amino acid are capable of creating a bond, for example, residues at positions 2-7 of amylin or residues at positions 1-7 of calcitonin and their corresponding regions in their respective analogs. In another embodiment, a α helix region is defined as the internal portion of amylin or calcitonin flanked by the loop region and the C-terminal tail which structurally forms an α helix, for example, residues at positions 8-23 of amylin or residues at positions 8-27 of calcitonin and their corresponding regions in their respective analogs. In yet another embodiment, a C-terminal tail is defined as that region after the α helix e.g., residues at positions 33-37 of amylin or longer such as residues at positions 27-37 or residues at positions 27 or 28 to 32 of calcitonin.

Included in the compounds useful in the methods described herein are both the amide and acid forms of the disclosed compounds.

In certain embodiments, compounds described herein comprise at least a loop region, an α helix region, and a C-terminal tail. The loop region comprises an amino sequence comprising the formula X-"XY-linker sequence"-Y (SEQ ID NO:6) wherein X and Y are capable of creating a bond and are independently selected residues having side chains which are chemically bonded to each other to form an intramolecular linkage such as disulfide bonds; amide bond; alkyl acids and alkyl amines which may form cyclic lactams; alkyl aldehydes or alkyl halides and alkylamines which may condensed and be reduced to form an alkyl amine or imine bridge; or side chains which may be connected to form an alkyl, alkenyl, alkynyl, ether or thioether bond, and wherein "XY-linker sequence" is as described below. Alkyl chains may include lower alkyl groups having from about 1 to about 6 carbon atoms. In certain embodiments, the intramolecular linkage may be a disulfide, amide, imine, amine, alkyl and alkene bond. In certain embodiments, X and Y are independently selected from Ser, Asp, Glu, Lys, Orn, or Cys. In certain embodiments, X and Y are Cys and Cys. In other embodiments, X and Y are Ser and Ser. In still other embodiments, X and Y are Asp and Lys or Lys and Asp.

The "XY-linker sequence" comprises an amino acid sequence of 3, 4, 5, or 6 amino acids between X and Y. In certain embodiments, the "XY-linker sequence" comprises an amino acid sequence having a region with one or more substituted or unsubstituted hydroxyl-containing residues next to Y. For example, the hydroxyl containing residue region may have at least 2 of the 3 amino acids adjacent Y that are either a Ser or Thr. The other amino acids in the "XY-linker sequence" may be any amino acid. In certain embodiments, the "XY-linker sequence" is 3 amino acids. In other embodiments, the "XY-linker sequence" is 4 amino acids. In still other embodiments, the "XY-linker sequence" is 5 amino acids. In yet other embodiments, the "XY-linker sequence" is 6 amino acids. Accordingly, the "XY linker sequence" can be represented by $Xaa_2$-$Xaa_3$-$Xaa_4$-$Xaa_5$-$Xaa_6$-$Xaa_7$ (SEQ ID NO:7) In certain embodiments, $Xaa_2$, $Xaa_3$, and/or $Xaa_4$ may absent. In certain embodiments, $Xaa_5$, $Xaa_6$, and $Xaa_7$ comprise a hydroxy-containing residue region. As such, at least two of the three amino acids thereof can be a Ser, hSer, Thr, alloThr, d-Thr, or other unnatural analog thereof containing a side chain hydroxy. $Xaa_2$ can be any amino acid or absent, $Xaa_3$ can be any amino acid or absent, $Xaa_4$ can be any amino acid or absent, $Xaa_5$ can be any amino acid if $Xaa_6$ is a Ser or Thr and $Xaa_7$ is a Ser or Thr, $Xaa_6$ can be any amino acid if $Xaa_5$ is a Ser or Thr and $Xaa_7$ is a Ser or Thr, $Xaa_7$ can be any amino acid if $Xaa_5$ is Ser or Thr and $Xaa_6$ is Ser or Thr. Accordingly, in certain embodiment, $Xaa_2$ is any amino acid or absent, $Xaa_3$ is Ala, Gly, Ser, Asp or absent, $Xaa_4$ is Asn, Ala, Asp, Gly or absent; $Xaa_5$ is Ala, Leu, Thr, or Ser; $Xaa_6$ is Ala, Ser, or Thr; and $Xaa_7$ is Ala, Ser, Val, Hse, (S)-2-amino-3-hydroxy-methylbutanoic acid (Ahb), (2S,3R)-2-amino-3hydroxy-methylpentanoic acid (Ahp), D-Thr, Thr, or a derivative thereof. In other embodiments $Xaa_2$ is any amino acid or absent, $Xaa_3$ is Ser, Gly, or absent, $Xaa_4$ is Asn or Asp, $Xaa_5$ is Ala, Ser, Thr or Leu, $Xaa_6$ is Ala, Thr or Ser, and $Xaa_7$ is Ser, D-Thr, alloThr or Thr. In certain embodiments, the loop region comprises the above-described representations wherein $Xaa_3$ is Ala, wherein $Xaa_3$ is Ser or Gly. Alternatively or additionally, the loop region comprises the above described representations wherein $Xaa_4$ is Ala, wherein $Xaa_4$ is Asn, wherein $Xaa_4$ is Asp, or wherein $Xaa_4$ is Gly. Alternatively or additionally, the loop region comprises the above-described representations wherein $Xaa_5$ is Ala, wherein $Xaa_5$ is Thr, or wherein $Xaa_5$ is Leu. Alternatively or additionally, the loop region comprises the above described representations wherein $Xaa_6$ is Ser or wherein $Xaa_6$ is Ala. Alternatively or additionally, the loop region comprises the above-described representations wherein $Xaa_7$ is Thr or wherein $Xaa_7$ is D-Thr. It is further contemplated that no more than one, two, or three modifications such as substitutions, insertions, deletions, and/or derivatizations may be made to the loop region.

It should be noted that throughout the application that alternatives are written in Markush groups, for example, each amino acid position that contains more than one possible amino acid. It is specifically contemplated that each member of the Markush group should be considered separately, thereby comprising another embodiment of the provided method, and the Markush group is not to be read as a single unit.

Examples of the loop region of the compounds contemplated herein include, but are not limited to, CNTATC (SEQ ID NO:8); CATATC (SEQ ID NO:9); CDTATC (SEQ ID NO:10); CGTATC (SEQ ID NO:11); CNAATC (SEQ ID NO:12); CNTSTC (SEQ ID NO:13; CNTAdThrC (SEQ ID NO:14); CNTAT(OPO3H2)C (SEQ ID NO:15); CNTASC (SEQ ID NO:16); CNTAAC (SEQ ID NO:17); CNTAVC (SEQ ID NO:18); CNTAHseC (SEQ ID NO:19); CNTAAhbC (SEQ ID NO:20) CNTAAhpC (SEQ ID NO:21) CSNLSTC (SEQ ID NO:22); CGNLSTC (SEQ ID NO:23); CANLSTC (SEQ ID NO:24); CSALSTC (SEQ ID NO:25); CSNASTC (SEQ ID NO:26); CSNLATC (SEQ ID NO:27); and CSNLSAC (SEQ ID NO:28). As previously noted, it is further contemplated that no more than one, two, or three modifications such as substitutions, insertions, deletions, and/or derivatizations may be made to the loop region.

The loop region of the novel compounds may further comprise modifications or additional amino acids at the N-terminal end. Such modifications include the addition of compounds such as Lys, Ala, Phe, Ile, Ser, Octylglycine, Isocap, Fmoc-3,6-dioxyoctanoic acid, Fmoc-1-amino-4,7,10-trioxa-13-tridecanamine succinimic acid, acetyl, and/or groups for solubility, delivery, signaling. Exemplary modified loops include the addition of e.g. Lys or Ile to a loop region sequence provided herein. For example, the modified loop region may be KCNTATC (SEQ ID NO:29). In certain embodiments, the additions and/or modifications at the N-terminal end of the loop region may change the loop region. For example, the loop region of compounds useful in the methods described herein may be modified as follows: cyclo(2,7) (1-7) hAmylin, cyclo(2-7)[$^2$Asp $^7$Lys] (1-7) hAmylin, N-isocaproyl (1-7) hAmylin, N-3,6 dioxaoctanoyl (1-7) hAmylin, L-Octylglycine (1-7) hAmylin, Acetyl [$^2$Agy $^7$Agy] (1-7) hAmylin wherein Agy is allylglycine, Acetyl [$^1$Ala] (1-7) hAmylin, [$^1$Thr $^3$Asp] (1-7) hAmylin, Isocap [$^7$Ala] (5-7) sCT, Acetyl [$^2$Agy $^7$Agy] (1-7) sCT, and cyclo (1,7) [$^1$Asp $^7$Lys] (1-7) sCT. Therefore, taking the example of Isocap [$^7$Ala] (5-7) sCT, certain embodiments comprise a modification at the N-terminal region of the loop region of the compound useful in the methods described herein such that amino acids $Xaa_2$ to $Xaa_5$ are absent.

Throughout the application, the amino acid sequences may be referred to as amino acids at position "a" to position "b" adjacent to a reference peptide. For example, (1-7) hAmylin refers to the amino acid sequence from position 1 to position 7, inclusive, of human amylin (SEQ ID NO:1). Modification to the reference peptide may be shown as: position of modification adjacent to the modification. For example, [$^2$Asp $^7$Lys] (1-7) hAmylin represents the amino acid sequence at positions 1 to 7 of human amylin with a modification of a Cys to Asp at position 2 and a modification of a Cys to Lys at position 7.

The α helix region of the novel compound may be about 8 to 23 amino acids in length. In certain embodiments, the α helix region is amphiphatic. In certain embodiments, the α helix region comprises about 3 to 6 helical turns. In certain embodiments, the α helix region comprises 3, 4, 5, or 6 helical turns. In other embodiments, the α helix region is a rigid structure equivalent to about 3, 4, 5, or 6 helical turns. An example of an idealized helix is LLQQLQKLLQKLKQY (SEQ ID NO:30). In certain embodiments, the α helix is an amphiphatic structure. Accordingly, characteristics of desirable amino acids that would provide this type of structure may be selected.

It has been found that the calcitonin α helix region, a combination of an amylin and a calcitonin α helix region, or parts thereof, and/or some CGRP elements are desirable in the α helix region of the novel compounds. It is contemplated that, as with the loop region, the α helix region can be from any amylin or calcitonin, and analogs thereof. Accordingly, in certain embodiments, the α helix region is at least a portion of an α helix region of calcitonin or calcitonin analog. In other embodiments, the α helix region is at least a portion of an α helix region of calcitonin or calcitonin analog and at least a portion of an α helix of an amylin or amylin analog. In still other embodiments, the α helix region of the novel compounds contain elements of CGRP. It is further contemplated that novel compounds may have no more than one, two, three, four, five, six, seven, eight, nine, or ten further modifications such as substitutions, insertions, deletions, and/or derivatizations.

In certain embodiments, the α helix region of compounds useful in the methods described herein may comprise amino acids from position 8 of sCT to position 18, 19, 20, 21, 22, 23, 24, 25, 26, or 27 of sCT. Moreover, the α helix region may comprise more than one portion of a calcitonin or calcitonin analog α helix region of the same or different species, for example (8-21) sCT (19-27) sCT; (8-21) sCT (18-27) sCT; or (8-16) hCT (17-27) sCT; or [$^{11}$Arg] (8-16) hCT [$^{18}$Arg] (17-27) sCT. Alternatively or additionally, the above described α helix of (8-18) sCT to (8-27) sCT may further comprise the substitutions of one or more of [$^{10}$Aib], [$^{11}$Arg], [$^{11}$Orn], [$^{11}$hArg], [$^{11}$Cit], [$^{11}$hLys], [$^{11}$Lys(for)], [$^{17}$Aib], [$^{18}$Arg], [$^{18}$Orn], [$^{18}$hArg], [$^{18}$Cit], [$^{18}$hLys], [$^{18}$Lys(for)], [$^{18}$Lys (PEG5000)], [$^{22}$Leu], [$^{24}$Pro] or any combination thereof.

In one embodiment, an α helix region of compounds useful in the methods described herein can be represented by (α helix region type I): $R_1$-VL-Xaa$_{10}$-Xaa$_{11}$-LSQ-Xaa$_{15}$-L-Xaa$_{17}$-Xaa$_{18}$-LQT-Xaa$_{22}$-P-Xaa$_{24}$-TNT-$R_1$ (SEQ ID NO:31), wherein Xaa$_{10}$ is Gly or Aib; Xaa$_{11}$ is Lys, Arg, Orn, hArg, Cit, hLys, or Lys(for); Xaa$_{15}$ is Glu or Phe; Xaa$_{17}$ is His or Aib; Xaa$_{18}$ is Lys, Arg, Orn, hArg, Cit, hLys, Lys(for), Lys (PEG 5000); Xaa$_{22}$ is Tyr or Leu; Xaa$_{24}$ is Arg or Pro; or $R_1$ is absent or comprises 1-4 additional amino acids.

Again, it should be remembered that each member of the Markush group, or a combination thereof, is another embodiment and is not to be read as a single unit. This is a shorthand method for stating, as an example, embodiments include an α helix region type I formula where, Xaa$_{18}$ can be a Lys, Arg, Orn, hArg (homoarginine, hArg), Cit, hLys (homolysine, hLys), or Lys(for), and each variation is a separate embodiment. Accordingly, the α helix region type I formula has one embodiment where Xaa$_{18}$ is Lys. It has another embodiment where Xaa$_{18}$ is Arg, and so on. It is further contemplated that the α helix region may contain no more than one, two, three, four, five, six, seven, eight, nine, or ten modifications such as substitutions, insertions, deletions, and/or derivatizations. Accordingly, the compounds of α helix region type I may have further deletions at the C-terminal end. In certain embodiments, the amino acids of $R_1$ are capable of forming an α helix turn.

Examples of an α helix region type I of compounds useful in the methods described herein include, but are not limited to (8-18) sCT, (8-21) sCT, (8-24) sCT, (8-27) sCT, [$^{11}$Arg] (8-18) sCT, [$^{18}$Arg] (8-18) sCT, [$^{11}$Arg $^{18}$Arg] (8-18) sCT, [$^{11}$Orn $^{18}$Orn] (8-18) sCT, [$^{11}$Arg $^{18}$Cit] (8-18) sCT, [$^{11}$hArg $^{18}$hArg] (8-18) sCT, [$^{11}$Arg $^{18}$Orn] (8-18) sCT, [$^{11}$Cit $^{18}$Arg] (8-18) sCT, [$^{11}$Cit $^{18}$Cit] (8-18) sCT, [$^{11}$hLys $^{18}$hLys] (8-18) sCT, [$^{10}$Aib $^{11}$Arg $^{17}$Aib $^{18}$Arg] (8-18) sCT, [$^{11}$Lys(for)$^{18}$Lys (for)] (8-18) sCT, [$^{10}$Aib $^{11}$Lys(for)$^{17}$Aib $^{18}$Lys(for)] (8-18) sCT, [$^{11}$Arg $^{18}$Lys(PEG 5000)] (8-18) sCT, [$^{11}$Arg] (8-21) sCT, [$^{18}$Arg] (8-21) sCT, [$^{11}$Arg $^{18}$Arg] (8-21) sCT, [$^{11}$Orn $^{18}$Orn] (8-21) sCT, [$^{11}$Arg$_{18}$Cit] (8-21) sCT, [$^{11}$hArg $^{18}$hArg] (8-21) sCT, [$^{11}$Arg $^{18}$Orn] (8-21) sCT, [$^{11}$Cit $^{18}$Arg] (8-21) sCT, [$^{11}$Cit $^{18}$Cit] (8-21) sCT, [$^{11}$hLys $^{18}$hLys] (8-21) sCT, [$^{10}$Aib $^{11}$Arg $^{17}$Aib $^{18}$Arg] (8-21) sCT, [$^{11}$Lys(for)$^{18}$Lys(for)] (8-21) sCT, [$^{10}$Aib $^{11}$Lys(for)$^{17}$Aib $^{18}$Lys(for)] (8-21) sCT, [$^{11}$Arg $^{18}$Lys(PEG 5000)] (8-21) sCT, [$^{11}$Arg] (8-24) sCT, [$^{18}$Arg] (8-24) sCT, [$^{11}$Arg $^{18}$Arg] (8-24) sCT, [$^{11}$Arg $^{18}$Arg $^{22}$Leu] (8-24) sCT, [$^{11}$Arg $^{18}$Arg $^{24}$Pro] (8-24) sCT, [$^{11}$Orn $^{18}$Orn] (8-24) sCT, [$^{11}$Arg $^{18}$Cit] (8-24) sCT, [$^{11}$hArg $^{18}$hArg] (8-24) sCT, [$^{11}$Arg $^{18}$Orn] (8-24) sCT, [$^{11}$Cit $^{18}$Arg] (8-24) sCT, [$^{11}$Cit $^{18}$Cit] (8-24) sCT, [$^{11}$hLys $^{18}$hLys] (8-24) sCT, [$^{10}$Aib $^{11}$Arg $^{17}$Aib $^{18}$Arg] (8-24) sCT, [$^{11}$Lys(for)$^{18}$Lys(for)] (8-24) sCT, [$^{10}$Aib $^{11}$Lys(for)$^{17}$Aib $^{18}$Lys(for)] (8-24) sCT, [$^{11}$Arg $^{18}$Lys(PEG 5000)] (8-24) sCT, [$^{11}$Arg] (8-27) sCT, [$^{18}$Arg] (8-27) sCT, [$^{11}$Arg $^{18}$Arg] (8-27) sCT, [$^{11}$Arg $^{18}$Arg $^{22}$Leu] (8-27) sCT, [$^{11}$Arg $^{18}$Arg $^{24}$Pro] (8-27) sCT, [$^{11}$Orn $^{18}$Orn] (8-27) sCT, [$^{11}$Arg $^{18}$Cit] (8-27) sCT, [$^{11}$hArg $^{18}$hArg] (8-27) sCT, [$^{11}$Arg $^{18}$Orn] (8-27) sCT, [$^{11}$Cit $^{18}$Arg] (8-27) sCT, [$^{11}$Cit $^{18}$Cit] (8-27) sCT, [$^{11}$hLys $^{18}$hLys] (8-27) sCT, [$^{10}$Aib $^{11}$Arg $^{17}$Aib $^{18}$Arg] (8-27) sCT, [$^{11}$Lys(for)$^{18}$Lys(for)] (8-27) sCT, [$^{10}$Aib $^{11}$Lys(for)$^{17}$Aib $^{18}$Lys(for)] (8-27) sCT, [$^{11}$Arg $^{18}$Lys(PEG 5000)] (8-27) sCT, [$^{11}$Arg $^{18}$Arg] (8-21) sCT-(19-27) sCT, and [$^{11}$Arg $^{18}$Arg] (8-21) sCT-[$^{18}$Leu] (18-27) sCT.

In certain embodiments, the α helix region of compounds useful in the methods described herein may comprise a portion of an α helix region of amylin or amylin analog and a portion of an α helix region of calcitonin or calcitonin analog. The α helix region may comprise amino acids from position 8 of hAmylin to 11, 12, 13, 14, 15, 16, 17, 18 or 19 of hAmylin and amino acids from position 13, 14, 15, 16, 17, 18, and 19 of sCT to position 18, 19, 20, 21, 22, 23, 24, 25, 26, or 27 of sCT. Alternatively or additionally, the above described α helix region of amylin and calcitonin may further comprise the substitutions of one or more of $^8$Val, $^9$Leu, $^9$Met, $^{10}$Gly, $^{10}$His $^{12}$Thr $^{13}$Thr, $^{13}$Asn, $^{13}$Phe, $^{13}$Tyr, $^{14}$Arg, $^{14}$Ala, $^{14}$Asp, $^{14}$Glu, $^{14}$Gln, $^{14}$Thr, $^{14}$Gly, $^{15}$Leu, $^{15}$Ser, $^{15}$Glu, $^{15}$Ala, $^{15}$Tyr, $^{16}$Asp, $^{17}$Ser, $^{17}$Phe, $^{18}$Arg, $^{17}$Aib, $^{18}$Arg, $^{18}$Orn, $^{18}$hArg, $^{18}$Cit, $^{18}$hLys, $^{18}$Lys(for), $^{18}$Lys(PEG5000), $^{19}$Phe, $^{20}$His, $^{21}$Asn, $^{22}$Met, $^{22}$Val, $^{22}$Phe, $^{22}$Leu, $^{24}$Pro, or any combination thereof. In certain embodiments, the number of amino acids in the α helix region is at least 6 amino acids. In certain embodiments, the number of amino acids in the α helix region is at least 10 amino acids. In other embodiments, the number of amino acids in the α helix region is 11, 12, 13, 14, 15, 16, 17, 18, 19, 20, 21, 22, 23 or even greater. In other embodiments, the number of amino acids in the α helix region is 24 or more.

In one embodiment, an α helix region of compounds useful in the methods described herein can be represented by (α helix region type II): $R_1$-Xaa$_8$-Xaa$_9$-Xaa$_{10}$-R-Xaa$_{12}$-Xaa$_{13}$-

Xaa$_{14}$-Xaa$_{15}$-Xaa$_{16}$-Xaa$_{17}$-Xaa$_{18}$-Xaa$_{19}$-Xaa$_{20}$-Xaa$_{21}$-Xaa$_{22}$-P-Xaa$_{24}$-TNT-R$_1$ (SEQ ID NO:32), wherein Xaa$_8$ is Ala or Val; Xaa$_9$ is Thr, Met or Leu; Xaa$_{10}$ is Gln, Gly, His; Xaa$_{12}$ is Leu, or Thr; Xaa$_{13}$ is Ala, Thr, Asn, Phe, Tyr, Ser, or Thr; Xaa$_{14}$ is Asn, Arg, Ala, Asp, Glu, Gln, Thr, or Gly; Xaa$_{15}$ is Phe, Leu, Ser, Glu, Ala, Asp, or Tyr; Xaa$_{16}$ is Leu or Asp; Xaa$_{17}$ is Val, His, Ser, Phe, or Aib; Xaa$_{18}$ is His, Arg, Lys, Orn, hArg, Cit, hLys, Lys(for), or Lys(PEG5000); Xaa$_{19}$ is Leu, Ser or Phe; Xaa$_{20}$ is Gln or His; Xaa$_{21}$ is Thr or Asn; Xaa$_{22}$ is Tyr, Val, Phe, Leu or Met; Xaa$_{24}$ is Arg or Pro; and R$_1$ is absent or comprises 1-4 additional amino acids.

Again, it should be remembered that each member in the Markush group, or a combination thereof, is another embodiment and is not to be read as a single unit. It is further contemplated that the α helix region may contain no more than one, two, three, four, five, six, seven, eight, nine, or ten modifications such as substitutions, insertions, deletions, and/or derivatizations of the compounds described herein. For example, in certain embodiments, the compounds of α helix region type II may have deletions at the C-terminal end resulting in the deletion of position 27, 26, 25, 24, or 22. In other embodiments, however, the deletions do not remove amino acids of positions 19, 20, 21, or 22.

Examples of an α helix region of type II include, but is not limited to [$^{8}$Val $^{9}$Leu $^{10}$Gly] (11-15) hAmylin (16-27) sCT, [$^{8}$Val $^{9}$Leu $^{10}$Gly] (11-15) hAmylin [$^{18}$Arg] (16-27) sCT, (8-12) hAmylin [$^{18}$Arg] (13-27) sCT, (8-18) hAmylin (19-23) sCT, (8-18) hAmylin (19-27) sCT, [$^{15}$Glu $^{18}$Arg] (8-18) hAmylin (19-24) sCT, [$^{14}$Arg $^{15}$Ser] (8-18) hAmylin (19-22) sCT, [$^{13}$Ala $^{14}$Ala $^{15}$Ala] (8-18) hAmylin (19-27) sCT, [$^{13}$Ala $^{14}$Asp $^{15}$Ala] (8-18) hAmylin (19-22) sCT, [$^{13}$Ala $^{14}$Asp] (8-18) hAmylin (19-23) sCT, [$^{13}$Ala $^{14}$Asp] (8-18) hAmylin (19-27) sCT, [$^{13}$Ala $^{14}$Ala] (8-18) hAmylin (19-22) sCT, [$^{13}$Ala $^{14}$Glu] (8-18) hAmylin (19-22) sCT, [$^{13}$Thr $^{14}$Asp $^{15}$Tyr] (8-18) hAmylin (19-22) sCT, [$^{13}$Ala $^{14}$Gln] (8-18) hAmylin (19-22) sCT, [$^{13}$Asn $^{14}$Glu $^{15}$Tyr] (8-18) hAmylin (19-27) sCT, [$^{13}$Phe $^{14}$Asp) (8-18) hAmylin (19-27) sCT, [$^{13}$Ala $^{14}$Asp] (8-18) hAmylin [$^{15}$Glu $^{18}$Arg] (8-18) hAmylin (19-24) sCT, [$^{19}$Phe $^{22}$Phe] (19-27) sCT, [$^{13}$Ala $^{14}$Asp] (8-18) hAmylin [$^{19}$Phe $^{20}$His $^{22}$Phe] (19-27) sCT, [$^{13}$Ala $^{14}$Asp] (8-18) hAmylin [$^{19}$Phe $^{22}$Phe] (19-27) sCT, [$^{9}$Thr $^{10}$His] (8-18) hAmylin (19-22) sCT, [$^{9}$Thr $^{10}$His $^{14}$Gly $^{15}$Leu $^{17}$Ser $^{18}$Arg] (8-19) hAmylin (20-23) sCT, (8-18) hAmylin [$^{21}$Asn $^{22}$Phe $^{23}$Val] (19-23) sCT, (8-18) hAmylin [$^{22}$Met] (19-27) sCT, (8-18) hAmylin [$^{22}$Val] (19-27) sCT, [$^{9}$Met $^{12}$Thr $^{13}$Tyr $^{14}$Thr $^{15}$Glu $^{16}$Asp $^{17}$Phe] (8-17) hAmylin [$^{18}$Arg] (18-20) sCT, and the like. In other embodiments, compounds useful in the methods described herein include variations of the above exemplary compounds with the α-helix terminating at a position corresponding to 22, 23, 24, 25, 26 or 27 of sCT. In other words, compound (8-18) hAmylin (19-24) sCT is contemplated as this compound is merely (8-18) hAmylin (19-27) sCT (supra) truncated at position 24.

In certain embodiments, the C-terminal tail of compounds useful in the methods described herein comprises amino acids from position 27, 28, 29, 30, 31, 32, or 33 to position 36 or 37 of hAmylin. In other embodiments, the C-terminal tail comprises amino acids from position 27 or 28 to position 32 of sCT; however, when the loop region is from a calcitonin or calcitonin analog and the α helix region is from a calcitonin or calcitonin analog, the last position of the C-terminal tail is not Pro, Hyp, homoSerine (Hse) or derivatives of Hse. Alternatively or additionally, the above described α helix of amylin and calcitonin may further comprise the substitutions of one or more of [$^{27}$Tyr] hAmylin, [$^{29}$Arg] hAmylin, [$^{32}$Val] hAmylin, [$^{32}$Thr] hAmylin, [$^{34}$Glu] hAmylin, [$^{35}$Lys] hAmylin, [$^{36}$Phe] hAmylin, [$^{36}$Ala] hAmylin, [$^{37}$Phe] hAmylin, [$^{30}$Asn] sCT, [$^{32}$Tyr] sCT, or any combination thereof.

In one embodiment, a C-terminal tail of compounds useful in the methods described herein can be represented by $Xaa_{28}$-$Xaa_{29}$-$Xaa_{30}$-$Xaa_{31}$-$Xaa_{32}$-$Xaa_{33}$-G-$Xaa_{35}$-$Xaa_{36}$-$Xaa_{37}$-$Xaa_{38}$ (SEQ ID NO:33), wherein $Xaa_{28}$ is Lys, Tyr, or absent; $Xaa_{29}$ is Ser, Pro, or absent; $Xaa_{30}$ is Ser, Pro, Arg, or absent; $Xaa_{31}$ is Thr, or absent; $Xaa_{32}$ is Asn or absent; $Xaa_{33}$ is Val, Thr, or absent; $Xaa_{35}$ is Ser, or Glu; $Xaa_{36}$ is Asn, Lys, or Gly; $Xaa_{37}$ is Thr, Phe, or Ala; $Xaa_{38}$ is Tyr, Phe, Pro, or absent; with the optional proviso that when the loop region is from a calcitonin or calcitonin analog and the α helix region is from a calcitonin or calcitonin analog, the last position of the C-terminal tail is not Pro, Hyp, homoSerine (Hse) or derivatives of Hse.

Again, it should be remembered that each member of the Markush group, or a combination thereof, is another embodiment and is not to be read as a single unit. It is further contemplated that the C-terminal tail may contain no more than one, two, or three modifications such as substitutions, insertions, deletions, and/or derivatizations of the compounds described in the previous paragraphs.

Examples of the C-terminal tail of compounds useful in the methods described herein include, but is not limited to, (27-37)rAmylin, [$^{27}$Tyr $^{29}$Arg $^{32}$Thr] (27-37)rAmylin, [$^{29}$Arg $^{32}$Thr] (28-37)rAmylin, (30-37) hAmylin, [$^{32}$Thr] (30-37) hAmylin, [$^{35}$Lys $^{36}$Ala $^{37}$Phe] (30-37) hAmylin, (30-36) hAmylin, [$^{32}$Val] (30-36) hAmylin, [$^{34}$Glu $^{36}$Phe] (30-36) hAmylin, (31-37) hAmylin, (31-36) hAmylin, (33-36) hAmylin, (33-37) hAmylin, (28-32) sCT, [$^{30}$Asn $^{32}$Tyr] (28-32) sCT, and (27-32) sCT. In other embodiments, the C-terminal tail comprises the amino acid sequence KSNFVPTN (SEQ ID NO:34) or SNFVPTNV (SEQ ID NO:35).

It is further contemplated that no more than one, two, or three modifications such as substitutions, insertions, deletions, and/or derivatizations may be made to the C-terminal tail of compounds useful in the methods described herein. The C-terminal tail of the compounds may further comprise modifications or additional amino acids at the C-terminal end. Such modifications include the addition of compounds such as Lys, up to 4 Lys, L-Octylglycine, 4ABU (4-Aminobutyric acid), 9Anc (9-Amiononanoic acid), and/or groups for solubility, stability, or delivery. Examples include (33-37) hAmylin L-octylglycine, (33-37) hAmylin 4ABU, and (33-37) hAmylin 9Anc.

In another embodiments, compounds useful in the methods described herein comprise an amino acid sequence of Formula I: $Xaa_1$-X-$Xaa_3$-$Xaa_4$-$Xaa_5$-$Xaa_6$-Y-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-$Xaa_{18}$-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$Xaa_{27}$-$Xaa_{28}$-$Xaa_{29}$-$Xaa_{30}$-$Xaa_{31}$-$Xaa_{32}$ (SEQ ID NO:36); wherein $Xaa_1$ is A, C, hC, D, E, F, I, L, K, hK, R, hR, S, Hse(homoSER), T, G, Q, N, M, Y, W, P, Hyp(hydroxyProline), H, V or absent; $Xaa_3$ is A, D, E, N, Q, G, V, R, K, hK, hR, H, I, L, M, or absent; $Xaa_4$ is A, I, L, S, Hse, T, V, M, or absent; $Xaa_5$ is A, S, T, Hse, Y, V, I, L, or M; $Xaa_6$ is T, A, S, Hse, Y, V, I, L, or M; $Xaa_8$ is A, V, I, L, F, or M; $Xaa_9$ is L, T, S, Hse, V, I, or M; $Xaa_{10}$ is G, H, Q, K, R, N, hK, or hR; $Xaa_{11}$ is K, R, Q, N, hK, hR, or H; $Xaa_{12}$ is L, I, V, F, M, W, or Y; $Xaa_{13}$ is A, F, Y, N, Q, S, Hse, or T; $Xaa_{14}$ is A, D, E, G, N, K, Q, R, H, hR, or hK; $Xaa_{15}$ is A, D, E, F, L, S, Y, I, V, or M; $Xaa_{16}$ is L, F, M, V, Y, or I; $Xaa_{17}$ is H, Q, N, S, Hse, T, or V; $Xaa_{18}$ is K, hK, R, hR, H, Cit or Orn; $Xaa_{19}$ is F, L, S, Hse, V, I, T, or absent; $Xaa_{20}$ is H, R, K, hR, hK, N, Q, or absent; $Xaa_{21}$ is T, S, Hse, V, I, L, Q, N, or absent; $Xaa_{22}$ is F, L, M, V, Y, or I; $Xaa_{23}$ is P or Hyp; $Xaa_{24}$ is P, Hyp, R, K, hR, hK, or H; $Xaa_{25}$ is T, S, Hse, V, I, L, F, or Y; $Xaa_{26}$ is N, Q, D, or E; $Xaa_{27}$ is T, V, S, F, I, or L; $Xaa_{28}$ is G or A; $Xaa_{29}$ is S, Hse, T, V, I, L, or Y; $Xaa_{30}$ is E, G, K, N, D, R, hR, hK, H, or Q; $Xaa_{31}$ is A, T, S, Hse, V, I, L, F, or Y; and $Xaa_{32}$ is F, P, Y, Hse, S, T, or Hyp; wherein X and Y are capable of creating a bond and are independently selected residues having side chains which are chemically bonded to each other to form an intramolecular linkage such as disulfide bonds; amide bond; alkyl acids and alkyl amines which may form cyclic lactams; alkyl aldehydes or alkyl halides and alkylamines which may condensed and be reduced to form an alkyl amine or imine bridge; or side chains which may be connected to form an alkyl, alkenyl, alkynyl, ether or thioether bond. Alkyl chains may include lower alkyl groups having from about 1 to about 6 carbon atoms. In certain embodiments, the intramolecular linkage may be a disulfide, amide, imine, amine, alkyl and alkene bond. In certain embodiments, X and Y are independently selected from Ser, Asp, Glu, Lys, Orn, or Cys. In certain embodiments, X and Y are Cys and Cys. In other embodiments, X and Y are Ser and Ser. In still other embodiments, X and Y are Asp and Lys or Lys and Asp.

In other embodiments, compounds useful in the methods described herein comprise an amino acid sequence of Formula II: $Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-$Xaa_{18}$-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$Xaa_{27}$-$Xaa_{28}$-$Xaa_{29}$-$Xaa_{30}$-$Xaa_{31}$-$Xaa_{32}$ (SEQ ID NO:37); wherein $Xaa_1$ is A, C, D, F, I, K, S, T, or absent; $Xaa_2$ is C, D, S, or absent; $Xaa_3$ is A, D, N, or absent; $Xaa_4$ is A, L, T, or absent; $Xaa_5$ is A or S; $Xaa_6$ is T, A, S, or V; $Xaa_7$ is C, K, or A; $Xaa_8$ is A, V, L, or M; $Xaa_9$ is L or T; $Xaa_{10}$ is G, H, or Q; $Xaa_{11}$ is K, R, Q, or hArg; $Xaa_{12}$ is L, W, or Y; $Xaa_{13}$ is A, F, N, Q, S, or T; $Xaa_{14}$ is A, D, E, G, N, K, Q, or R; $Xaa_{15}$ is A, D, E, F, L, S, or Y; $Xaa_{16}$ is L, or F; $Xaa_{17}$ is H, Q, S, or V; $Xaa_{18}$ is K, R, hArg, Cit or Orn; $Xaa_{19}$ is F, L, S, or absent; $Xaa_{20}$ is H, Q, or absent; $Xaa_{21}$ is T, N, or absent; $Xaa_{22}$ is F, L, M, V, or Y; $Xaa_{23}$ is P; $Xaa_{24}$ is P or R; $Xaa_{25}$ is T; $Xaa_{26}$ is N; $Xaa_{27}$ is T or V; $Xaa_{28}$ is G; $Xaa_{29}$ is S; $Xaa_{30}$ is E, G, K, or N; $Xaa_{31}$ is A or T; and $Xaa_{32}$ is F, P, or Y.

In yet other embodiments, compounds useful in the methods described herein comprise an amino acid sequence of Formula III: $Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-$Xaa_{18}$-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$Xaa_{27}$-$Xaa_{28}$-$Xaa_{29}$-$Xaa_{30}$-$Xaa_{31}$-$Xaa_{32}$ (SEQ ID NO:38); wherein $Xaa_1$ is A, C, F, I, K, S, or absent; $Xaa_2$ is C, D, or S; $Xaa_3$ is A, D or N; $Xaa_4$ is A, L or T; $Xaa_5$ is A or S; $Xaa_6$ is T; $Xaa_7$ is C or K; $Xaa_8$ is A or V; $Xaa_9$ is L or T; $Xaa_{10}$ is G, H, or Q; $Xaa_{11}$ is K, R, or hArg; $Xaa_{12}$ is L; $Xaa_{13}$ is A, F, N, S, or T; $Xaa_{14}$ is A, D, E, G, N, Q, or R; $Xaa_{15}$ is A, E, F, L, S, or Y; $Xaa_{16}$ is L; $Xaa_{17}$ is H, S, or V; $Xaa_{18}$ is K, R, hArg, Cit or Orn; $Xaa_{19}$ is F, L, or S; $Xaa_{20}$ is H or Q; $Xaa_{21}$ is T or N; $Xaa_{22}$ is F, L, M, V, or Y; $Xaa_{23}$ is P; $Xaa_{24}$ is P or R; $Xaa_{25}$ is T; $Xaa_{26}$ is N; $Xaa_{27}$ is T, or V; $Xaa_{28}$ is G; $Xaa_{29}$ is S; $Xaa_{30}$ is E, G, K, or N; $Xaa_{31}$ is A, or T; and $Xaa_{32}$ is F, P, or Y.

In further embodiments, the sequence of formula I, II, or III further include 1, 2, 3, 4, 5, 6, 7, 8, 9, 10, 11, 12, or more modifications of substitutions, insertions, deletions, elongations and/or derivatizations. In certain embodiments, the sequence of Formulae I, II, or III comprises a Val is inserted between amino acids at positions 22 and 23. In other embodiments, the sequence of Formulae I, II, or II comprises a Gln is inserted between positions 22 and 23. In still other embodiments, the sequence of Formulae I, II, or III comprises a sequence of Gln-Thr-Tyr between positions 22 and 23. In yet other embodiments, the sequence of Formulae I, II, or III comprises a sequence of Leu-Gln-Thr-Tyr (SEQ ID NO:39) between positions 22 and 23. In other embodiments, the modifications of Formulae I, II, or III may be at the N-terminal end. In certain embodiments, the N-terminal portion of Formulae I, II, or III has an added octylglycine. In other embodiments, the N-terminal portion of Formulae I, II or III has an added isocap.

In yet other embodiments, compounds useful in the methods described herein comprise an amino acid sequence of Formula IV: $Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-$Xaa_{15}$-$Xaa_{16}$-$Xaa_{17}$-$Xaa_{18}$-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$Xaa_{27}$-$Xaa_{28}$-$Xaa_{29}$-$Xaa_{30}$-$Xaa_{31}$-$Xaa_{32}$ (SEQ ID NO:40); wherein $Xaa_1$ is A, C, D, F, K, T, or absent; $Xaa_2$ is A, C, D, S, or absent; $Xaa_3$ is A, D, N, or absent; $Xaa_4$ is A, L, T, or absent; $Xaa_5$ is A or S; $Xaa_6$ is A, S, T, or V; $Xaa_7$ is A, C, or K; $Xaa_8$ is A, L, M, or V; $Xaa_9$ is L or T; $Xaa_{10}$ is G, H, or Q; $Xaa_{11}$ is K, Q, or R; $Xaa_{12}$ is L, W, or Y; $Xaa_{13}$ is A, N, Q, S, or T; $Xaa_{14}$ is A, D, E, G, K, N, Q, or R; $Xaa_{15}$ is A, D, E, F, L, S, or Y; $Xaa_{16}$ is F or L; $Xaa_{17}$ is H, Q, S or V; $Xaa_{18}$ is K, or R; $Xaa_{19}$ is F, L, S, or absent; $Xaa_{20}$ is H, K, Q, or absent; $Xaa_{21}$ is Q, T, or absent; $Xaa_{22}$ is F, L, or Y; $Xaa_{23}$ is P; $Xaa_{24}$ is P or R; $Xaa_{25}$ is T; $Xaa_{26}$ is N; $Xaa_{27}$ is T or V; $Xaa_{28}$ is G; $Xaa_{29}$ is S; $Xaa_{30}$ is E, K or N; $Xaa_{31}$ is A or T; and $Xaa_{32}$ is F, Y, or absent.

In some embodiments, the sequence of Formula IV further comprises 1, 2, 3, 4, 5, 6, 7, 8, 9, 10, 11, 12, or more modifications of substitutions, insertions, deletions, elongations and/or derivatizations. In certain embodiments, the sequence of formula I, II, III, or IV comprises a deletion at position 24.

In some embodiments, compounds useful in the methods described herein comprise (a) any of the loop region sequences described herein; (b) any α helix region described herein; and (c) any C-terminal tail described herein, with the optional proviso that when the loop region is from a calcitonin or calcitonin analog and the α helix region is from a calcitonin or calcitonin analog, the last position of the C-terminal tail is not Pro, Hyp, homoSerine (Hse) or derivatives of Hse.

In other embodiments, compounds useful in the methods described herein comprise (a) a loop region comprising X-"XY linker sequence"-Y (SEQ ID NO:6) with optional modifications at the N-terminal end as provided herein; (b) an α helix region comprising the α helix region type I or type II; (c) a C-terminal tail represented by SEQ ID NO:33, with the optional proviso that when the loop region is from a calcitonin or calcitonin analog and the α helix region is from a calcitonin or calcitonin analog, the last position of the C-terminal tail is not Pro, Hyp, homoSerine (Hse) or derivatives of Hse. The C-terminal end may comprise further modifications.

In yet other embodiments, compounds useful in the methods described herein comprise an amino acid sequence comprising: a) a loop region comprising X-"XY-linker sequence"-Y; b) an α helix loop type I; and c) a C-terminal tail; wherein X-"XY-linker sequence"-Y comprises an amino sequence X-$Xaa_2$-$Xaa_3$-$Xaa_4$-$Xaa_5$-$Xaa_6$-$Xaa_7$-Y (SEQ ID NO:6) wherein, $Xaa_2$ is any amino acid or absent; $Xaa_3$ is Ala, Gly, Ser, Asp or absent; $Xaa_4$ is Asn, Ala, Asp, Gly or absent; $Xaa_5$ is Ala, Leu, Thr, or Ser; $Xaa_6$ is Ala, Ser, or Thr; and $Xaa_7$ is Ala, Ser, Val, Hse, (S)-2-amio-3-hydroxy-methylbutanoic acid (Ahb), (2S,3R)-2-amino-3-hydroxy-methylpentanoic acid (Ahp), D-Thr, Thr, or a derivative thereof; X and Y are amino acids capable of creating a bond and are independently selected residues having side chains which are chemically bonded to each other to form an intramolecular linkage such as disulfide bonds; amide bond; alkyl acids and alkyl amines which may form cyclic lactams; alkyl aldehydes or alkyl halides and alkylamines which may condensed and be reduced to form an alkyl amine or imine bridge; or side chains which may be connected to form an alkyl, alkenyl, alkynyl, ether or thioether bond; the α helical region type I comprises the sequence $R_1$-V-L-$Xaa_{10}$-$Xaa_{11}$-LSQ-$Xaa_{15}$-L-$Xaa_{17}$-$Xaa_{18}$-LQT-$Xaa_{22}$-P-$Xaa_{24}$-TNT-$R_1$ (SEQ ID NO:31), wherein $Xaa_{10}$ is Gly or Aib; $Xaa_1$ is Lys, Arg, Orn, hArg, Cit, hLys, or Lys(for); $Xaa_{15}$ is Glu or Phe; $Xaa_{17}$ is His or Aib; $Xaa_{18}$ is Lys, Arg, Orn, hArg, Cit, hLys, Lys(for), Lys(PEG 5000); $Xaa_{22}$ is Try or Leu; $Xaa_{24}$ is Arg or Pro; or $R_1$ is absent or comprises 1-4 additional amino acids; and the C-terminal tail comprises the sequence $Xaa_{28}$-$Xaa_{29}$-$Xaa_{30}$-$Xaa_{31}$-$Xaa_{32}$-$Xaa_{33}$-G-$Xaa_{35}$-$Xaa_{36}$-$Xaa_{37}$-$Xaa_{38}$ (SEQ ID NO:33), wherein $Xaa_{28}$ is Lys, Tyr, or absent; $Xaa_{29}$ is Ser, Pro, or absent; $Xaa_{30}$ is Ser, Pro, Arg, or absent; $Xaa_{31}$ is Thr, or absent; $Xaa_{32}$ is Asn or absent; $Xaa_{33}$ is Val, Thr, or absent; $Xaa_{35}$ is Ser, or Glu; $Xaa_{36}$ is Asn, Lys, or Gly; $Xaa_{37}$ is Thr, Phe, or Ala; $Xaa_{38}$ is Tyr, Phe, Pro, or absent; with the optional proviso that when the loop region is from a calcitonin or calcitonin analog and the α helix region is from a calcitonin or calcitonin analog, the last position of the C-terminal tail is not Pro, Hyp, homoSerine (Hse) or derivatives of Hse.

In yet other embodiments, compounds useful in the methods described herein comprise an amino acid sequence comprising a) a loop region comprising X-"XY-linker sequence"-Y (SEQ ID NO:6); b) an α helix loop type II; and c) a C-terminal tail; wherein the loop region comprising X-"XY-linker sequence"-Y comprises an amino sequence of X $Xaa_2$ $Xaa_3$ $Xaa_4$ $Xaa_5$ $Xaa_6$ $Xaa_7$ Y wherein, $Xaa_2$ is any amino acid or absent; $Xaa_3$ is Ala, Gly, Ser, Asp or absent; $Xaa_4$ is Asn, Ala, Asp, Gly or absent; $Xaa_5$ is Ala, Leu, Thr, or Ser; $Xaa_6$ is Ala, Ser, or Thr; and $Xaa_7$ is Ala, Ser, Val, Hse, (S)-2-amio-3-hydroxy-methylbutanoic acid (Ahb), (2S,3R)-2-amino-3hydroxy-methylpentanoic acid (Ahp), D-Thr, Thr, or a derivative thereof; X and Y are amino acids capable of creating a bond and are independently selected residues having side chains which are chemically bonded to each other to form an intramolecular linkage such as disulfide bonds; amide bond; alkyl acids and alkyl amines which may form cyclic lactams; alkyl aldehydes or alkyl halides and alkylamines which may condensed and be reduced to form an alkyl amine or imine bridge; or side chains which may be connected to form an alkyl, alkenyl, alkynyl, ether or thioether bond; the α helical region type II comprises the sequence $R_1$-$Xaa_8$-$Xaa_9$-$Xaa_{10}$-R-$Xaa_{12}$-$Xaa_{13}$-$Xaa_{14}$-$Xaa_{15}$-$Xaa_{16}$-$Xaa_{17}$-$Xaa_{18}$-$Xaa_{19}$-$Xaa_{20}$-$Xaa_{21}$-$Xaa_{22}$-P-$Xaa_{24}$-TNT-$R_1$ (SEQ ID NO:32) wherein $Xaa_8$ is Ala or Val; $Xaa_9$ is Thr, Met or Leu; $Xaa_{10}$ is Gln, Gly, His; $Xaa_{12}$ is Leu, or Thr; $Xaa_{13}$ is Ala, Thr, Asn, Phe, Tyr, Ser, or Thr; $Xaa_{14}$ is Asn, Arg, Ala, Asp, Glu, Gln, Thr, or Gly; $Xaa_{15}$ is Phe, Leu, Ser, Glu, Ala, Asp, or Tyr; $Xaa_{16}$ is Leu or Asp; $Xaa_{17}$ is Val, His, Ser, Phe, or Aib; $Xaa_{18}$ is His, Arg, Lys, Orn, hArg, Cit, hLys, Lys(for), or Lys(PEG5000); $Xaa_{19}$ is Leu, Ser or Phe; $Xaa_{20}$ is Gln or His; $Xaa_{21}$ is Thr or Asn; $Xaa_{22}$ is Tyr, Val, Phe, Leu or Met; $Xaa_{24}$ is Arg or Pro; and $R_1$ is absent or comprises 1-4 additional amino acids; and the C-terminal tail comprises the sequence $Xaa_{28}$-$Xaa_{29}$-$Xaa_{30}$-$Xaa_{31}$-$Xaa_{32}$-$Xaa_{33}$-G-$Xaa_{35}$-$Xaa_{36}$-$Xaa_{37}$-$Xaa_{38}$ (SEQ ID NO:33), wherein $Xaa_{28}$ is Lys, Tyr, or absent; $Xaa_{29}$ is Ser, Pro, or absent; $Xaa_{30}$ is Ser, Pro, Arg, or absent; $Xaa_{31}$ is Thr, or absent; $Xaa_{32}$ is Asn or absent; $Xaa_{33}$ is Val, Thr, or absent; $Xaa_{35}$ is Ser, Glu; $Xaa_{36}$ is Asn, Lys, or Gly; $Xaa_{37}$ is Thr, Phe, or Ala; $Xaa_{38}$ is Tyr, Phe, Pro, or absent.

In yet other embodiments, compounds useful in the methods described herein include:

KCNTATCVLGKLSQELHRLQTYPRTNTGSNTY SEQ ID NO: 41

KCNTATCVLGRLSQELHRLQTLPRTNTGSNTY SEQ ID NO: 42

KCNTATCVLGRLSQELHRLQTYPPTNTGSNTY SEQ ID NO: 43

KCNTATCVLGRLSQELHRLQTYPRTNVGSNTY SEQ ID NO: 44

KCNTATCVLGRLSQELHRLQTLPPTNVGSNTY SEQ ID NO: 45

KCNTATCVLGRLANFLHRLQTYPRTNTGSNTY SEQ ID NO: 46

ACNTATCVLGRLSQELHRLQTYPRTNTGSNTY SEQ ID NO: 47

KCNAATCVLGRLSQELHRLQTYPRTNTGSNTY SEQ ID NO: 48

KCNTAACVLGRLSQELHRLQTYPRTNTGSNTY SEQ ID NO: 49

CANLSTCVLGRLSQELHRLQTYPRTNTGSNTY SEQ ID NO: 50 isocaproyl-STAVLGRLSQELHRLQTYPRTNTGSNTY SEQ ID NO: 51

CSNASTCVLGRLSQELHRLQTYPRTNTGSNTY SEQ ID NO: 52

CSNLATCVLGRLSQELHRLQTYPRTNTGSNTY SEQ ID NO: 53

CSNLSACVLGRLSQELHRLQTYPRTNTGSNTY SEQ ID NO: 54

KCNTATCVLGRLSQELHRLQTYPRTNTGSNTY SEQ ID NO: 55

KCNTATCVLGRLSQELHRLQTYPRTNTGSGTP SEQ ID NO: 56

CSALSTCVLGRLSQELHRLQTYPRTNTGSNTY SEQ ID NO: 57

Ac-(Agy)SNLST(Agy)VLGRLSQELHRLQTYPRTNTGSNTY SEQ ID NO: 58

Ac-K(Agy)NTAT(Agy)VLGRLSQELHRLQTYPRTNTGSNTY SEQ ID NO: 59

Isocaproyl-STAVL(Aib)RLSQELRLQTYPRTNTGSGTP SEQ ID NO: 60

Isocaproyl-STAVLG[K(For)]LSQELH[K(For)]LQTYPRTNTGSGTP SEQ ID NO: 61

Isocaproyl-STAVL(Aib)[K(For)]LSQEL(Aib)[K(For)]LQTYPRTNTGSNTY SEQ ID NO: 62

Isocaproyl-STAVL(Aib)[K(For)]LSQEL(Aib)[K(For)]LQTYPRTNVGSNTY SEQ ID NO: 63

KCNTATCLLQQLQKLLQKLKQYPRTNTGSNTY SEQ ID NO: 64

KCNTASCVLGRLSQELHRLQTYPRINTGSNTY SEQ ID NO: 65

-continued

SEQ ID NO: 66
KCNTAVCVLGRLSQELHRLQTYPRTNTGSNTY

SEQ ID NO: 67
KCNTATCVLGRLSQELHRYPRTNTGSNTY

SEQ ID NO: 68
KCNTATCVLGK(For)LSQELHK(For)LQTYPRTNTGSNTY

SEQ ID NO: 69
KCNTA(d-Thr)CVLGRLSQELHRLQTYPRTNTGSNTY

SEQ ID NO: 70
KCNTA(dAh)CVLGRLSQELHRLQTYPRTNTGSNTY

SEQ ID NO: 71
Ac-ACNTATCVLGRLSQELHK(PEG5000)LQTYPRTNTGSNTY

SEQ ID NO: 72
KCNTATCVLGRLSQELHRLQTLQTYPRTNTGSNTY

SEQ ID NO: 73
KCNTATCVLGRLSQELHRLQTLLQTYPRINTGSNTY

SEQ ID NO: 74
KCNTATCVLGKLSQELHKLQTYPRTNTGSNTY

SEQ ID NO: 75
KCNTSTCVLGRLSQELHRLQTYPRTNTGSNTY

SEQ ID NO: 76
KCNTATCATQRLSQELHRLQTYPRTNTGSNTY

SEQ ID NO: 77
KCNTATCATQRLSQELHRLQTYPRTNVGSNTY

SEQ ID NO: 78
KCNTSTCATQRLANELVRLQTYPRTNVGSNTY

SEQ ID NO: 79
KCNTA(Hse)CVLGRLSQELHRLQTYPRTNTGSNTY

SEQ ID NO: 80
KCNTA(Ahb)CVLGRLSQELHRLQTYPRTNTGSNTY

SEQ ID NO: 81
KCNTA(Ahp)CVLGRLSQELHRLQTYPRTNTGSNTY

SEQ ID NO: 82
KCNTAT(OPO3H2)CVLGRLSQELHRLQTYPRTNTGSNTY

SEQ ID NO: 83
KCNTATCVLG(Orn)LSQELH(Orn)LQTYPRTNTGSNTY

SEQ ID NO: 84
KCNTATCVLG(Cit)LSQELH(Cit)LQTYPRTNTGSNTY

SEQ ID NO: 85
KCNTATCVLG(homoK)LSQELH(homoK)LQTYPRTNTGSNTY

SEQ ID NO: 86
L-OctylglycineKCNTATCVLGRLSQELHRLQTYPRINTGSNTY

SEQ ID NO: 87
N-3,6-dioxaoctanoyl-CNTATCVLGRLSQELHRLQTVPRINTGSNT
Y

SEQ ID NO: 88
KCNTATCMLGRYTQDFHRLQTYPRTNTGSNTY

SEQ ID NO: 89
DSNLSTKVLGRLSQELHRLQTYPRTNTGSNTY

SEQ ID NO: 90
KDNTATKVLGRLSQELHRLQTYPRTNTGSNTY

SEQ ID NO: 91
CNTATCVLGRLSQELHRLQTYPRTNTGSNTY

-continued

SEQ ID NO: 92
KCNTATCVLGRLSQELHRLQTYPRTNTGSNTY(9Anc)

SEQ ID NO: 93
KCNTATCVLGRLSQELHRLQTYPRTNTGSNTY(L-octylglycine)

SEQ ID NO: 94
N-isocaproyl-KCNTATCVLGRLSQELHRLQTYPRTNTGSNTY

SEQ ID NO: 95
KCNTATCVLG(homoR)LSQELH(homoR)LQTYPRTNTGSNTY

SEQ ID NO: 96
FCNTATCVLGRLSQELHRLQTYPRTNTGSNTY

SEQ ID NO: 97
KCNTATCVLGRLSQELH(Cit)LQTYPRTNTGSNTY

SEQ ID NO: 98
KCNTATCVLGRLSQELH(Orn)LQTYPRTNTGSNTY

SEQ ID NO: 99
ICNTATCVLGRLSQELHRLQTYPRTNTGSNTY

SEQ ID NO: 100
1-Octylglycine-CNTATCVLGRLSQELHRLQTYPRTNTGSNTY

SEQ ID NO: 101
Isocaproyl-CNTATCVLGRLSQELHRLQTYPRTNTGSNTY

SEQ ID NO: 102
KCNTATCVLG(Cit)LSQELHRLQTYPRTNTGSNTY

SEQ ID NO: 103
KCNTATCVLGRLSQELHRLQTYPRTNTGSNTY(4ABU)

SEQ ID NO: 104
Isocaproyl-KCNTATCVLGRLSQELHRLQTYPRTNTGSNTY(4ABU)

SEQ ID NO: 105
KCNTSTCATQRLANELVRLQTYPRTNVGSEAF

SEQ ID NO: 106
KCNTATCVLGRLSQELHRLQTYPTNVGSEAF

SEQ ID NO: 107
KCNTATCVLGRLSRSLHRLQTYPRTNTGSNTY

SEQ ID NO: 108
KCNTATCVTHRLSQELHRLQTYPRTNTGSNTY

SEQ ID NO: 109
KCNTATCVLGRLADFLHRLQTYPRTNTGSNTY

SEQ ID NO: 110
CNTATCVLGRLSQELHRLQTYPRTNTGSNT

SEQ ID NO: 111
KCNTATCVLGRLSQELHRLQNFVPRTNTGSNTY

SEQ ID NO: 112
KCNTATCVLGRLSQELHRLQTYPRTNTGSETF

SEQ ID NO: 113
ACDTATCVLGRLSQELHRLQTYPRTNTGSNTY

SEQ ID NO: 114
KCNTATCVLGRLSQELHRLQTYPRTNTGSKAF

SEQ ID NO: 115
KCDTATCVTHRLAGLLSRSQTYPRTNTGSNTY

SEQ ID NO: 116
KCNTATCVLGRLADALHRLQTYPRTNTGSNTY

SEQ ID NO: 117
KCNTATCVLGRLAAFLHRLQTYPRTNTGSNTY

SEQ ID NO: 118
SCNTATCVLGRLADFLHRLQTYPRTNTGSNTY

KCNTATCVLGRLSQELHRLQTMPRTNTGSNTY  SEQ ID NO: 119

KCNTATCVLGRLSQELHRLQTVPRTNTGSNTY  SEQ ID NO: 120

KCNTATCVLGRLNEYLHRLQTYPRTNTGSNTY  SEQ ID NO: 121

SCNTATCVLGRLSQELHRLQTYPRTNTGSNTY  SEQ ID NO: 122

KCNTATCVLGRLTEFLHRLQTYPRTNTGSNTY  SEQ ID NO: 123

KCNTATCVLGRLAEFLHRLQTYPRTNTGSNTY  SEQ ID NO: 124

KCNTATCVLGRLTDYLHRLQTYPRTNTGSNTY  SEQ ID NO: 125

KCNTATCVLGRLAQFLHRLQTYPRTNTGSNTY  SEQ ID NO: 126

KCNTATCVLGRLADFLHRFQTFPRTNTGSNTY  SEQ ID NO: 127

KCNTATCVLGRLADFLHRFHTFPRTNTGSNTY  SEQ ID NO: 128

KCNTATCVLGRLADFLHRFQTFPRTNTGSGTP  SEQ ID NO: 129

CNTATCVLGRLADFLHRLQTYPRTNTGSNTY  SEQ ID NO: 130

KCDTATCVLGRLSQELHRLQTYPRTNTGSNTY  SEQ ID NO: 131

KCNTATCVLGRLFDFLHRLQTYPRTNTGSNTY  SEQ ID NO: 132

KCNTATCVLGRLAAALHRLQTYPRTNTGSNTY  SEQ ID NO: 133

TCDTATCVLGRLSQELHRLQTYPRTNTGSNTY  SEQ ID NO: 134

CSNLSTCATQRLANELVRLQTYPRTNVGSNTY  SEQ ID NO: 135

KCNTATCATQRLANELVRLQTYPRTNVGSNTY  SEQ ID NO: 136

CSNLSTCVLGRLSQELHRLQTYPRTNTGSNTY  SEQ ID NO: 137

KCNTATCVLGRLSQELHRLQTYPRTNTGSNTY (davalintide)  SEQ ID NO: 138

KCNTATCATQRLANFLVRSSNNLTNVGSNTY  SEQ ID NO: 139

KCNTATCATQRLANALVHSSNNFGAILPSTNVGSNTY  SEQ ID NO: 140

KCNTATCATARLAAFLARSSGY  SEQ ID NO: 141

KCNTATCATQRLANFLVHSGNNFGAILSSTNVGSNTY  SEQ ID NO: 142

CNTATCATARLAAFLARS  SEQ ID NO: 143

KCATATCVLGRLSQELHRLQTYPRTNTGSNTY  SEQ ID NO: 144

KCNTATCATQRLSQELHRLQTYPRTNTGSGTP  SEQ ID NO: 145

In further embodiments, an analog of each parent compound as specified above contains no more than 1, 2, 3, 4, 5, 6 or 7 total number of modifications, alone or in combination, compared to the parent compound, where the "modification" includes substitutions, insertions, elongations deletions, and derivatizations. In further embodiments, an analog of a parent compound as specified above is at least 80%, 85%, 90%, 92%, 95%, or 100% identical to the parent compound. It is understood that with reference to all peptide sequences provided herein, for example without limitation the peptides sequences of SEQ ID NO:41 to 145, if a side chain to side chain bridge can be formed, for example without limitation disulfide, then both the linear and bridged compounds are contemplated herein. For example without limitation, for the peptide having SEQ ID NO:138, both the linear and cyclo ($^2$Cys-$^7$Cys) peptides are contemplated. Further to any peptide sequence provided herein, for example without limitation the peptides sequences of SEQ ID NO:41 to 145, such sequences are understood to include C-terminal modifications as described herein, if such C-terminal modification is available. For example without limitation, for the peptide having SEQ ID NO:138 is understood to contemplate the free acid, the amide (—$CONH_2$), and other C-terminally modified sequences as described herein and as known in the art. In further embodiments, an analog of each parent compound of SEQ ID NOS:41 to 145 contains no more than 1, 2, 3, 4, 5, 6 or 7 total number of modifications, alone or in combination, compared to the parent compound, where the "modification" includes substitutions, insertions, elongations deletions, and derivatizations. In further embodiments, an analog of SEQ ID NOS:41 to 145 is at least 80%, 85%, 90%, 92%, or 95% identical to the parent compound.

In still other embodiments, compounds useful in the methods described herein include biologically active fragments of SEQ ID NOS:41 to 145. Biologically active fragments may comprise deletions of 1, 2, 3, 4, 5, 6, 7, 8, 9, 10, 11, 12, 13, 14, 15 or more amino acids. In certain embodiments, the amino acid sequences of SEQ ID NOs:41 to 145 comprise at least 1, 2, 3, 4, 5, 6, 7, 8, 9, 10 or more modifications such as substitutions, insertions, deletions, and/or derivatizations. In other embodiments, the amino acid sequences of SEQ ID NOS:41 to 145 has no more than 1, 2, 3, 4, 5, 6, 7, 8, 9, or 10 modifications such as substitutions, insertions, deletions, and/or derivatizations. In some embodiments, compounds useful in the methods described herein include those having at least 75, 80, 85, 87, 90, 92, 95, or 100% amino acid sequence identity to any of SEQ ID NOS:41 to 145. Percent identity is determined by methods known the art, for example without limitation by analysis with the AlignX module in Vector NTI (Invitrogen; Carlsbad Calif.). It is intended that each percent identity described, or reference to biologically active fragments or modifications be applied to each sequence identifier individually.

Compounds useful in the methods described herein can form salts with various inorganic and organic acids and bases, which salts are further contemplated for use herein. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid, and camphorsulfonic acid. Salts prepared with bases include, for example, ammonium salts, alkali metal salts (such as sodium and potassium salts), and alkali earth salts (such as calcium and magnesium salts). Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin. The above-described amylin agonist analogs include various stereoisomers. In the preferred amylin agonist analogs, the chiral centers on the peptide backbone are all S.

The nomenclature of various amylin agonist analogue compounds useful in the methods described herein can be used to indicate both the peptide that the sequence is based on and the modifications made to any basic peptide amylin sequence, such as human amylin. An amino acid preceded by a superscript number indicates that the named amino acid replaces the amino acid normally present at the amino acid position of the superscript in the basic amino acid sequence. For example, "[$^{18}$Arg$^{25,28}$Pro]-h-amylin" refers to a peptide based on the sequence of "h-amylin" or "human-amylin" having the following substitutions: Arg replacing His at residue 18, Pro replacing Ala at residue 25 and Pro replacing Ser at residue 28. The term "des-$^{1}$Lys-h-amylin refers to a peptide based on the sequence of human amylin, with the first, or N-terminal, amino acid deleted.

The agonist analogs of amylin useful in the methods described herein are useful in view of their pharmacological properties. Activity as amylin agonist agents can be indicated by activity in the receptor binding assay and the soleus muscle assay described below. Amylin agonist activity of compounds may also be assessed by the ability to modify body composition as described herein.

The activity of amylin agonists may be evaluated using certain biological assays described herein. The receptor binding assay can identify both candidate amylin agonists and antagonists and can be used to evaluate binding, while the soleus muscle assay distinguishes between amylin agonists and antagonists. Effects of amylins or amylin agonists on metabolism can be identified, evaluated, or screened for using the methods described in the Examples below, or other art-known or equivalent methods for determining metabolism.

Preferably, agonist compounds exhibit activity in the receptor binding assay on the order of less than about 1 to 5 nM, preferably less than about 1 nM and more preferably less than about 50 pM. In the soleus muscle assay these compounds preferably show $EC_{50}$ values on the order of less than about 1 to 10 micromolar.

The receptor binding assay is described in U.S. Pat. No. 5,264,372, the disclosure of which is incorporated herein by reference. The receptor binding assay is a competition assay which measures the ability of compounds to bind specifically to membrane-bound amylin receptors. A preferred source of the membrane preparations used in the assay is the basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand are analyzed by computer, using analyses by nonlinear regression to a 4-parameter logistic equation (Inplot program; GraphPAD Software, San Diego, Calif.) or the ALLFIT program of DeLean et al. (ALLFIT, Version 2.7 (NIH, Bethesda, Md. 20892)). Munson, P. and Rodbard, D., *Anal. Biochem.* 107:220-239 (1980).

Assays of biological activity of amylin agonists, including amylin agonist analogue preparations in the soleus muscle are performed using previously described methods (Leighton, B. and Cooper, G. J. S., *Nature*, 335:632-635 (1988); Cooper, G. J. S., et al., *Proc. Natl. Acad. Sci. USA* 85:7763-7766 (1988)). In summary, amylin agonist activity is assessed by measuring the inhibition of insulin-stimulated glycogen synthesis in soleus muscle. Amylin antagonist activity is assessed by measuring the resumption of insulin-stimulated glycogen synthesis in the presence of 100 nM rat amylin and an amylin antagonist. Concentrations of peptide dissolved in carrier-free buffers are determined by quantitative amino acid analysis, as described therein. The ability of compounds to act as agonists in this assay is determined by measuring $EC_{50}$ values. Standard errors are determined by fitting of sigmoidal dose response curves using a four parameter logistic equation (De Lean, A., Munson, P. J., Guardabasso, V. and Rodbard, D. (1988) *ALLFIT*, Version 2.7, National Institute of Child Health and Human Development, N.I.H. Bethesda, Md., 1 diskette). A number of amylin agonists have been characterized using these biological assays. The compounds $^{18}$Arg$^{25,}$ $_{28}$Pro-h-amylin, des$^{1}$Lys$^{18}$Arg$^{25,28}$Pro-h-amylin, $^{18}$Arg$^{25,28,}$ $_{29}$Pro-h-amylin, des$^{1}$Lys$^{18}$Arg$^{25,28,29}$Pro-h-amylin, $^{25,28,}$ $_{29}$Pro-h-amylin, des-$^{1}$Lys$^{25,28,29}$Pro-h-amylin, and $^{25}$Pro$^{26}$Val$^{25,28}$Pro-h-amylin were all found to compete with amylin in the receptor binding assay. These compounds have negligible antagonist activity as measured by the soleus muscle assay and were shown to act as amylin agonists. Similar results were obtained with other agonist compounds listed above.

Compounds such as those described above are prepared using standard solid-phase peptide synthesis techniques and preferably an automated or semiautomated peptide synthesizer. Typically, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer were purchased from Applied Biosystems Inc. (Foster City, Calif.), unless otherwise indicated. The side-chain protected amino acids used and purchased from Applied Biosystem, Inc. included the following: Boc-Arg(ts), Fmoc-Arg(Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl-Z), Fmoc-Lys (Boc), Boc-Glu(Bzl), Fmoc-Glu(t-Bu), Fmoc-His(Trt), Fmoc-Asn(Trt), and Fmoc-Gln(Trt). Boc-His(BOM) was purchased from Applied Biosystems, Inc. or Bachem Inc. (Torrance, Calif.). Anisole, methylsulfide, phenol, ethanedithiol, and thioanisole were obtained from Aldrich Chemical Company (Milwaukee, Wis.). Air Products and Chemicals (Allentown, Pa.) supplied HF. Ethyl ether, acetic acid and methanol were purchased from Fisher Scientific (Pittsburgh, Pa.).

Solid phase peptide synthesis was carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Boc-peptide-resins were cleaved with HF (−5° C. to 0° C., 1 hour). The peptide was extracted from the resin with alternating water and acetic acid, and the filtrates were lyophilized. The Fmoc-peptide resins were cleaved according to standard methods (*Introduction to Cleavage Techniques*, Applied Biosystems, Inc., 1990, pp. 6-12). Some peptides were also assembled using an Advanced. Chem. Tech Synthesizer (Model MPS 350, Louisville, Ky.). Peptides were purified by RP-HPLC (preparative and analytical) using a Waters Delta Prep 3000 system. A C4, C8 or C18 preparative column (10μ, 2.2×25 cm; Vydac, Hesperia, Calif.) was used to isolate peptides, and purity was determined using a C4, C8 or C18 analytical column (5μ, 0.46×25 cm; Vydac). Solvents (A=0.1% TFA/water and B=0.1% TFA/$CH_3CN$) were delivered to the analytical column at a flowrate of 1.0 ml/min and to the preparative column at 15 ml/min. Amino acid analyses were performed on the Waters Pico Tag system and processed using the Maxima program. The peptides were hydrolyzed by vapor-phase acid hydrolysis (115° C., 20-24 h). Hydrolysates were derivatized and analyzed by standard methods (Cohen, S. A., Meys, M., and Tarrin, T. L. (1989), *The Pico Tag Method: A Manual of Advanced Techniques for Amino Acid Analysis*, pp. 11-52, Millipore Corporation, Milford, Mass.). Fast atom bombardment analysis was carried out by M-Scan, Incorporated (West Chester, Pa.). Mass calibration was performed using cesium iodide or cesium iodide/glycerol. Plasma desorption ionization analysis using time of flight detection was carried out on an Applied Biosystems Bio-Ion 20 mass spectrometer.

Peptide compounds useful in the method described herein may also be prepared using recombinant DNA techniques, using methods known in the art. See, e.g., Sambrook et al., *Molecular Cloning: A Laboratory Manual*, 2d Ed., Cold Spring Harbor (1989).

The compounds referenced above form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, and alkali earth salts, e.g. calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Compounds contemplated for the methods described herein may also be compounds having at least 60, 65, 70, 75, 80, 87%, 90%, 92%, 95%, or 100% amino acid sequence identity to any of SEQ ID NOs:41 to 145, as well as fragments thereof, and having an amylin activity. In one embodiment, the compounds for the methods described herein have at least 87%, 90%, 92%, 95%, or 100% amino acid sequence identity to any of SEQ ID NOs:41 to 145; or have at least 92%, 95%, or 100% amino acid sequence identity to any of SEQ ID NOs:41 to 145.

Compounds contemplated for the methods described herein may further include analogs and derivatives of compounds described herein having insertions, extensions, deletions and/or substitutions in at least one or more amino acid positions of SEQ ID NOs:41 to 145, and having amylin activity. The number of amino acid insertions, extensions, deletions, or substitutions may be at least 5, 10, 15, 20, 25, or 30. Insertions, extensions, or substitutions may be with other natural amino acids, synthetic amino acids, peptidomimetics, or other chemical compounds. The analog polypeptides may be derivatized by chemical alterations such as amidation, glycosylation, acylation, sulfation, phosphorylation, acetylation, and cyclization. Such chemical alterations may be obtained through chemical or biochemical methodologies, as well as through in-vivo processes, or any combination thereof. Derivatives of the analog polypeptides contemplated herein may also include conjugation to one or more polymers or small molecule substituents. One type of polymer conjugation is linkage or attachment of polyethylene glycol ("PEG") polymers, polyamino acids (e.g., poly-his, poly-arg, poly-lys, poly-asp, etc.) and/or fatty acid chains of various lengths to the N- or C-terminus or amino acid residue side chains of a polypeptide analog. Small molecule substituents include short alkyls and constrained alkyls (e.g., branched, cyclic, fused, adamantyl), and aromatic groups.

Amylin agonists useful in the methods described herein may also include calcitonins, such as teleost calcitonins, and their analogs and derivatives, as well as calcitonin-gene-related peptides (CGRP) and their analogs and derivatives.

Methods described herein contemplate the use of one or more of the compounds known as amylin, amylin agonist analog, or amylin agonist.

Dosage/Formulation

Amylin and amylin agonist (herein referred to as the "amylin compounds"), including amylin family peptides as described herein, may be administered alone or in combination with pharmaceutically acceptable carriers or excipients, in either single or multiple doses. These pharmaceutical compounds may be formulated with pharmaceutically acceptable carriers or diluents as well as any other known adjuvants and excipients in accordance with conventional techniques such as those disclosed in *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988), incorporated by reference.

Exemplary formulations for an amylin or amylin agonist can be found in U.S. Pat. No. 6,410,511 and U.S. Pat. No. 7,312,196, which are incorporated herein by reference.

In general, compounds described herein may be formulated into a stable, safe pharmaceutical composition for administration to a patient. Pharmaceutical formulations contemplated for use in the methods described herein may comprise approximately 0.01 to 1.0% (w/v), preferably 0.05 to 1.0%, of the amylin compound, approximately 0.02 to 0.5% (w/v) of an acetate, phosphate, citrate or glutamate buffer allowing a pH of the final composition of from about 3.0 to about 7.0; approximately 1.0 to 10% (w/v) of a carbohydrate or polyhydric alcohol tonicifier and, optionally, approximately 0.005 to 1.0% (w/v) of a preservative selected from the group consisting of m-cresol, benzyl alcohol, methyl, ethyl, propyl and butyl parabens and phenol. Such a preservative is generally included if the formulated peptide is to be included in a multiple use product.

In a particular embodiment, a pharmaceutical formulation may contain a range of concentrations of compounds, e.g., between about 0.01% to about 98% w/w, or between about 1 to about 98% w/w, or preferably between 80% and 90% w/w, or preferably between about 0.01% to about 50% w/w, or more preferably between about 10% to about 25% w/w in this embodiment. A sufficient amount of water for injection may be used to obtain the desired concentration of solution.

Additional tonicifying agents such as sodium chloride, as well as other known excipients, may also be present, if desired. It is preferred, however, if such excipients maintain the overall tonicity of the amylin compounds. An excipient may be included in the presently described formulations at various concentrations. For example, an excipient may be included in the concentration range from about 0.02% to about 20% w/w, preferably between about 0.02% and 0.5% w/w, about 0.02% to about 10% w/w, or about 1% to about 20% w/w. In addition, similar to the present formulations themselves, an excipient may be included in solid (including powdered), liquid, semi-solid or gel form.

The pharmaceutical formulations may be composed in various forms, e.g., solid, liquid, semisolid or liquid. The term "solid", as used herein, is meant to encompass all normal uses of this term including, for example, powders and lyophilized formulations. The presently described formulations may be lyophilized.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydronium or hydroxyl ion added does not exceed the capacity of the buffer system to neutralize it.

As described herein, a variety of liquid vehicles are suitable for use in the present peptide formulations, for example, water or an aqueous/organic solvent mixture or suspension.

The stability of a peptide formulation contemplated herein can be enhanced by maintaining the pH of the formulation in the range of about 3.0 to about 7.0 when in liquid form. Preferably, the pH of the formulation is maintained in the range of about 3.5 to 5.0, or about 3.5 to 6.5, most preferably from about 3.7 to 4.3, or about 3.8 to 4.2. A frequently preferred pH may be about 4.0. While not seeking to be bound by this theory, it is presently understood that where the pH of the pharmaceutical formulation exceeds 5.5, chemical degradation of the peptide may be accelerated such that the shelf life is less than about two years.

The buffer used in the practice of the methods contemplated herein can be an acetate buffer (preferably at a final formulation concentration of from about 1-5 to about 60 mM), phosphate buffer (preferably at a final formulation concentration of from about 1-5 to about to about 30 mM) or glutamate buffer (preferably at a final formulation concentration of from about 1-5 to about to about 60 mM). The most preferred buffer is acetate (preferably at a final formulation concentration of from about 5 to about 30 mM).

A stabilizer may be included in the present formulation but, and importantly, is not necessarily needed. If included, however, a stabilizer useful in the practice of the methods provided herein can be a carbohydrate or a polyhydric alcohol. A suitable stabilizer is approximately 1.0 to 10% (w/v) of a carbohydrate or polyhydric alcohol. The polyhydric alcohols and carbohydrates share the same feature in their backbones, i.e., —CHOH—CHOH—, which is responsible for stabilizing the proteins. The polyhydric alcohols include such compounds as sorbitol, mannitol, glycerol, and polyethylene glycols (PEGs). These compounds are straight-chain molecules. The carbohydrates, such as mannose, ribose, sucrose, fructose, trehalose, maltose, inositol, and lactose, on the other hand, are cyclic molecules that may contain a keto or aldehyde group. These two classes of compounds have been demonstrated to be effective in stabilizing protein against denaturation caused by elevated temperature and by freeze-thaw or freeze-drying processes. Suitable carbohydrates include: galactose, arabinose, lactose or any other carbohydrate which does not have an adverse affect on a diabetic patient (if this is a desirable property), i.e., the carbohydrate is not metabolized to form unacceptably large concentrations of glucose in the blood.

Preferably, if a stabilizer is included, the amylin compound is stabilized with a polyhydric alcohol such as sorbitol, mannitol, inositol, glycerol, xylitol, and polypropylene/ethylene glycol copolymer, as well as various polyethylene glycols (PEG) of molecular weight 200, 400, 1450, 3350, 4000, 6000, and 8000). Mannitol is the preferred polyhydric alcohol. Another useful feature of the lyophilized formulations contemplated herein is the maintenance of the tonicity of the lyophilized formulations described herein with the same formulation component that serves to maintain their stability. Mannitol is the preferred polyhydric alcohol used for this purpose.

The United States Pharmacopeia (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Antimicrobial agents should be evaluated to ensure compatibility with all other components of the formula, and their activity should be evaluated in the total formula to ensure that a particular agent that is effective in one formulation is not ineffective in another. It is not uncommon to find that a particular antimicrobial agent will be effective in one formulation but not effective in another formulation.

A preservative is, in the common pharmaceutical sense, a substance that prevents or inhibits microbial growth and may be added to pharmaceutical formulations for this purpose to avoid consequent spoilage of the formulation by microorganisms. While the amount of the preservative is not great, it may nevertheless affect the overall stability of the peptide.

While the preservative for use in the pharmaceutical compositions can range from 0.005 to 1.0% (w/v), the preferred range for each preservative, alone or in combination with others, is: benzyl alcohol (0.1-1.0%), or m-cresol (0.1-0.6%), or phenol (0.1-0.8%) or combination of methyl (0.05-0.25%) and ethyl or propyl or butyl (0.005%-0.03%) parabens. The parabens are lower alkyl esters of para-hydroxybenzoic acid.

An exemplary amylin agonist analog pramlintide, human $^{25,28,29}$Pro-amylin, does not have a tendency to adsorb onto the glass in a glass container when in a liquid form, therefore, a surfactant is not required to further stabilize the pharmaceutical formulation. However, with regard to amylin compounds that do have such a tendency when in liquid form, a surfactant may be used in their formulation. These formulations may then be lyophilized. Surfactants can cause denaturation of protein, both of hydrophobic disruption and by salt bridge separation. Relatively low concentrations of surfactant may exert a potent denaturing activity, because of the strong interactions between surfactant moieties and the reactive sites on proteins. However, judicious use of this interaction can stabilize proteins against interfacial or surface denaturation. Surfactants which could further stabilize the peptide may optionally be present in the range of about 0.001 to 0.3% (w/v) of the total formulation and include polysorbate 80 (i.e., polyoxyethylene(20) sorbitan monooleate), CHAPS® (i.e., 3-[(3-cholamidopropyl) dimethylammonio] 1-propanesulfonate), Brij® (e.g., Brij 35, which is (polyoxyethylene (23) lauryl ether), poloxamer, or another non-ionic surfactant.

It may also be desirable to add sodium chloride or other salt to adjust the tonicity of the pharmaceutical formulation, depending on the tonicifier selected. However, this is optional and depends on the particular formulation selected. Parenteral formulations are preferably isotonic or substantially isotonic.

A preferred vehicle for parenteral products is water. Water of suitable quality for parenteral administration can be prepared either by distillation or by reverse osmosis. Water for injection is the preferred aqueous vehicle for use in the pharmaceutical formulations.

It is possible that other ingredients may be present in the pharmaceutical formulations. Such additional ingredients may include, e.g., wetting agents, emulsifiers, oils, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Additionally, polymer solutions, or mixtures with polymers provide the opportunity for controlled release of the peptide. Such additional ingredients, of course, should not adversely affect the overall stability of the pharmaceutical formulation contemplated herein.

Containers are also an integral part of the formulation of an injection and may be considered a component, for there is no container that is totally inert, or does not in some way affect the liquid it contains, particularly if the liquid is aqueous. Therefore, the selection of a container for a particular injection must be based on a consideration of the composition of the container, as well as of the solution, and the treatment to which it will be subjected. Adsorption of the peptide to the glass surface of the vial can also be minimized, if necessary, by use of borosilicate glass, for example, Wheaton Type I borosilicate glass #33 (Wheaton Type I-33) or its equivalent (Wheaton Glass Co.). Other vendors of similar borosilicate glass vials and cartridges acceptable for manufacture include Kimbel Glass Co., West Co., Bünder Glas GMBH and Form a Vitrum. The biological and chemical properties of amylin may be stabilized by formulation and lyophilization in a Wheaton Type I-33 borosilicate serum vial to a final concentration of 0.1 mg/ml and 10 mg/ml of amylin in the presence of 5% mannitol, and 0.02% Tween 80.

In order to permit introduction of a needle from a hypodermic syringe into a multiple-dose vial and provide for resealing as soon as the needle is withdrawn, the open end of each vial is preferably sealed with a rubber stopper closure held in place by an aluminum band.

Stoppers for glass vials, such as, West 4416/50, 4416/50 (Teflon faced) and 4406/40, Abbott 5139 or any equivalent stopper can be used as the closure for pharmaceutical for injection. These stoppers are compatible with the peptide as well as the other components of the formulation. The inventors have also discovered that these stoppers pass the stopper integrity test when tested using patient use patterns, e.g., the stopper can withstand at least about 100 injections. Alternatively, the peptide can be lyophilized in to vials, syringes or cartridges for subsequent reconstitution. Liquid formulations can be filled into one or two chambered cartridges, or one or two chamber syringes.

The manufacturing process for the above liquid formulations generally involves compounding, sterile filtration and filling steps. The compounding procedure involves dissolution of ingredients in a specific order (preservative followed by stabilizer/tonicity agents, buffers and peptide) or dissolving at the same time.

Alternative formulations, e.g., non-parenteral, may not require sterilization. However, if sterilization is desired or necessary, any suitable sterilization process can be used in developing the peptide pharmaceutical formulation. Typical sterilization processes include filtration, steam (moist heat), dry heat, gases (e.g., ethylene oxide, formaldehyde, chlorine dioxide, propylene oxide, beta-propiolactone, ozone, chloropicrin, peracetic acid methyl bromide and the like), exposure to a radiation source, and aseptic handling. Filtration is the preferred method of sterilization for liquid formulations. The sterile filtration involves filtration through 0.45 µm and 0.22 µm (1 or 2) which may be connected in series. After filtration, the solution is filled into appropriate vials or containers.

The liquid pharmaceutical formulations contemplated herein are intended for parenteral administration. Suitable routes of administration include intramuscular, intravenous, subcutaneous, intradermal, mucosal, intraarticular, intrathecal and the like. These routes include, but are not limited to, oral, nasal, sublingual, pulmonary and buccal routes that may include administration of the amylin compound in liquid, semi-solid or solid form. Administration via some routes require substantially more amylin compound to obtain the desired biological effects due to decreased bioavailability compared to parenteral delivery. In addition, parenteral controlled release delivery can be achieved by forming polymeric microcapsules, matrices, solutions, implants and devices and administering them parenterally or by surgical means. Examples of controlled release formulations are described in U.S. Pat. Nos. 6,368,630, 6,379,704, and 5,766,627, which are incorporated herein by reference. These dosage forms may have a lower bioavailability due to entrapment of some of the peptide in the polymer matrix or device. See e.g., U.S. Pat. Nos. 6,379,704, 6,379,703, and 6,296,842.

The amylin compounds may be provided in dosage unit form. Therapeutically effective amounts of the compounds described herein for affecting body composition will vary with many factors including the age and weight of the patient, the patient's physical condition, their use in combination with other treatments, the ultimate goal that is to be achieved, such as overall weight loss and/or maintaining or increasing lean body mass, as well as other factors known in the medical arts.

However, typical doses may contain from a lower limit of about 1 µg, 5 µg, 10 µg, 50 µg to 100 µg to an upper limit of about 100 µg, 500 µg, 1 mg, 5 mg, 10 mg, 50 mg, or 100 mg of the pharmaceutical compound per day. Also contemplated are other dose ranges such as 0.1 µg to 1 mg of the compound per dose. The doses per day may be delivered in discrete unit doses, provided continuously in a 24 hour period or any portion of that the 24 hours. The number of doses per day may be from 1 to about 4 per day, although it could be more. Continuous delivery can be in the form of a continuous infusion. Exemplary doses and infusion rates include from 0.005 nmol/kg to about 20 nmol/kg per discrete dose or from about 0.01/pmol/kg/min to about 10 pmol/kg/min in a continuous infusion. These doses and infusions can be delivered by intravenous administration (i.v.) or subcutaneous administration (s.c.). Exemplary total dose/delivery of the pharmaceutical composition given i.v. may be about 2 µg to about 8 mg per day, whereas total dose/delivery of the pharmaceutical composition given s.c. may be about 6 µg to about 16 mg per day.

In some embodiments, the route of administration of a compound contemplated for use in the methods described herein results in an average plasma concentration of the compound at or greater than a predetermined plasma concentration criterion for an amount of time of at least a predetermined plasma concentration duration criterion. In some embodiments, the predetermined plasma concentration criterion is at least about 50 pg/mL, at least about 100 pg/mL, at least about 200 pg/mL, at least about 500 pg/mL, at least about 1000 pg/mL, at least about 1500 pg/mL, at least about 2000 pg/mL, at least about 3000 pg/mL, at least 4000 pg/mL, or even at least about 5000 pg/mL. In some embodiments, the predetermined plasma concentration criterion is in the range of about 50 pg/mL to about 5000 pg/mL, about 100 pg/mL to about 5000 pg/mL, about 200 pg/mL to about 5000 pg/mL, about 500 pg/mL to about 5000 pg/mL, about 1000 pg/mL to about 5000 pg/mL, about 2000 pg/mL to about 5000 pg/mL, about 3000 pg/mL to about 5000 pg/mL, about 4000 pg/mL to about 5000 pg/mL, about 50 pg/mL to about 4000 pg/mL, about 100 pg/mL to about 4000 pg/mL, about 200 pg/mL to about 4000 pg/mL, about 500 pg/mL to about 4000 pg/mL, about 1000 pg/mL to about 4000 pg/mL, about 2000 pg/mL to about 4000 pg/mL, about 3000 pg/mL to about 4000 pg/mL, about 50 pg/mL to about 3000 pg/mL, about 100 pg/mL to about 3000 pg/mL, about 200 pg/mL to about 3000 pg/mL, about 500 pg/mL to about 3000 pg/mL, about 1000 pg/mL to about 3000 pg/mL, about 2000 pg/mL to about 3000 pg/mL, about 50 pg/mL to about 2000 pg/mL, about 100 pg/mL to about 2000 pg/mL, about 200 pg/mL to about 2000 pg/mL, about 500 pg/mL to about 2000 pg/mL, about 1000 pg/mL to about 2000 pg/mL, about 50 pg/mL to about 1000 pg/mL, about 100 pg/mL to about 1000 pg/mL, about 200 pg/mL to about 1000 pg/mL, or about 500 pg/mL to about 1000 pg/mL.

In some embodiments, the predetermined plasma concentration duration criterion is at least about 1 hr, at least about 2 hrs, at least about 3 hrs, at least about 4 hrs, at least about 5 hrs, at least 6 about hrs, at least about 7 hrs, at least about 8 hrs, at least about 12 hrs, at least about 1 day, at least about 2 days, at least about 3 days, at least about 4 days, at least about 5 days, at last about 6 days, or even at least 1 week. In some embodiments, the predetermined plasma concentration duration criterion is in the range of about 1 hr to about 2 hrs, about 1 hr to about 3 hrs, about 1 hr to about 4 hrs, about 1 hr to about 5 hrs, about 1 hr to about 6 hrs, about 1 hr to about 7 hrs, about 1 hr to about 8 hrs, about 1 hr to about 12 hrs, about 1 hr to about 1 day, about 1 hr to about 2 day, about 1 hr to about 3 day, about 1 hr to about 4 day, about 1 hr to about 5 day, about 1 hr to about 6 day, about 1 hr to about 1 week, or even about 1 hr to about 2 weeks.

In some embodiments, the compound plasma concentration is at least about 400 pg/mL for at least about 1 hr, at least about 600 pg/mL for at least about 2 hrs, at least about 1000 pg/mL for at least about 1.5 hrs, at least about 1500 pg/mL for at least about 1 hr, at least about 2000 pg/mL for at least about 1 hr, at least about 3000 pg/mL for at least about 0.5 hr. In some embodiments, the compound plasma concentration is at least about 200 pg/mL for at least about 1 hr, at least about 200 pg/mL for at least about 2 hr, at least about 200 pg/mL for at least about 3 hr, at least about 200 pg/mL for at least about 4 hr, at least about 200 pg/mL for at least about 5 hr, at least about 200 pg/mL for at least about 6 hr, at least about 200 pg/mL for at least about 7 hr, at least about 200 pg/mL for at least about 8 hr, at least about 200 pg/mL for at least about 12 hr, at least about 200 pg/mL for at least about 1 day, at least about 200 pg/mL for at least about 2 days, at least about 200 pg/mL for at least about 3 days, at least about 200 pg/mL for at least about 4 day, at least about 200 pg/mL for at least about 5 day, at least about 200 pg/mL for at least about 6 day, at least about 200 pg/mL for at least about 1 week, even at least about 200 pg/mL for at least about 2 weeks. In some embodiments, the compound plasma concentration is at least about 1000 pg/mL for at least about 1 hr, at least about 1000 pg/mL for at least about 2 hr, at least about 1000 pg/mL for at least about 3 hr, at least about 1000 pg/mL for at least about 4 hr, at least about 1000 pg/mL for at least about 5 hr, at least about 1000 pg/mL for at least about 6 hr, at least about 1000 pg/mL for at least about 7 hr, at least about 1000 pg/mL for at least about 8 hr, at least about 1000 pg/mL for at least about 12 hr, at least about 1000 pg/mL for at least about 1 day, at least about 1000 pg/mL for at least about 2 days, at least about 1000 pg/mL for at least about 3 days, at least about 1000 pg/mL for at least about 4 day, at least about 1000 pg/mL for at least about 5 day, at least about 1000 pg/mL for at least about 6 day, at least about 1000 pg/mL for at least about 1 week, even at least about 1000 pg/mL for at least about 2 weeks. In some embodiments, the compound plasma concentration is at least about 2000 pg/mL for at least about 1 hr, at least about 2000 pg/mL for at least about 2 hr, at least about 2000 pg/mL for at least about 3 hr, at least about 2000 pg/mL for at least about 4 hr, at least about 2000 pg/mL for at least about 5 hr, at least about 2000 pg/mL for at least about 6 hr, at least about 2000 pg/mL for at least about 7 hr, at least about 2000 pg/mL for at least about 8 hr, at least about 2000 pg/mL for at least about 12 hr, at least about 2000 pg/mL for at least about 1 day, at least about 2000 pg/mL for at least about 2 days, at least about 2000 pg/mL for at least about 3 days, at least about 2000 pg/mL for at least about 4 day, at least about 2000 pg/mL for at least about 5 day, at least about 2000 pg/mL for at least about 6 day, at least about 2000 pg/mL for at least about 1 week, even at least about 2000 pg/mL for at least about 2 weeks. In some embodiments, the compound plasma concentration is at least about 4000 pg/mL for at least about 1 hr, at least about 4000 pg/mL for at least about 2 hr, at least about 4000 pg/mL for at least about 3 hr, at least about 4000 pg/mL for at least about 4 hr, at least about 4000 pg/mL for at least about 5 hr, at least about 4000 pg/mL for at least about 6 hr, at least about 4000 pg/mL for at least about 7 hr, at least about 4000 pg/mL for at least about 8 hr, at least about 4000 pg/mL for at least about 12 hr, at least about 4000 pg/mL for at least about 1 day, at least about 4000 pg/mL for at least about 2 days, at least about 4000 pg/mL for at least about 3 days, at least about 4000 pg/mL for at least about 4 day, at least about 4000 pg/mL for at least about 5 day, at least about 4000 pg/mL for at least about 6 day, at least about 4000 pg/mL for at least about 1 week, even at least about 4000 pg/mL for at least about 2 weeks. In some embodiments, compound plasma concentration is in the range of about 50 pg/mL to about 5000 pg/mL for about 1 hr to about 2 hrs, about 50 pg/mL to about 5000 pg/mL for about 1 hr to about 4 hrs, about 50 pg/mL to about 5000 pg/mL for about 1 hr to about 8 hrs, about 50 pg/mL to about 5000 pg/mL for about 1 hr to about 12 hrs, about 50 pg/mL to about 5000 pg/mL for about 1 hr to about 1 day, about 50 pg/mL to about 5000 pg/mL for about 1 hr to about 2 days, about 50 pg/mL to about 5000 pg/mL for about 1 hr to about 3 days, about 50 pg/mL to about 5000 pg/mL for about 1 hr to about 4 days, about 50 pg/mL to about 5000 pg/mL for about 1 hr to about 5 days, about 50 pg/mL to about 5000 pg/mL for about 1 hr to about 6 days, about 50 pg/mL to about 5000 pg/mL for about 1 hr to about 1 week, or about 50 pg/mL to about 5000 pg/mL for about 1 hr to about 2 weeks. In some embodiments, compound plasma concentration is in the range of about 500 pg/mL to about 2500 pg/mL for about 1 hr to about 2 hrs, about 500 pg/mL to about 2500 pg/mL for about 1 hr to about 4 hrs, about 500 pg/mL to about 2500 pg/mL for about 1 hr to about 8 hrs, about 500 pg/mL to about 2500 pg/mL for about 1 hr to about 12 hrs, about 500 pg/mL to about 2500 pg/mL for about 1 hr to about 1 day, about 500 pg/mL to about 2500 pg/mL for about 1 hr to about 2 days, about 500 pg/mL to about 2500 pg/mL for about 1 hr to about 3 days, about 500 pg/mL to about 2500 pg/mL for about 1 hr to about 4 days, about 500 pg/mL to about 2500 pg/mL for about 1 hr to about 5 days, about 500 pg/mL to about 2500 pg/mL for about 1 hr to about 6 days, about 500 pg/mL to about 2500 pg/mL for about 1 hr to about 1 week, or about 500 pg/mL to about 2500 pg/mL for about 1 hr to about 2 weeks. Further to any of the embodiments provided herein relating to a compound plasma concentration and a plasma concentration duration of compounds useful in the methods described herein, it is understood that administration can be via single or multiple doses.

Further to methods described herein for reducing body fat or body fat gain, in some embodiments, the method includes administering to the subject an amylin agonist, wherein the amylin agonist has at least 90%, 92%, 95%, or 100% sequence identity to any of SEQ ID NOs:41 through 145, thereby reducing body fat or body fat gain while maintaining or increasing lean body mass, wherein the amylin agonist is administered in a manner sufficient to maintain an average plasma concentration of the amylin agonist of at least about 50 pg/mL for a period of time selected from the group consisting of at least about 1 hr, at least about 2 hrs, at least about 3 hrs, at least about 4 hrs, at least about 5 hrs, at least about 6 hrs, at least about 7 hrs, at least about 8 hrs, at least about 12 hrs, at least about 1 day, at least about 2 days, at least about 3 days, at least about 1 week, at least about 2 weeks, and at least about 1 month. In some embodiments, the average plasma concentration of the amylin agonist is at least about 100 pg/mL, at least about 200 pg/mL, at least about 500 pg/mL, at least about 1000 pg/mL, at least about 1500 pg/mL, at least about 2000 pg/mL, at least about 3000 pg/mL, or even at least about 4000 pg/mL. In some embodiments, body weight is reduced. In some embodiments, body weight is maintained or increased. In some embodiments, the subject is a mammal. In some embodiments, the mammal is a human. In some embodiments, the human is overweight or obese. In some embodiments, the mammal is selected from a group consisting of a chicken, a pig, a cow, a steer, a horse, a sheep, and a goat. In further embodiments, an analog of each parent compound of SEQ ID NOS:41 to 145 contains no more than 1, 2, 3, 4, 5, 6 or 7 total number of modifications, alone or in combination, compared to the parent compound, where the "modification" includes substitutions, insertions, elongations deletions, and derivatizations. In further embodiments, an analog of SEQ ID NOS:41 to 145 has at least 90%, 92%, 95%, or 100% sequence identity to the parent compound. In further embodiments, an analog of each parent compound of SEQ ID NOS:41 to 145 contains no more than 1, 2, 3, 4, 5, 6 or 7 total number of modifications, alone or in combination, compared to the parent compound, where the "modification" includes substitutions, insertions, elongations deletions, and derivatizations. In further embodiments, an analog of SEQ ID NOS: 41 to 145 has at least 90%, 92%, 95%, or 100% sequence identity to the parent compound. In some embodiments, the amylin agonist has at least 92% sequence identity to any one of SEQ ID NOs:41 through 145, or an analog or fragment thereof. In some embodiments, the amylin agonist has at least 95% sequence identity to any one of SEQ ID NOs:41 through 145, or an analog or fragment thereof. In some embodiments, the amylin agonist is any one of SEQ ID NOs:41 through 145 (e.g., SEQ ID NO:138). In some embodiments, the amylin agonist is administered parenterally. In some embodiments, the compound plasma concentration is at least about 400 pg/mL for at least about 1 hr, at least about 600 pg/mL for at least about 2 hrs, at least about 1000 pg/mL for at least about 1.5 hrs, at least about 1500 pg/mL for at least about 1 hr, at least about 2000 pg/mL for at least about 1 hr, at least about 3000 pg/mL for at least about 0.5 hr. In some embodiments, the compound plasma concentration is at least about 200 pg/mL for at least about 1 hr, at least about 200 pg/mL for at least about 2 hr, at least about 200 pg/mL for at least about 3 hr, at least about 200 pg/mL for at least about 4 hr, at least about 200 pg/mL for at least about 5 hr, at least about 200 pg/mL for at least about 6 hr, at least about 200 pg/mL for at least about 7 hr, at least about 200 pg/mL for at least about 8 hr, at least about 200 pg/mL for at least about 12 hr, at least about 200 pg/mL for at least about 1 day, at least about 200 pg/mL for at least about 2 days, at least about 200 pg/mL for at least about 3 days, at least about 200 pg/mL for at least about 4 day, at least about 200 pg/mL for at least about 5 day, at least about 200 pg/mL for at least about 6 day, at least about 200 pg/mL for at least about 1 week, even at least about 200 pg/mL for at least about 2 weeks. In some embodiments, the compound plasma concentration is at least about 1000 pg/mL for at least about 1 hr, at least about 1000 pg/mL for at least about 2 hr, at least about 1000 pg/mL for at least about 3 hr, at least about 1000 pg/mL for at least about 4 hr, at least about 1000 pg/mL for at least about 5 hr, at least about 1000 pg/mL for at least about 6 hr, at least about 1000 pg/mL for at least about 7 hr, at least about 1000 pg/mL for at least about 8 hr, at least about 1000 pg/mL for at least about 12 hr, at least about 1000 pg/mL for at least about 1 day, at least about 1000 pg/mL for at least about 2 days, at least about 1000 pg/mL for at least about 3 days, at least about 1000 pg/mL for at least about 4 day, at least about 1000 pg/mL for at least about 5 day, at least about 1000 pg/mL for at least about 6 day, at least about 1000 pg/mL for at least about 1 week, even at least about 1000 pg/mL for at least about 2 weeks. In some embodiments, the compound plasma concentration is at least about 2000 pg/mL for at least about 1 hr, at least about 2000 pg/mL for at least about 2 hr, at least about 2000 pg/mL for at least about 3 hr, at least about 2000 pg/mL for at least about 4 hr, at least about 2000 pg/mL for at least about 5 hr, at least about 2000 pg/mL for at least about 6 hr, at least about 2000 pg/mL for at least about 7 hr, at least about 2000 pg/mL for at least about 8 hr, at least about 2000 pg/mL for at least about 12 hr, at least about 2000 pg/mL for at least about 1 day, at least about 2000 pg/mL for at least about 2 days, at least about 2000 pg/mL for at least about 3 days, at least about 2000 pg/mL for at least about 4 day, at least about 2000 pg/mL for at least about 5 day, at least about 2000 pg/mL for at least about 6 day, at least about 2000 pg/mL for at least about 1 week, even at least about 2000 pg/mL for at least about 2 weeks. In some embodiments, the compound plasma concentration is at least about 4000 pg/mL for at least about 1 hr, at least about 4000 pg/mL for at least about 2 hr, at least about 4000 pg/mL for at least about 3 hr, at least about 4000 pg/mL for at least about 4 hr, at least about 4000 pg/mL for at least about 5 hr, at least about 4000 pg/mL for at least about 6 hr, at least about 4000 pg/mL for at least about 7 hr, at least about 4000 pg/mL for at least about 8 hr, at least about 4000 pg/mL for at least about 12 hr, at least about 4000 pg/mL for at least about 1 day, at least about 4000 pg/mL for at least about 2 days, at least about 4000 pg/mL for at least about 3 days, at least about 4000 pg/mL for at least about 4 day, at least about 4000 pg/mL for at least about 5 day, at least about 4000 pg/mL for at least about 6 day, at least about 4000 pg/mL for at least about 1 week, even at least about 4000 pg/mL for at least about 2 weeks. In some embodiments, compound plasma concentration is in the range of about 50 pg/mL to about 5000 pg/mL for about 1 hr to about 2 hrs, about 50 pg/mL to about 5000 pg/mL for about 1 hr to about 4 hrs, about 50 pg/mL to about 5000 pg/mL for about 1 hr to about 8 hrs, about 50 pg/mL to about 5000 pg/mL for about 1 hr to about 12 hrs, about 50 pg/mL to about 5000 pg/mL for about 1 hr to about 1 day, about 50 pg/mL to about 5000 pg/mL for about 1 hr to about 2 days, about 50 pg/mL to about 5000 pg/mL for about 1 hr to about 3 days, about 50 pg/mL to about 5000 pg/mL for about 1 hr to about 4 days, about 50 pg/mL to about 5000 pg/mL for about 1 hr to about 5 days, about 50 pg/mL to about 5000 pg/mL for about 1 hr to about 6 days, about 50 pg/mL to about 5000 pg/mL for about 1 hr to about 1 week, or about 50 pg/mL to about 5000 pg/mL for about 1 hr to about 2 weeks. In some embodiments, compound plasma concentration is in the range of about 500 pg/mL to about 2500 pg/mL for about 1 hr to about 2 hrs, about 500 pg/mL to about 2500 pg/mL for about 1 hr to about 4 hrs, about 500 pg/mL to about 2500 pg/mL for about 1 hr to about 8 hrs, about 500 pg/mL to about 2500 pg/mL for about 1 hr to about 12 hrs, about 500 pg/mL to about 2500 pg/mL for about 1 hr to about 1 day, about 500 pg/mL to about 2500 pg/mL for about 1 hr to about 2 days, about 500 pg/mL to about 2500 pg/mL for about 1 hr to about 3 days, about 500 pg/mL to about 2500 pg/mL for about 1 hr to about 4 days, about 500 pg/mL to about 2500 pg/mL for about 1 hr to about 5 days, about 500 pg/mL to about 2500 pg/mL for about 1 hr to about 6 days, about 500 pg/mL to about 2500 pg/mL for about 1 hr to about 1 week, or about 500 pg/mL to about 2500 pg/mL for about 1 hr to about 2 weeks. In another embodiment, there is provided a method of reducing or avoiding adverse side effects, such as nausea and vomiting, and increasing subject acceptance and compliance, by administering an escalating dose over time, from a dose that avoids or minimizes adverse side effects but may be sub-optimal or even sub-therapeutic, to a dose that attains the desired therapeutic effect and which if administered without the prior escalating doses would cause undesirable adverse effects.

Further to methods described herein for altering body composition of a subject in need of treatment, in some embodiments there are provided methods which include administering to the subject an amylin agonist, wherein the amylin agonist has at least 87%, 90%, 92%, or 95% sequence identity to any of SEQ ID NOs:41 through 145, wherein the amylin agonist is administered in a manner sufficient to maintain an average plasma concentration of the amylin agonist of at least about 50 pg/mL for a period of time selected from the group consisting of at least about 1 hr, at least about 2 hrs, at least about 3 hrs, at least about 4 hrs, at least about 5 hrs, at least about 6 hrs, at least about 7 hrs, at least about 8 hrs, at least about 12 hrs, at least about 1 day, at least about 2 days, at least about 3 days, at least about 1 week, at least about 2 weeks, and at least about 1 month. In some embodiments, the average plasma concentration is at least about 100 pg/mL, at least about 200 pg/mL, at least about 500 pg/mL, at least about 1000 pg/mL, at least about 1500 pg/mL, at least about 2000 pg/mL, at least about 3000 pg/mL, or even at least about 4000 pg/mL. In some embodiments, the subject is overweight or obese. In some embodiments, the amylin agonist has at least 92% identity to any one of SEQ ID NOs:41 through 145 or an analog or fragment thereof. In some embodiments, the amylin agonist has at least 95% identity to any one of SEQ ID NOs:41 through 145 or an analog or fragment thereof. In some embodiments, the amylin agonist is any one of SEQ ID NOs: 41 through 145 (e.g., SEQ ID NO:138). In some embodiments, the amylin agonist is administered parenterally. In some embodiments, body weight is reduced. In some embodiments, body weight is maintained or increased. In some embodiments, the compound plasma concentration is at least about 400 pg/mL for at least about 1 hr, at least about 600 pg/mL for at least about 2 hrs, at least about 1000 pg/mL for at least about 1.5 hrs, at least about 1500 pg/mL for at least about 1 hr, at least about 2000 pg/mL for at least about 1 hr, at least about 3000 pg/mL for at least about 0.5 hr. In some embodiments, the compound plasma concentration is at least about 200 pg/mL for at least about 1 hr, at least about 200 pg/mL for at least about 2 hr, at least about 200 pg/mL for at least about 3 hr, at least about 200 pg/mL for at least about 4 hr, at least about 200 pg/mL for at least about 5 hr, at least about 200 pg/mL for at least about 6 hr, at least about 200 pg/mL for at least about 7 hr, at least about 200 pg/mL for at least about 8 hr, at least about 200 pg/mL for at least about 12 hr, at least about 200 pg/mL for at least about 1 day, at least about 200 pg/mL for at least about 2 days, at least about 200 pg/mL for at least about 3 days, at least about 200 pg/mL for at least about 4 day, at least about 200 pg/mL for at least about 5 day, at least about 200 pg/mL for at least about 6 day, at least about 200 pg/mL for at least about 1 week, even at least about 200 pg/mL for at least about 2 weeks. In some embodiments, the compound plasma concentration is at least about 1000 pg/mL for at least about 1 hr, at least about 1000 pg/mL for at least about 2 hr, at least about 1000 pg/mL for at least about 3 hr, at least about 1000 pg/mL for at least about 4 hr, at least about 1000 pg/mL for at least about 5 hr, at least about 1000 pg/mL for at least about 6 hr, at least about 1000 pg/mL for at least about 7 hr, at least about 1000 pg/mL for at least about 8 hr, at least about 1000 pg/mL for at least about 12 hr, at least about 1000 pg/mL for at least about 1 day, at least about 1000 pg/mL for at least about 2 days, at least about 1000 pg/mL for at least about 3 days, at least about 1000 pg/mL for at least about 4 day, at least about 1000 pg/mL for at least about 5 day, at least about 1000 pg/mL for at least about 6 day, at least about 1000 pg/mL for at least about 1 week, even at least about 1000 pg/mL for at least about 2 weeks. In some embodiments, the compound plasma concentration is at least about 2000 pg/mL for at least about 1 hr, at least about 2000 pg/mL for at least about 2 hr, at least about 2000 pg/mL for at least about 3 hr, at least about 2000 pg/mL for at least about 4 hr, at least about 2000 pg/mL for at least about 5 hr, at least about 2000 pg/mL for at least about 6 hr, at least about 2000 pg/mL for at least about 7 hr, at least about 2000 pg/mL for at least about 8 hr, at least about 2000 pg/mL for at least about 12 hr, at least about 2000 pg/mL for at least about 1 day, at least about 2000 pg/mL for at least about 2 days, at least about 2000 pg/mL for at least about 3 days, at least about 2000 pg/mL for at least about 4 day, at least about 2000 pg/mL for at least about 5 day, at least about 2000 pg/mL for at least about 6 day, at least about 2000 pg/mL for at least about 1 week, even at least about 2000 pg/mL for at least about 2 weeks. In some embodiments, the compound plasma concentration is at least about 4000 pg/mL for at least about 1 hr, at least about 4000 pg/mL for at least about 2 hr, at least about 4000 pg/mL for at least about 3 hr, at least about 4000 pg/mL for at least about 4 hr, at least about 4000 pg/mL for at least about 5 hr, at least about 4000 pg/mL for at least about 6 hr, at least about 4000 pg/mL for at least about 7 hr, at least about 4000 pg/mL for at least about 8 hr, at least about 4000 pg/mL for at least about 12 hr, at least about 4000 pg/mL for at least about 1 day, at least about 4000 pg/mL for at least about 2 days, at least about 4000 pg/mL for at least about 3 days, at least about 4000 pg/mL for at least about 4 day, at least about 4000 pg/mL for at least about 5 day, at least about 4000 pg/mL for at least about 6 day, at least about 4000 pg/mL for at least about 1 week, even at least about 4000 pg/mL for at least about 2 weeks. In some embodiments, compound plasma concentration is in the range of about 50 pg/mL to about 5000 pg/mL for about 1 hr to about 2 hrs, about 50 pg/mL to about 5000 pg/mL for about 1 hr to about 4 hrs, about 50 pg/mL to about 5000 pg/mL for about 1 hr to about 8 hrs, about 50 pg/mL to about 5000 pg/mL for about 1 hr to about 12 hrs, about 50 pg/mL to about 5000 pg/mL for about 1 hr to about 1 day, about 50 pg/mL to about 5000 pg/mL for about 1 hr to about 2 days, about 50 pg/mL to about 5000 pg/mL for about 1 hr to about 3 days, about 50 pg/mL to about 5000 pg/mL for about 1 hr to about 4 days, about 50 pg/mL to about 5000 pg/mL for about 1 hr to about 5 days, about 50 pg/mL to about 5000 pg/mL for about 1 hr to about 6 days, about 50 pg/mL to about 5000 pg/mL for about 1 hr to about 1 week, or about 50 pg/mL to about 5000 pg/mL for about 1 hr to about 2 weeks. In some embodiments, compound plasma concentration is in the range of about 500 pg/mL to about 2500 pg/mL for about 1 hr to about 2 hrs, about 500 pg/mL to about 2500 pg/mL for about 1 hr to about 4 hrs, about 500 pg/mL to about 2500 pg/mL for about 1 hr to about 8 hrs, about 500 pg/mL to about 2500 pg/mL for about 1 hr to about 12 hrs, about 500 pg/mL to about 2500 pg/mL for about 1 hr to about 1 day, about 500 pg/mL to about 2500 pg/mL for about 1 hr to about 2 days, about 500 pg/mL to about 2500 pg/mL for about 1 hr to about 3 days, about 500 pg/mL to about 2500 pg/mL for about 1 hr to about 4 days, about 500 pg/mL to about 2500 pg/mL for about 1 hr to about 5 days, about 500 pg/mL to about 2500 pg/mL for about 1 hr to about 6 days, about 500 pg/mL to about 2500 pg/mL for about 1 hr to about 1 week, or about 500 pg/mL to about 2500 pg/mL for about 1 hr to about 2 weeks. In another embodiment, there is provided a method of reducing or avoiding adverse side effects, such as nausea and vomiting, and increasing subject acceptance and compliance, by administering an escalating dose over time, from a dose that avoids or minimizes adverse side effects but may be sub-optimal or even sub-therapeutic, to a dose that attains the desired therapeutic effect and which if administered without the prior escalating doses would cause undesirable adverse effects.

Further to methods described herein for reducing body weight in a subject in need of, or desirous of, weight reduction, in some embodiments there is provided a method including administering to the subject an amylin agonist, wherein the amylin agonist has at least 80%, 87%, 90%, 92%, or 95% identity to any of SEQ ID NOs:41 through 145, wherein the amylin agonist is administered in a manner sufficient to maintain an average plasma concentration of the amylin agonist of at least about 50 pg/mL for a period of time selected from the group consisting of at least about 1 hr, at least about 2 hrs, at least about 3 hrs, at least about 4 hrs, at least about 5 hrs, at least about 6 hrs, at least about 7 hrs, at least about 8 hrs, at least about 12 hrs, at least about 1 day, at least about 2 days, at least about 3 days, at least about 1 week, at least about 2 weeks, and at least about 1 month. In some embodiments, the average plasma concentration is at least about 100 pg/mL, at least about 200 pg/mL, at least about 500 pg/mL, at least about 1000 pg/mL, at least about 1500 pg/mL, at least about 2000 pg/mL, at least about 3000 pg/mL, or even at least about 4000 pg/mL. In some embodiments, the subject is overweight or obese. In some embodiments, the amylin agonist has at least 92% sequence identity to any one of SEQ ID NOs:41 through 145 or an analog or fragment thereof. In some embodiments, the amylin agonist has at least 95% sequence identity to any one of SEQ ID NOs:41 through 145 or an analog or fragment thereof. In some embodiments, the amylin agonist is any one of SEQ ID NOs:41 through 145 (e.g., SEQ ID NO:138). In some embodiments, the amylin agonist is administered parenterally. In some embodiments, body weight is reduced. In some embodiments, body weight is maintained or increased. In some embodiments, the compound plasma concentration is at least about 400 pg/mL for at least about 1 hr, at least about 600 pg/mL for at least about 2 hrs, at least about 1000 pg/mL for at least about 1.5 hrs, at least about 1500 pg/mL for at least about 1 hr, at least about 2000 pg/mL for at least about 1 hr, at least about 3000 pg/mL for at least about 0.5 hr. In some embodiments, the compound plasma concentration is at least about 200 pg/mL for at least about 1 hr, at least about 200 pg/mL for at least about 2 hr, at least about 200 pg/mL for at least about 3 hr, at least about 200 pg/mL for at least about 4 hr, at least about 200 pg/mL for at least about 5 hr, at least about 200 pg/mL for at least about 6 hr, at least about 200 pg/mL for at least about 7 hr, at least about 200 pg/mL for at least about 8 hr, at least about 200 pg/mL for at least about 12 hr, at least about 200 pg/mL for at least about 1 day, at least about 200 pg/mL for at least about 2 days, at least about 200 pg/mL for at least about 3 days, at least about 200 pg/mL for at least about 4 day, at least about 200 pg/mL for at least about 5 day, at least about 200 pg/mL for at least about 6 day, at least about 200 pg/mL for at least about 1 week, even at least about 200 pg/mL for at least about 2 weeks. In some embodiments, the compound plasma concentration is at least about 1000 pg/mL for at least about 1 hr, at least about 1000 pg/mL for at least about 2 hr, at least about 1000 pg/mL for at least about 3 hr, at least about 1000 pg/mL for at least about 4 hr, at least about 1000 pg/mL for at least about 5 hr, at least about 1000 pg/mL for at least about 6 hr, at least about 1000 pg/mL for at least about 7 hr, at least about 1000 pg/mL for at least about 8 hr, at least about 1000 pg/mL for at least about 12 hr, at least about 1000 pg/mL for at least about 1 day, at least about 1000 pg/mL for at least about 2 days, at least about 1000 pg/mL for at least about 3 days, at least about 1000 pg/mL for at least about 4 day, at least about 1000 pg/mL for at least about 5 day, at least about 1000 pg/mL for at least about 6 day, at least about 1000 pg/mL for at least about 1 week, even at least about 1000 pg/mL for at least about 2 weeks. In some embodiments, the compound plasma concentration is at least about 2000 pg/mL for at least about 1 hr, at least about 2000 pg/mL for at least about 2 hr, at least about 2000 pg/mL for at least about 3 hr, at least about 2000 pg/mL for at least about 4 hr, at least about 2000 pg/mL for at least about 5 hr, at least about 2000 pg/mL for at least about 6 hr, at least about 2000 pg/mL for at least about 7 hr, at least about 2000 pg/mL for at least about 8 hr, at least about 2000 pg/mL for at least about 12 hr, at least about 2000 pg/mL for at least about 1 day, at least about 2000 pg/mL for at least about 2 days, at least about 2000 pg/mL for at least about 3 days, at least about 2000 pg/mL for at least about 4 day, at least about 2000 pg/mL for at least about 5 day, at least about 2000 pg/mL for at least about 6 day, at least about 2000 pg/mL for at least about 1 week, even at least about 2000 pg/mL for at least about 2 weeks. In some embodiments, the compound plasma concentration is at least about 4000 pg/mL for at least about 1 hr, at least about 4000 pg/mL for at least about 2 hr, at least about 4000 pg/mL for at least about 3 hr, at least about 4000 pg/mL for at least about 4 hr, at least about 4000 pg/mL for at least about 5 hr, at least about 4000 pg/mL for at least about 6 hr, at least about 4000 pg/mL for at least about 7 hr, at least about 4000 pg/mL for at least about 8 hr, at least about 4000 pg/mL for at least about 12 hr, at least about 4000 pg/mL for at least about 1 day, at least about 4000 pg/mL for at least about 2 days, at least about 4000 pg/mL for at least about 3 days, at least about 4000 pg/mL for at least about 4 day, at least about 4000 pg/mL for at least about 5 day, at least about 4000 pg/mL for at least about 6 day, at least about 4000 pg/mL for at least about 1 week, even at least about 4000 pg/mL for at least about 2 weeks. In some embodiments, compound plasma concentration is in the range of about 50 pg/mL to about 5000 pg/mL for about 1 hr to about 2 hrs, about 50 pg/mL to about 5000 pg/mL for about 1 hr to about 4 hrs, about 50 pg/mL to about 5000 pg/mL for about 1 hr to about 8 hrs, about 50 pg/mL to about 5000 pg/mL for about 1 hr to about 12 hrs, about 50 pg/mL to about 5000 pg/mL for about 1 hr to about 1 day, about 50 pg/mL to about 5000 pg/mL for about 1 hr to about 2 days, about 50 pg/mL to about 5000 pg/mL for about 1 hr to about 3 days, about 50 pg/mL to about 5000 pg/mL for about 1 hr to about 4 days, about 50 pg/mL to about 5000 pg/mL for about 1 hr to about 5 days, about 50 pg/mL to about 5000 pg/mL for about 1 hr to about 6 days, about 50 pg/mL to about 5000 pg/mL for about 1 hr to about 1 week, or about 50 pg/mL to about 5000 pg/mL for about 1 hr to about 2 weeks. In some embodiments, compound plasma concentration is in the range of about 500 pg/mL to about 2500 pg/mL for about 1 hr to about 2 hrs, about 500 pg/mL to about 2500 pg/mL for about 1 hr to about 4 hrs, about 500 pg/mL to about 2500 pg/mL for about 1 hr to about 8 hrs, about 500 pg/mL to about 2500 pg/mL for about 1 hr to about 12 hrs, about 500 pg/mL to about 2500 pg/mL for about 1 hr to about 1 day, about 500 pg/mL to about 2500 pg/mL for about 1 hr to about 2 days, about 500 pg/mL to about 2500 pg/mL for about 1 hr to about 3 days, about 500 pg/mL to about 2500 pg/mL for about 1 hr to about 4 days, about 500 pg/mL to about 2500 pg/mL for about 1 hr to about 5 days, about 500 pg/mL to about 2500 pg/mL for about 1 hr to about 6 days, about 500 pg/mL to about 2500 pg/mL for about 1 hr to about 1 week, or about 500 pg/mL to about 2500 pg/mL for about 1 hr to about 2 weeks. In further embodiments, an analog of each parent compound of SEQ ID NOS:41 to 145 contains no more than 1, 2, 3, 4, 5, 6 or 7 total number of modifications, alone or in combination, compared to the parent compound, where the "modification" includes substitutions, insertions, elongations deletions, and derivatizations. In further embodiments, an analog of SEQ ID NOS:41 to 145 has at least 80%, 87%, 90%, or 92% or 95% identical to the parent compound.

Further to methods described herein for reducing caloric intake in a subject in need of thereof, in some embodiments there is provided a method including administering to the subject an amylin agonist, wherein the amylin agonist has at least 80%, 87%, 90%, 92%, or 95% sequence identity to any of SEQ ID NOs:41 through 145, wherein the amylin agonist is administered in a manner sufficient to maintain an average plasma concentration of the amylin agonist of at least about 50 pg/mL for a period of time selected from the group consisting of at least about 1 hr, at least about 2 hrs, at least about 3 hrs, at least about 4 hrs, at least about 5 hrs, at least about 6 hrs, at least about 7 hrs, at least about 8 hrs, at least about 12 hrs, at least about 1 day, at least about 2 days, at least about 3 days, at least about 1 week, at least about 2 weeks, and at least about 1 month. In some embodiments, the average plasma concentration is at least about 100 pg/mL, at least about 200 pg/mL, at least about 500 pg/mL, at least about 1000 pg/mL, at least about 1500 pg/mL, at least about 2000 pg/mL, at least about 3000 pg/mL, or even at least about 4000 pg/mL. In some embodiments, the subject is overweight or obese. In further embodiments, an analog of each parent compound of SEQ ID NOS:41 to 145 contains no more than 1, 2, 3, 4, 5, 6 or 7 total number of modifications, alone or in combination, compared to the parent compound, where the "modification" includes substitutions, insertions, elongations deletions, and derivatizations. In further embodiments, an analog of SEQ ID NOS:41 to 145 has at least 80%, 87%, 90%, 92%, or 95% sequence identity to the parent compound. In some embodiments, the amylin agonist has at least 92% sequence identity to any one of SEQ ID NOs:41 through 145 or an analog or fragment thereof. In some embodiments, the amylin agonist has at least 95% sequence identity to any one of SEQ ID NOs:41 through 145 or an analog or fragment thereof. In some embodiments, the amylin agonist is any one of SEQ ID NOs:41 through 145 (e.g., SEQ ID NO:138). In some embodiments, the amylin agonist is administered parenterally. In some embodiments, body weight is reduced. In some embodiments, body weight is maintained or increased. In some embodiments, the compound plasma concentration is at least about 400 pg/mL for at least about 1 hr, at least about 600 pg/mL for at least about 2 hrs, at least about 1000 pg/mL for at least about 1.5 hrs, at least about 1500 pg/mL for at least about 1 hr, at least about 2000 pg/mL for at least about 1 hr, at least about 3000 pg/mL for at least about 0.5 hr. In some embodiments, the compound plasma concentration is at least about 200 pg/mL for at least about 1 hr, at least about 200 pg/mL for at least about 2 hr, at least about 200 pg/mL for at least about 3 hr, at least about 200 pg/mL for at least about 4 hr, at least about 200 pg/mL for at least about 5 hr, at least about 200 pg/mL for at least about 6 hr, at least about 200 pg/mL for at least about 7 hr, at least about 200 pg/mL for at least about 8 hr, at least about 200 pg/mL for at least about 12 hr, at least about 200 pg/mL for at least about 1 day, at least about 200 pg/mL for at least about 2 days, at least about 200 pg/mL for at least about 3 days, at least about 200 pg/mL for at least about 4 day, at least about 200 pg/mL for at least about 5 day, at least about 200 pg/mL for at least about 6 day, at least about 200 pg/mL for at least about 1 week, even at least about 200 pg/mL for at least about 2 weeks. In some embodiments, the compound plasma concentration is at least about 1000 pg/mL for at least about 1 hr, at least about 1000 pg/mL for at least about 2 hr, at least about 1000 pg/mL for at least about 3 hr, at least about 1000 pg/mL for at least about 4 hr, at least about 1000 pg/mL for at least about 5 hr, at least about 1000 pg/mL for at least about 6 hr, at least about 1000 pg/mL for at least about 7 hr, at least about 1000 pg/mL for at least about 8 hr, at least about 1000 pg/mL for at least about 12 hr, at least about 1000 pg/mL for at least about 1 day, at least about 1000 pg/mL for at least about 2 days, at least about 1000 pg/mL for at least about 3 days, at least about 1000 pg/mL for at least about 4 day, at least about 1000 pg/mL for at least about 5 day, at least about 1000 pg/mL for at least about 6 day, at least about 1000 pg/mL for at least about 1 week, even at least about 1000 pg/mL for at least about 2 weeks. In some embodiments, the compound plasma concentration is at least about 2000 pg/mL for at least about 1 hr, at least about 2000 pg/mL for at least about 2 hr, at least about 2000 pg/mL for at least about 3 hr, at least about 2000 pg/mL for at least about 4 hr, at least about 2000 pg/mL for at least about 5 hr, at least about 2000 pg/mL for at least about 6 hr, at least about 2000 pg/mL for at least about 7 hr, at least about 2000 pg/mL for at least about 8 hr, at least about 2000 pg/mL for at least about 12 hr, at least about 2000 pg/mL for at least about 1 day, at least about 2000 pg/mL for at least about 2 days, at least about 2000 pg/mL for at least about 3 days, at least about 2000 pg/mL for at least about 4 day, at least about 2000 pg/mL for at least about 5 day, at least about 2000 pg/mL for at least about 6 day, at least about 2000 pg/mL for at least about 1 week, even at least about 2000 pg/mL for at least about 2 weeks. In some embodiments, the compound plasma concentration is at least about 4000 pg/mL for at least about 1 hr, at least about 4000 pg/mL for at least about 2 hr, at least about 4000 pg/mL for at least about 3 hr, at least about 4000 pg/mL for at least about 4 hr, at least about 4000 pg/mL for at least about 5 hr, at least about 4000 pg/mL for at least about 6 hr, at least about 4000 pg/mL for at least about 7 hr, at least about 4000 pg/mL for at least about 8 hr, at least about 4000 pg/mL for at least about 12 hr, at least about 4000 pg/mL for at least about 1 day, at least about 4000 pg/mL for at least about 2 days, at least about 4000 pg/mL for at least about 3 days, at least about 4000 pg/mL for at least about 4 day, at least about 4000 pg/mL for at least about 5 day, at least about 4000 pg/mL for at least about 6 day, at least about 4000 pg/mL for at least about 1 week, even at least about 4000 pg/mL for at least about 2 weeks. In some embodiments, compound plasma concentration is in the range of about 50 pg/mL to about 5000 pg/mL for about 1 hr to about 2 hrs, about 50 pg/mL to about 5000 pg/mL for about 1 hr to about 4 hrs, about 50 pg/mL to about 5000 pg/mL for about 1 hr to about 8 hrs, about 50 pg/mL to about 5000 pg/mL for about 1 hr to about 12 hrs, about 50 pg/mL to about 5000 pg/mL for about 1 hr to about 1 day, about 50 pg/mL to about 5000 pg/mL for about 1 hr to about 2 days, about 50 pg/mL to about 5000 pg/mL for about 1 hr to about 3 days, about 50 pg/mL to about 5000 pg/mL for about 1 hr to about 4 days, about 50 pg/mL to about 5000 pg/mL for about 1 hr to about 5 days, about 50 pg/mL to about 5000 pg/mL for about 1 hr to about 6 days, about 50 pg/mL to about 5000 pg/mL for about 1 hr to about 1 week, or about 50 pg/mL to about 5000 pg/mL for about 1 hr to about 2 weeks. In some embodiments, compound plasma concentration is in the range of about 500 pg/mL to about 2500 pg/mL for about 1 hr to about 2 hrs, about 500 pg/mL to about 2500 pg/mL for about 1 hr to about 4 hrs, about 500 pg/mL to about 2500 pg/mL for about 1 hr to about 8 hrs, about 500 pg/mL to about 2500 pg/mL for about 1 hr to about 12 hrs, about 500 pg/mL to about 2500 pg/mL for about 1 hr to about 1 day, about 500 pg/mL to about 2500 pg/mL for about 1 hr to about 2 days, about 500 pg/mL to about 2500 pg/mL for about 1 hr to about 3 days, about 500 pg/mL to about 2500 pg/mL for about 1 hr to about 4 days, about 500 pg/mL to about 2500 pg/mL for about 1 hr to about 5 days, about 500 pg/mL to about 2500 pg/mL for about 1 hr to about 6 days, about 500 pg/mL to about 2500 pg/mL for about 1 hr to about 1 week, or about 500 pg/mL to about 2500 pg/mL for about 1 hr to about 2 weeks. In some embodiments the percent reduction in mean daily caloric intake is greater than or equal to 25%, 30%, 35% or even 36%, as shown herein in human subjects. In another embodiment, there is provided a method of reducing or avoiding adverse side effects, such as nausea and vomiting, and increasing subject acceptance and compliance, by administering an escalating dose over time, from a dose that avoids or minimizes adverse side effects but may be sub-optimal or even sub-therapeutic, to a dose that attains the desired therapeutic effect and which if administered without the prior escalating doses would cause undesirable adverse effects.

Further to methods described herein for reducing body fat or body fat gain in a subject in need of treatment while maintaining or increasing lean body mass, in some embodiments there is provided a method including administering to the subject an amylin agonist, wherein the amylin agonist has at least 80%, 87%, 90%, 92%, 95%, or 100% sequence identity to any of SEQ ID NOs:41 through 145, wherein the amylin agonist is administered in a manner sufficient to provide an integrated plasma concentration of the amylin agonist over time ($AUC_{0-inf}$) of at least about 1000 pg*h/mL. In some embodiments, the integrated plasma concentration of the amylin agonist over time ($AUC_{0-inf}$) is at least about 1500 pg*h/mL, at least about 2000 pg*h/mL, at least about 2500 pg*h/mL, at least about 3000 pg*h/mL, or even at least about 4000 pg*h/mL. In some embodiments, including without limitation embodiments contemplating multiple administration of a compound useful in the methods described herein, the integrated plasma concentration of the amylin agonist over time is at least about 5000 pg*h/mL, at least about 6000 pg*h/mL, at least about 7000 pg*h/mL, at least about 8000 pg*h/mL, at least about 9000 pg*h/mL, at least about 10000 pg*h/mL, at least about 11000 pg*h/mL, at least about 12000 pg*h/mL, at least about 18000 pg*h/mL, at least about 24000 pg*h/mL, at least about 36000 pg*h/mL, at least about 48000 pg*h/mL, at least about 60000 pg*h/mL, at least about 72000 pg*h/mL, or even at least about 84000 pg*h/mL. In some embodiments, the integrated plasma concentration of the amylin agonist over time is in the range of about 5000 pg*h/mL to about 12000 pg*h/mL, about 12000 pg*h/mL to about 18000 pg*h/mL, about 18000 pg*h/mL to about 24000 pg*h/mL, about 24000 pg*h/mL to about 36000 pg*h/mL, about 36000 pg*h/mL to about 48000 pg*h/mL, about 48000 pg*h/mL to about 60000 pg*h/mL, or even about 60000 pg*h/mL to about 84000 pg*h/mL. In another embodiment, there is provided a method of reducing or avoiding adverse side effects, such as nausea and vomiting, and increasing subject acceptance and compliance, by administering an escalating dose over time, from a dose that avoids or minimizes adverse side effects but may be sub-optimal or even sub-therapeutic, to a dose that attains the desired therapeutic effect and which if administered without the prior escalating doses would cause undesirable adverse effects.

Example 1

High fat-fed (58% kcal from fat, D12331, Research Diets), male SPRAGUE-DAWLEY® rats were implanted subcutaneously with 28-day osmotic pumps (Durect Corp.) delivering amylin (300 μg/kg/day), sibutramine (3 mg/kg/day), or vehicle (50% dimethyl sulfoxide (DMSO)). Low fat-fed rats (11% kcal from fat, D12329, Research Diets) were also implanted with pumps delivering vehicle. Food intake and body weight measurements were obtained weekly.

Rats were sacrificed by cardiac puncture under anesthesia. Triglyceride levels were measured on a COBAS Mira plasma analyzer (Roche), and leptin and insulin were assayed according to Linco Research rat RIA kits. Body composition was measured by chemical analysis (Covance Laboratories, Madison, Wis.).

Amylin was synthesized by Amylin Pharmaceuticals, Inc. by solid-phase chemistry, purified by HPLC (>98% purity, 84% peptide content), and characterized by amino acid analysis and LC/MS. Sibutramine was extracted from the drug product MERIDIA® using water as a solvent, purified by RP-HPLC (>98% purity), and characterized by NMR and LC/MS.

All data are represented as mean±SEM. Analysis of variance was used to test for group differences.

The rats were fattened for 10 weeks prior to drug treatment. The high fat-fed rats were designated as obesity-prone (top 50% of weight gainers) or obesity-resistant (bottom 50%) based on the amount of weight gained through week 7. No difference between prone and resistant animals was observed for food consumption, body weight, or plasma metabolites in response to drug treatment; therefore, these groups were combined (Table 1A, FIGS. 1A, 1B, 3A, 3B, and 3C).

TABLE 1A

| Week | AMYLIN | | SIBUTRAMINE | |
|---|---|---|---|---|
| | Caloric Intake | Body Weight | Caloric Intake | Body Weight |
| 1 | 45%* | 6%* | 45%* | 6%* |
| 2 | 14%* | 7%* | 8%* | 6%* |
| 3 | 10%* | 8%* | −1% | 6%* |
| 4 | 10%* | 8%* | −3% | 3% |

*P < 0.05, significantly different from high fat-fed controls.

Figure 2A:
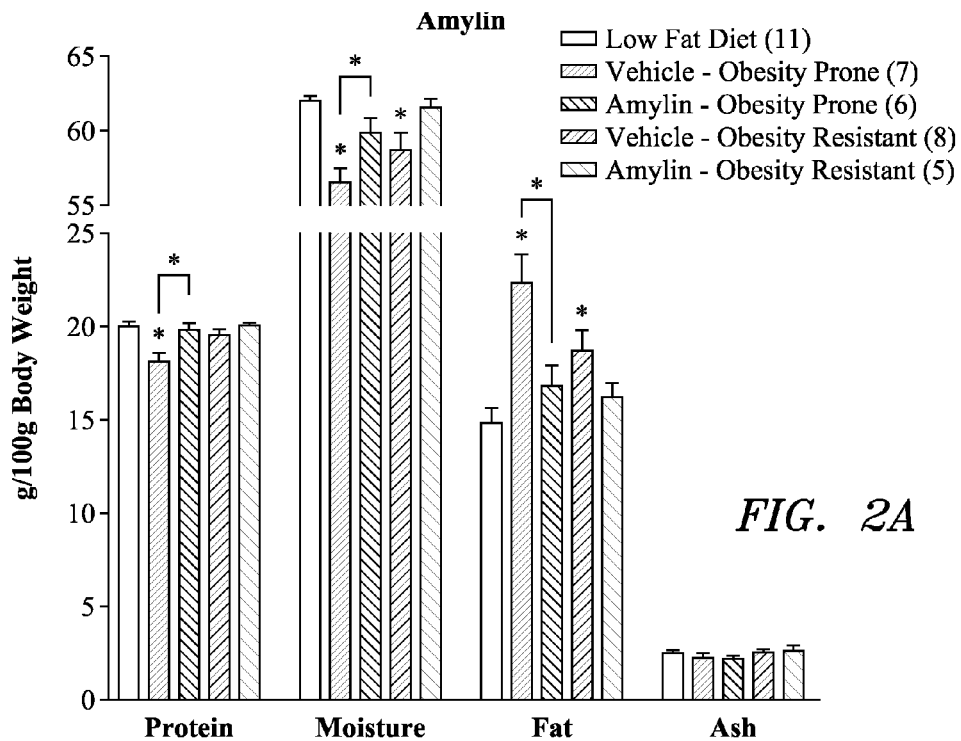
FIGS. 2A and 2B depict the body composition of DIO rats chronically administered with amylin or sibutramine, respectively.
Figure 2B:
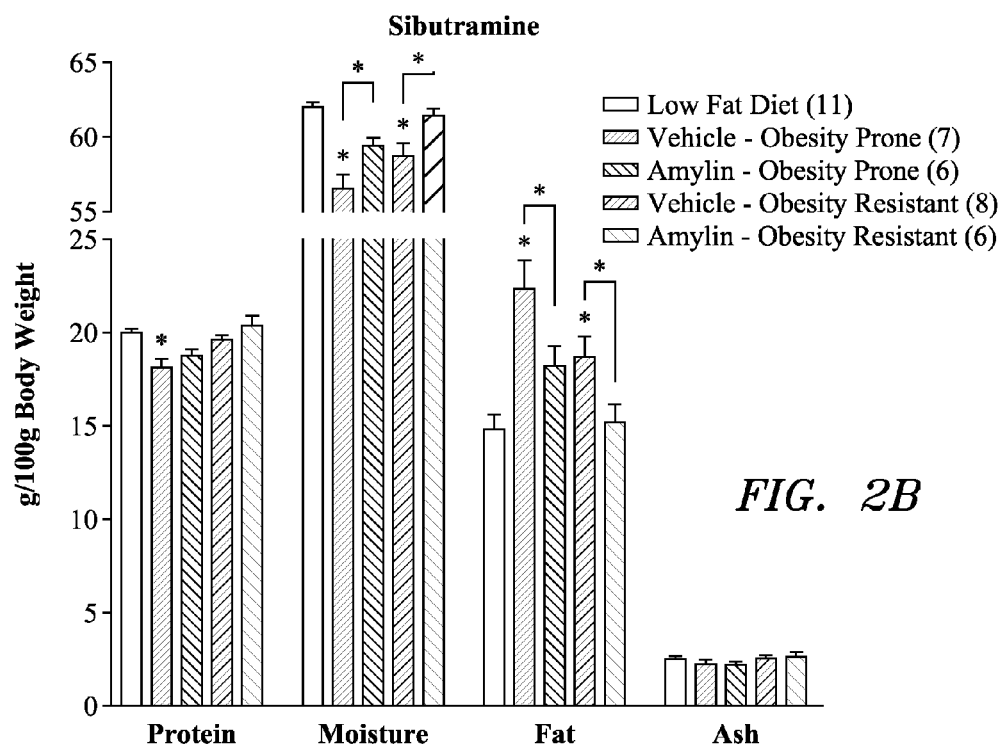
Figure 3A:
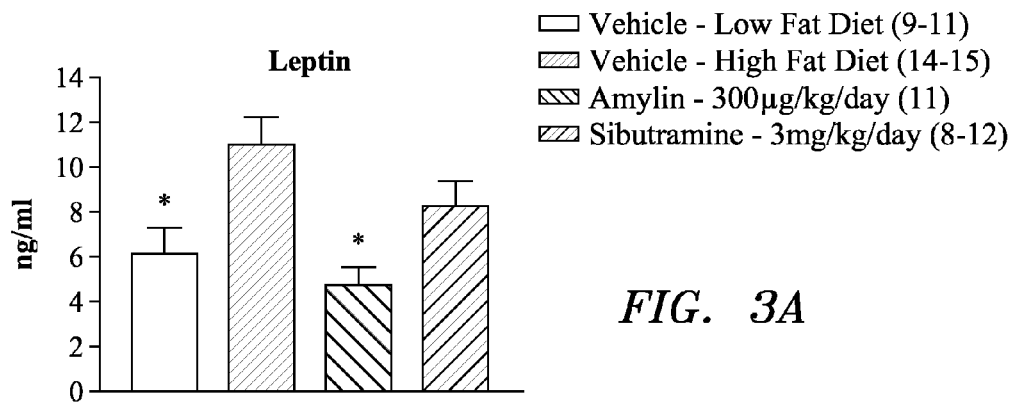
FIGS. 3A, 3B and 3C depict the leptin, insulin and triglycerides levels of DIO rats chronically administered amylin or sibutramine.
Figure 3B:
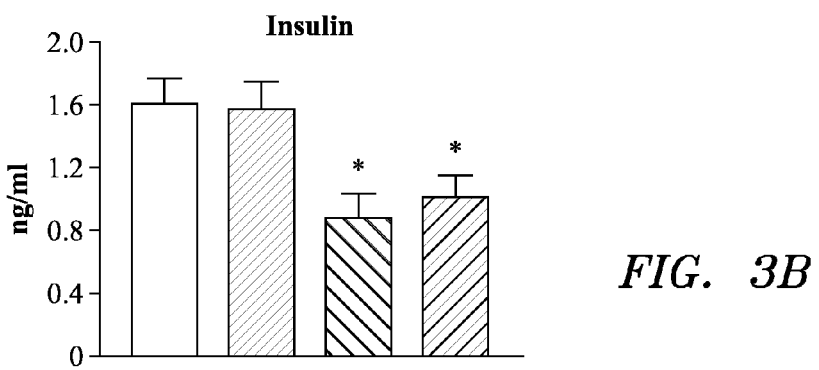
Figure 3C:
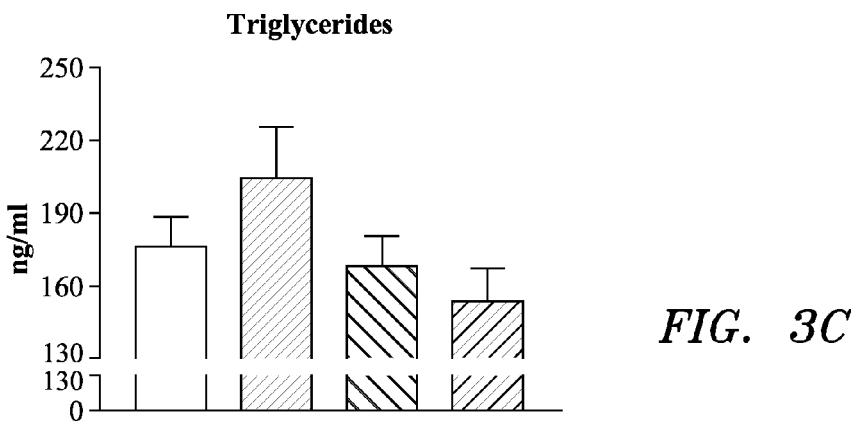

In this study, an obesity-prone/obesity-resistant difference in drug interaction was found for protein weight in amylin-treated rats, and thus body composition parameters were measured separately in obesity-prone and obesity-resistant animals in each drug group (FIGS. 2A and 2B). In obesity-prone rats, there was an increase in protein in the amylin-treated group when compared to the control group (vehicle only).

Example 2

Figure 4A:
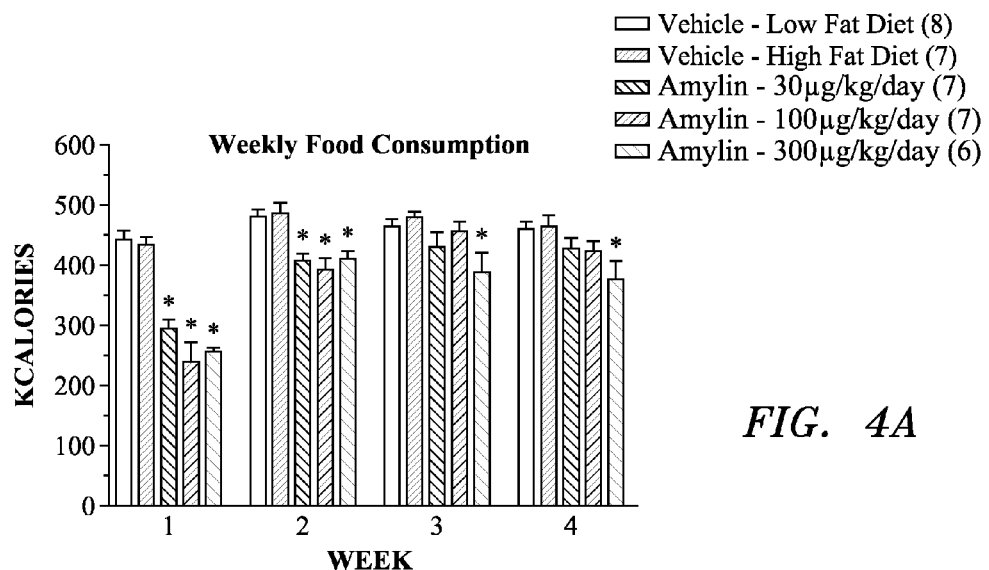
FIGS. 4A and 4B show the effects on food consumption and body weight, respectively, of three differing doses of amylin in DIO rats.
Figure 4B:
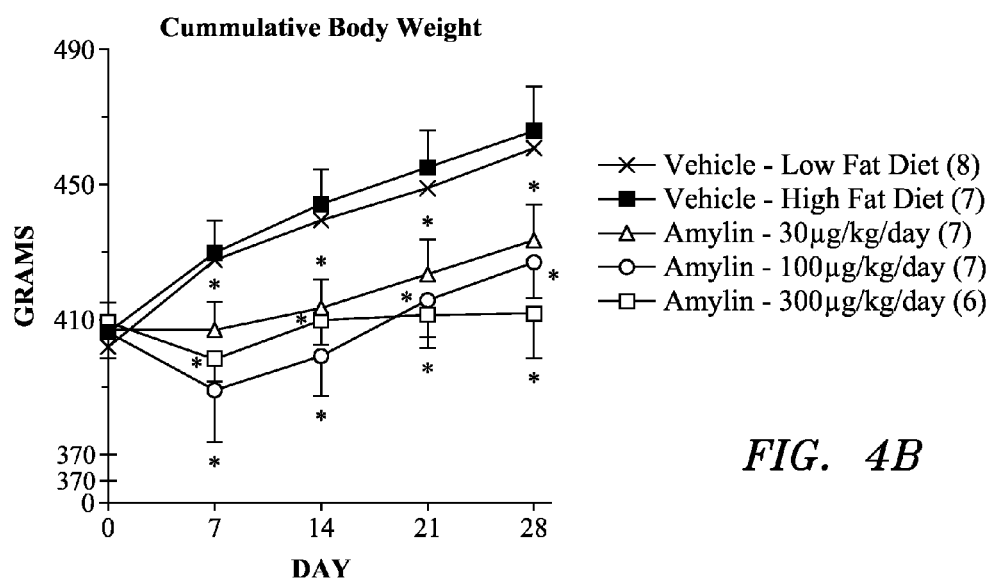
Figure 5:
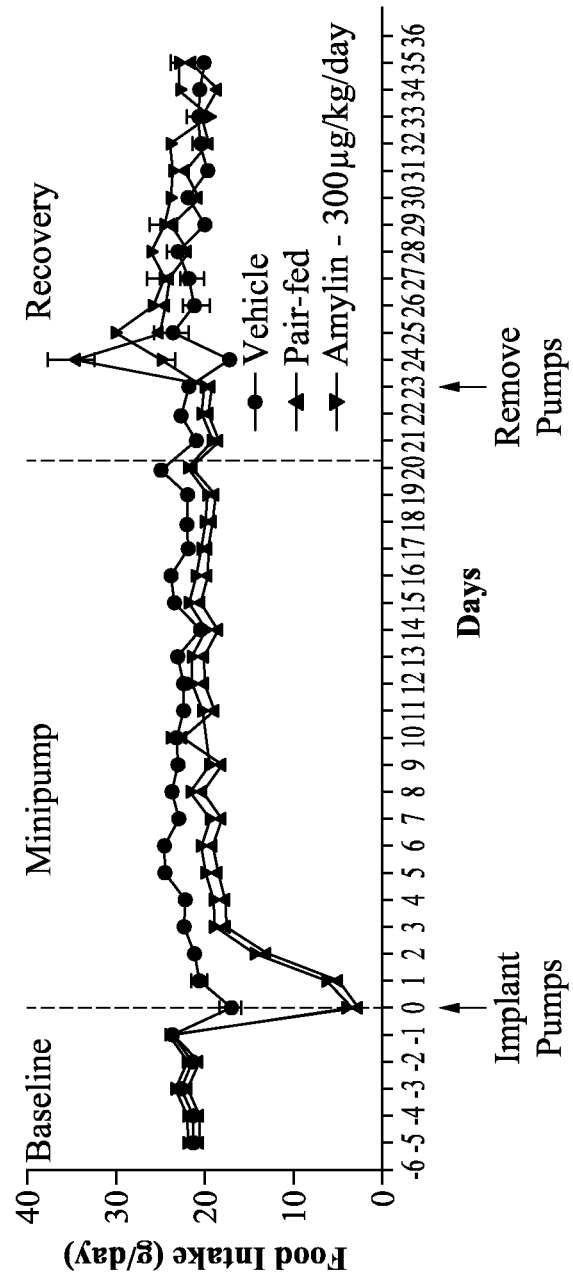
FIG. 5 depicts the effect of amylin on food intake in lean rats.
Figure 6A:
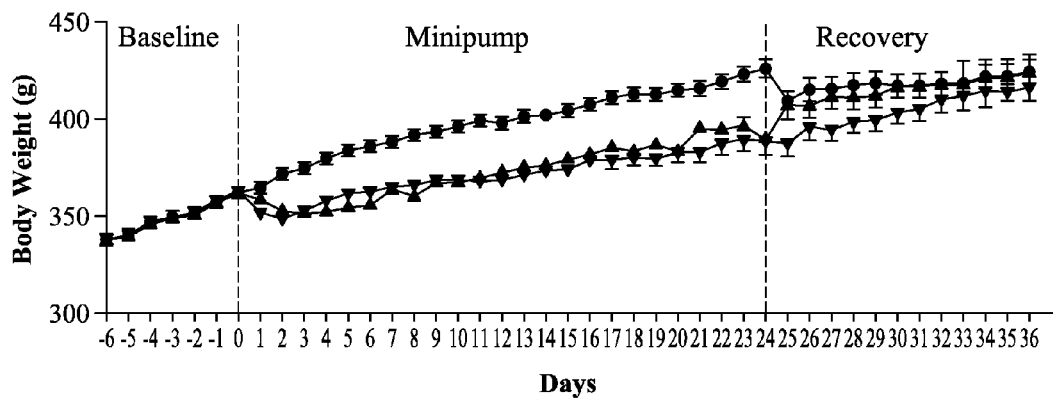
FIGS. 6A and 6B depict the effect of amylin on weight in lean rats.
Figure 6B:
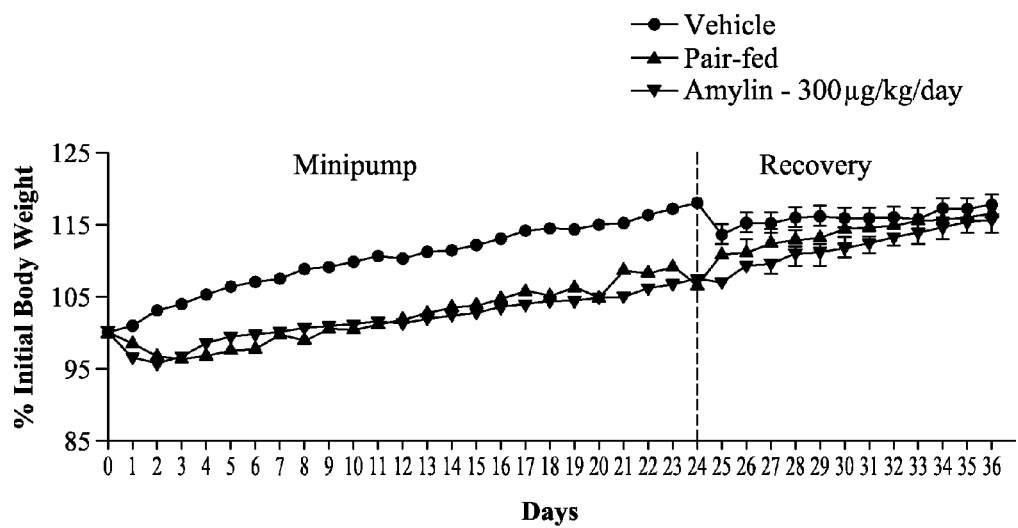
Figure 7:
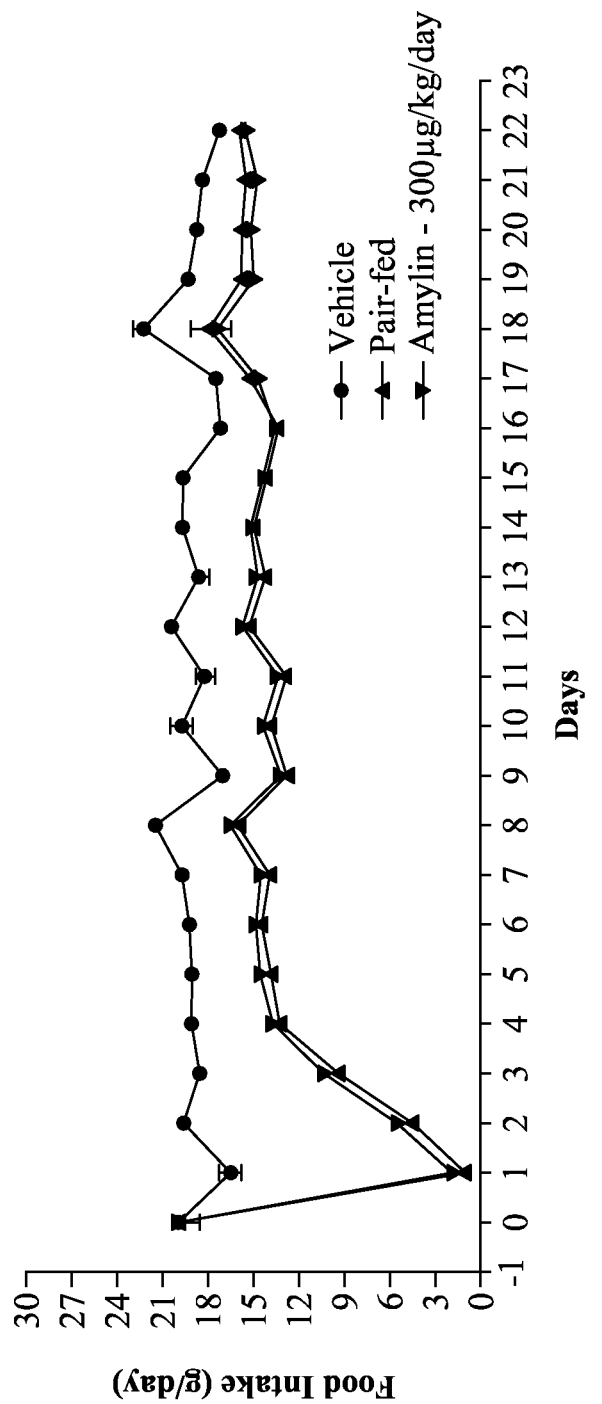
FIG. 7 depicts the effect of amylin on food intake in DIO Levin rats.
Figure 8A:
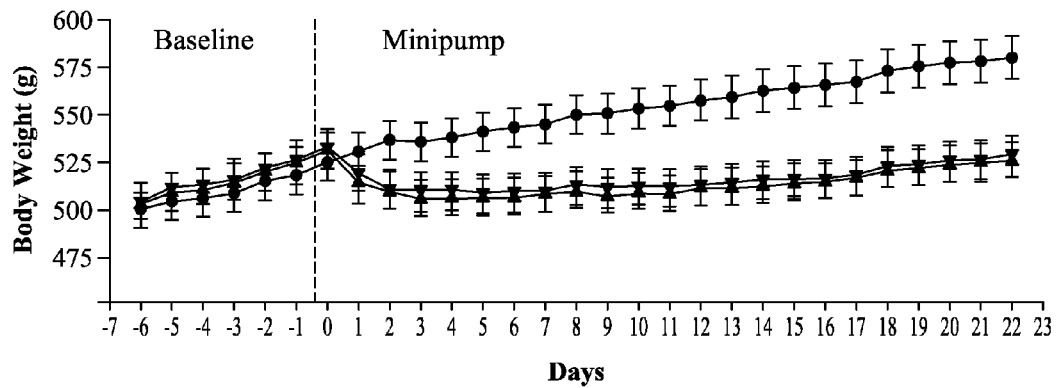
FIGS. 8A and 8B depict the effect of amylin on weight in DIO Levin rats.
Figure 8B:
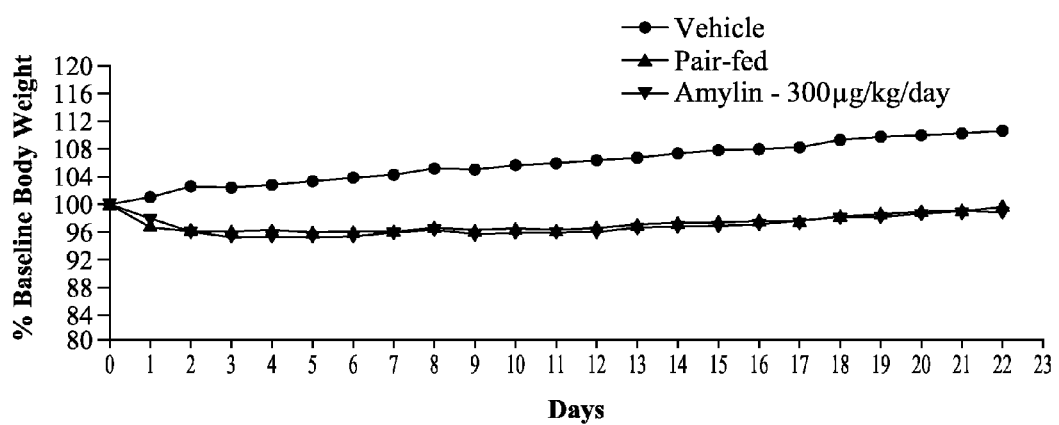
Figure 11A:
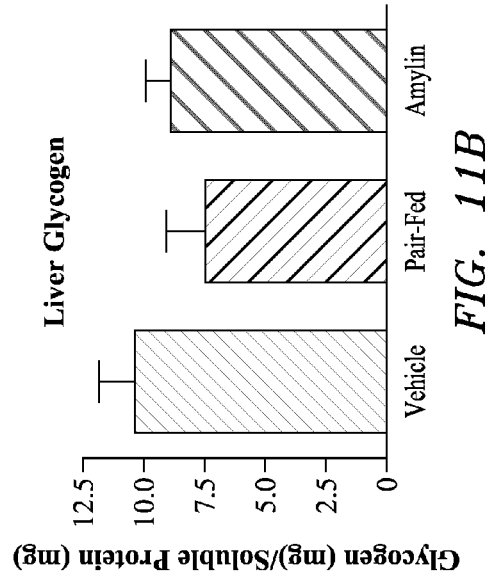
FIGS. 11A-11D depict the tissue biochemistry of DIO Levin rats chronically administered amylin.
Figure 11C:
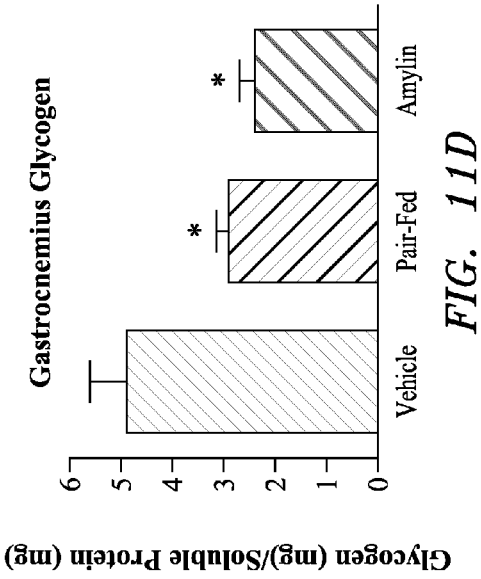
Figure 11B:
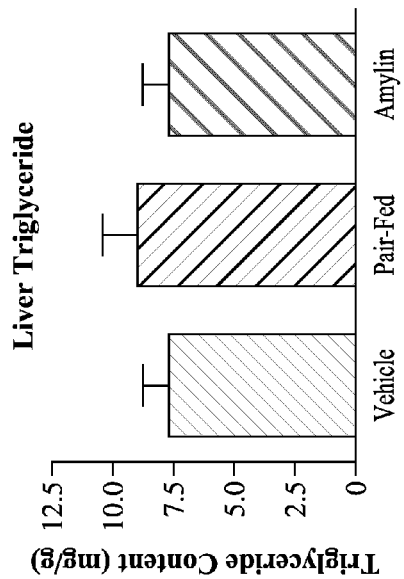
Figure 11D:
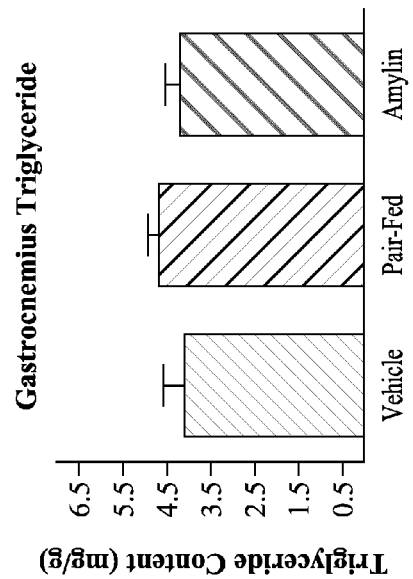
Figure 12A:
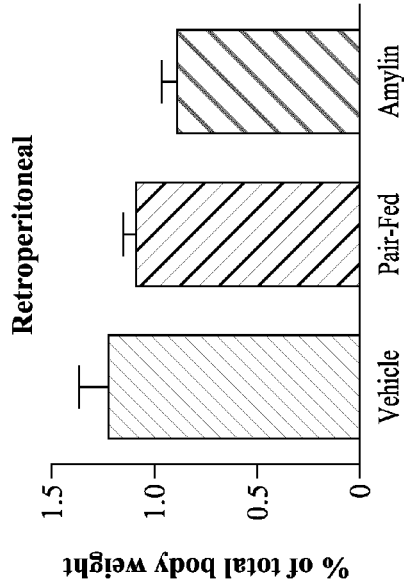
FIGS. 12A-12D depict the weight of selected fat pad as a percent of total body weight in DIO Levin rats chronically administered amylin.
Figure 12B:
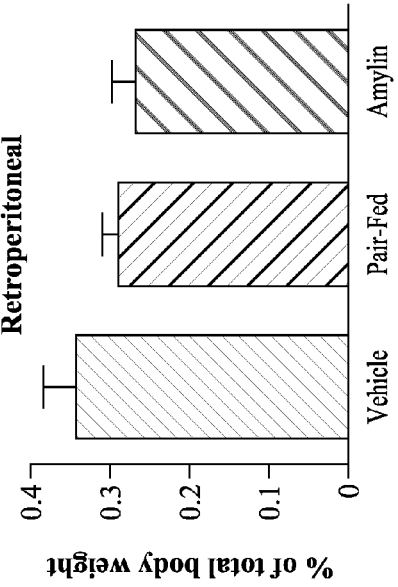
Figure 12C:
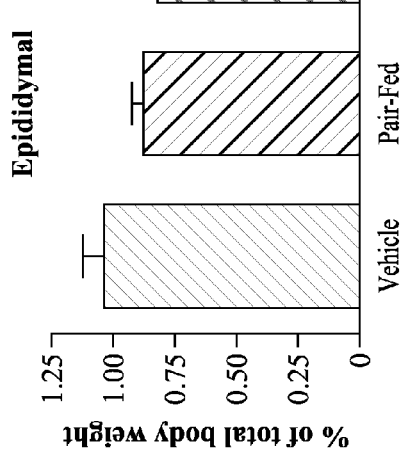
Figure 12D:
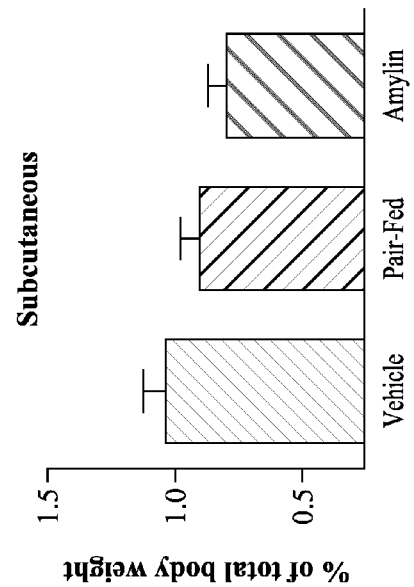

This experiment was similar to that of Example 1, except that the study group consisted of high fat-fed rats implanted with pumps delivering three doses of amylin (30, 100, and 300 μg/kg/day) or vehicle. Table 1B and FIGS. 4A and 4B show that the effects of amylin on food intake and body weight are dose-dependent, with a reduction in body weight gain being observed at 30 μg/kg/day.

TABLE 1B

| | 30 μg/kg/day amylin | | 100 μg/kg/day amylin | | 300 μg/kg/day amylin | |
|---|---|---|---|---|---|---|
| Week | Caloric Intake | Body Weight | Caloric Intake | Body Weight | Caloric Intake | Body Weight |
| 1 | 32%* | 5%* | 45%* | 10%* | 41%* | 7%* |
| 2 | 17%* | 7%* | 19%* | 10%* | 15%* | 8%* |
| 3 | 10% | 7%* | 4% | 9%* | 19%* | 10%* |
| 4 | 8% | 7%* | 9% | 8%* | 19%* | 12%* |

*$P < 0.05$, significantly different from high fat-fed controls.

Example 3

Lean, male Harlan SPRAGUE DAWLEY® (HSD) (Harlan 7012) rats were maintained on "standard chow" (~5% calories from fat). DIO (Levin; Charles River) male rats were maintained on Research Diets' 12266B chow (17% protein, 51% carbohydrate, 32% fat) for 6 weeks prior to the experiment, resulting in a weight gain of ~150 to 200 g/animal.

Rats were implanted subcutaneously with 28-day osmotic pumps containing either amylin (300 mg/kg/day; synthesized at Amylin Pharmaceuticals, Inc.) or vehicle (50% DMSO; control and pair-fed groups). Food intake and body weight were recorded daily (FIGS. 5, 6A, 6B, 7, 8A, and 8B). While amylin and vehicle-control rats always had ad libitum access to food, intake in the pair-fed control group was restricted to the amount consumed by the amylin-treated group.

On the final day of the experiment, rats were deeply anaesthetized and sacrificed by cardiac puncture. Plasma triglycerides, glucose, and cholesterol were measured on a COBAS Mira plasma Analyzer (Roche). Plasma leptin and insulin were measured using Linco Research kits. (See, FIGS. 9A-9F and 10A-10E.) Body composition was measured by chemical analysis (Covance Laboratories, Madison, Wis.). Fat pad weights of the epididymal, retroperitoneal, subcutaneous, and perirenal fat pads (all unilateral; analysis only done in DIO animals) were carefully dissected and weighed (FIGS. 12A-12D). In analyzing the tissue biochemistry, triglycerides were powdered under liquid $N_2$ and extracted in chloroform: methanol. 0.6% NaCl solution was then added and the tubes were vortexed, centrifuged, and the organic phase was transferred to glass scintillation vials and dried under a stream of $N_2$. Dried lipids were resuspended and triglycerides were quantified by enzymatic assay (Pointe Scientific, Inc.). Tissue glycogen was measured by the amyloglucosidase method. (See FIGS. 11A-11D.)

All data are represented as mean±SEM. Analysis of variance (ANOVA) and Bonferroni post-hoc tests were used to test for group differences (SYSTAT® for Windows). A P-value<0.05 was considered significant. Graphs were generated using PRISM® 4 for Windows (Graphpad Software).

Results showed that amylin treatment and pair-feeding both induced a 12% reduction in body weight relative to vehicle controls in lean and DIO rats. Chronic infusion of amylin significantly changed body composition relative to pair-fed and/or vehicle animals.

Amylin-treated lean rats and pair-fed lean rats showed a significant reduction in weight gain compared to vehicle rats. Amylin-treated lean rats also had a lower percent body fat relative to pair-fed while the percent protein remained relatively constant, suggesting amylin may have a metabolic mechanism of action as well as the ability to reduce food intake.

TABLE 2

| | Vehicle | Pair-fed | Amylin |
|---|---|---|---|
| Weight (g) | 425.45 | 397.85* | 392.25* |
| Fat (%) | 8.3 ± 0.9 | 9.52 ± 1.2 | 7.2 ± 1.5† |
| Protein (%) | 20.72 ± 0.69 | 20.62 ± 1.07 | 20.67 ± 0.74 |
| Moisture (%) | 66.68 ± 0.7 | 66.27 ± 0.7 | 67.57 ± 0.7† |

*$P < 0.05$, compared to vehicle.
†$P < 0.05$, compared to pair-fed.

Amylin-treated DIO rats and pair-fed DIO rats showed a significant reduction in weight gain compared to vehicle rats. Amylin-treated DIO rats also showed a significant decrease in percent body fat and a significant preservation or gain in percent protein. Again, this result suggests that amylin may have a metabolic as well as weight reducing effect.

TABLE 3

| | Vehicle | Pair-fed | Amylin |
|---|---|---|---|
| Weight (g) | 612.99 | 551.33* | 548.94* |
| Fat (%) | 33.4 ± 4.7 | 27.64 ± 5.7 | 24.3 ± 6.5* |
| Protein (%) | 15.61 ± 1.37 | 16.85 ± 1.53 | 18.09 ± 1.68* |
| Moisture (%) | 49.46 ± 2.6 | 53.93 ± 4.5 | 56.68 ± 4.4* |
| Ash (%) | 1.34 ± 0.26 | 1.81 ± 0.59 | 1.65 ± 0.34 |

*$P < 0.05$, compared to vehicle.

Also seen from this experiment is that reductions in body weight were not accompanied by alterations in liver or muscle triglycerides or in liver glycogen content. However, rats given amylin or pair-fed had significantly reduced muscle glycogen content. Further, reductions in body weight were generally accompanied by reductions in metabolites and plasma insulin and leptin.

Example 4

In this experiment, the effect of prior or concurrent food restriction on the ability of amylin to effect weight loss was evaluated. Retired female breeder rats were maintained on a high fat diet (40% fat) for 8 weeks. Prior to drug treatment, rats were either ad-lib fed or food restricted to 95% of their starting body weight. The rats were then sub-divided into treatment groups that received either vehicle or amylin (100 μg/kg/day) and placed under either a restricted or ad-lib feeding schedule (8 groups total).

Figure 13A:
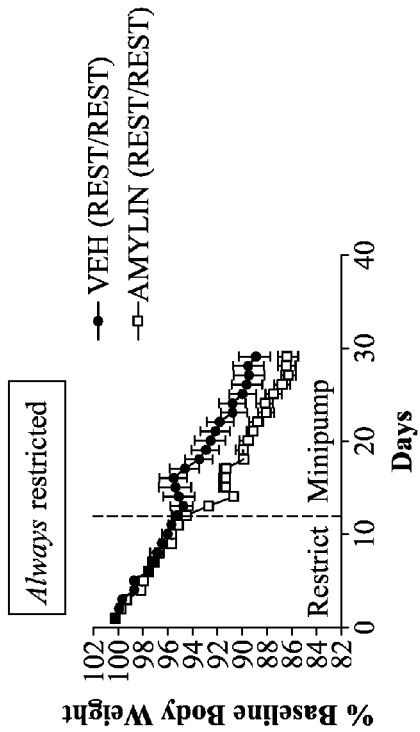
FIGS. 13A-13P depict the effect of amylin, in conjunction with prior or concurrent food restriction, on food intake, body weight and body composition in retired female breeder rats.
Figure 13B:
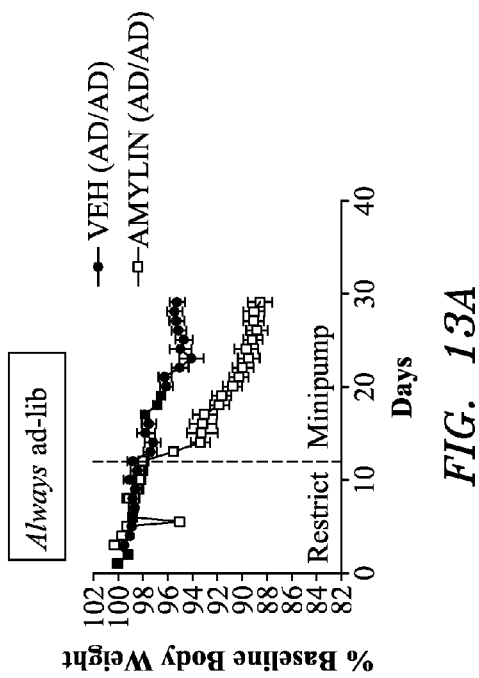
Figure 13C:
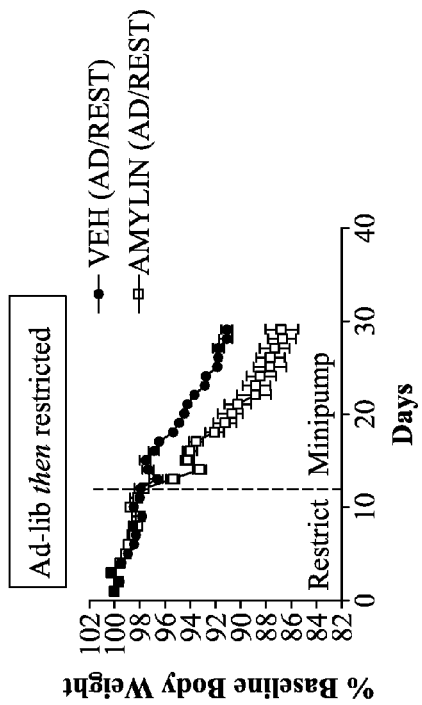
Figure 13D:
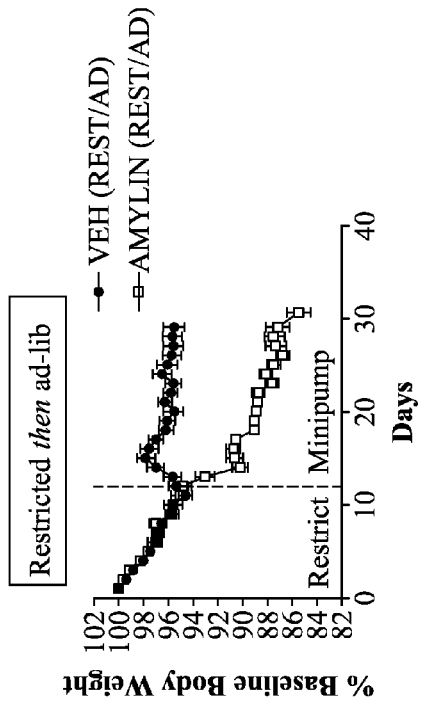
Figure 13E:
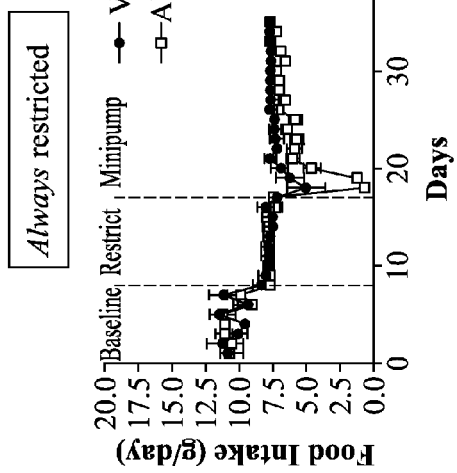
Figure 13F:
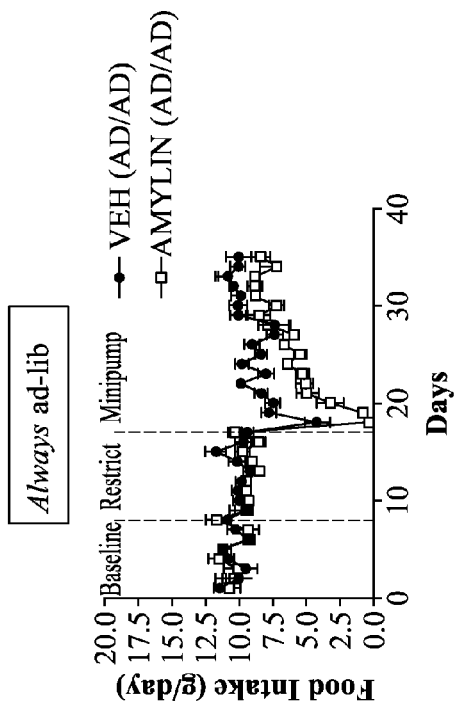
Figure 13G:
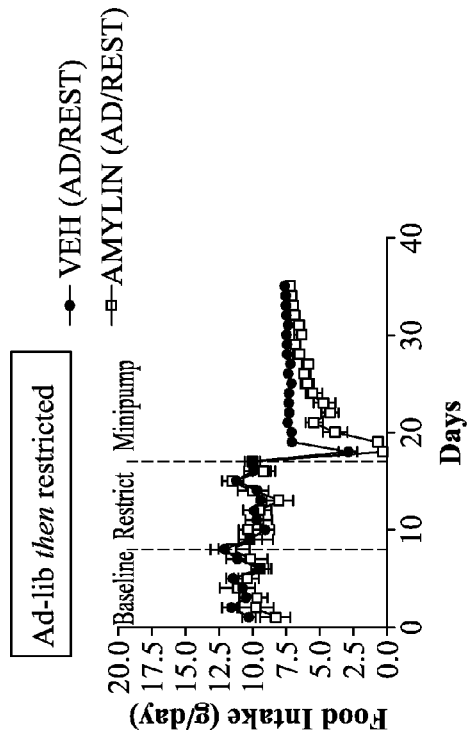
Figure 13H:
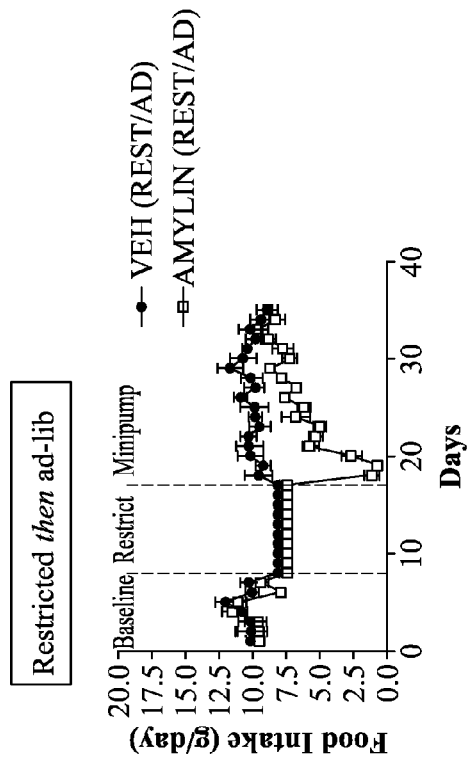
Figure 13I:
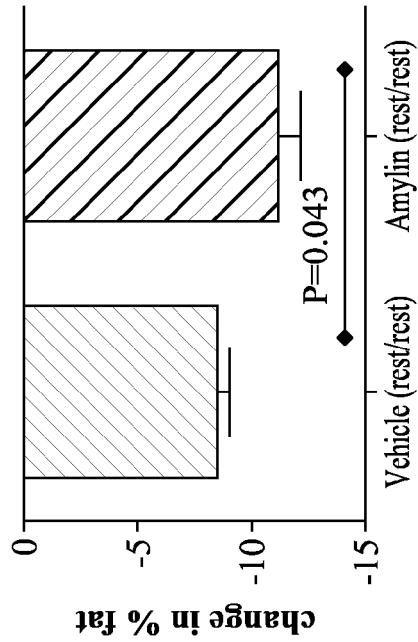
Figure 13J:
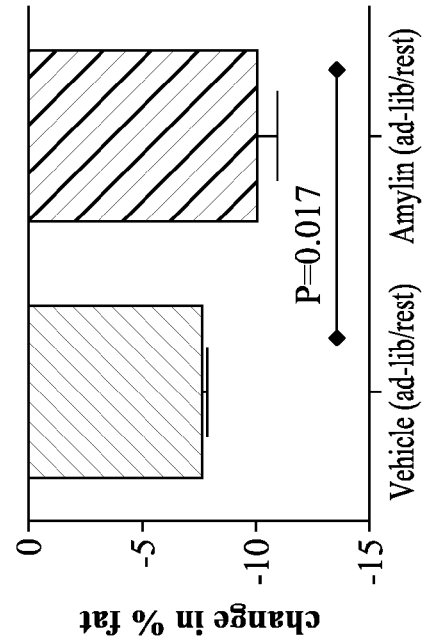
Figure 13K:
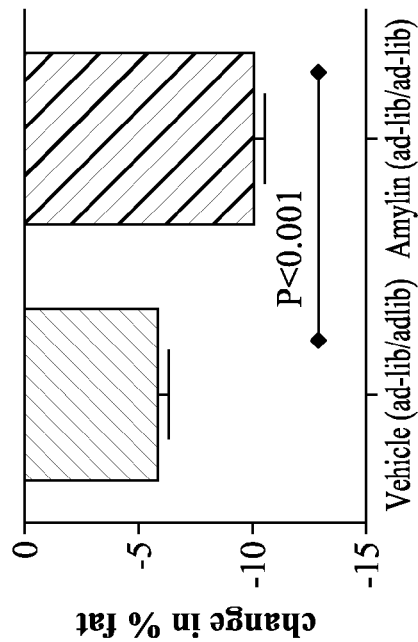
Figure 13L:
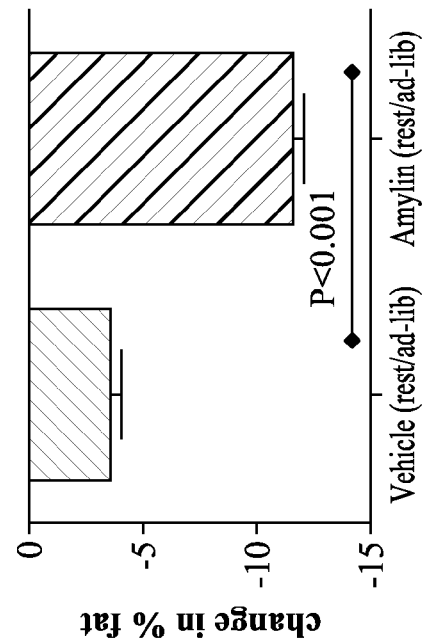
Figure 13N:
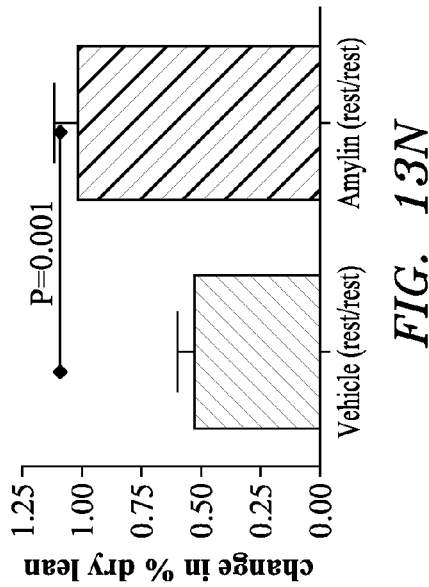
Figure 13P:
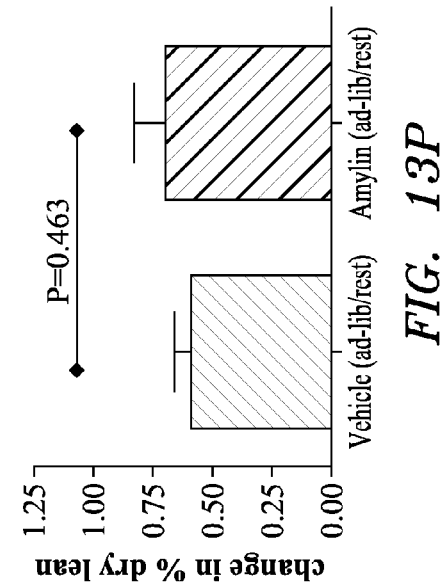
Figure 13M:
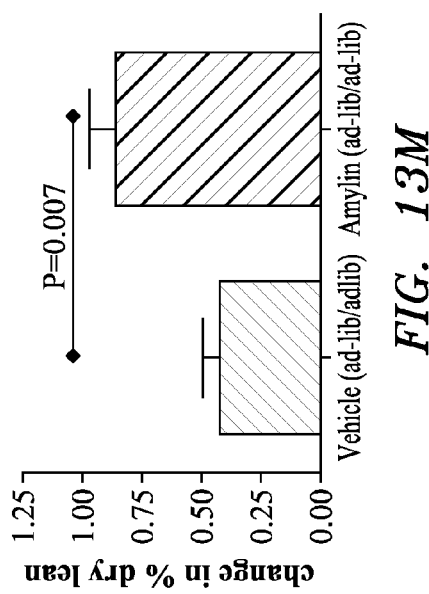
Figure 13O:
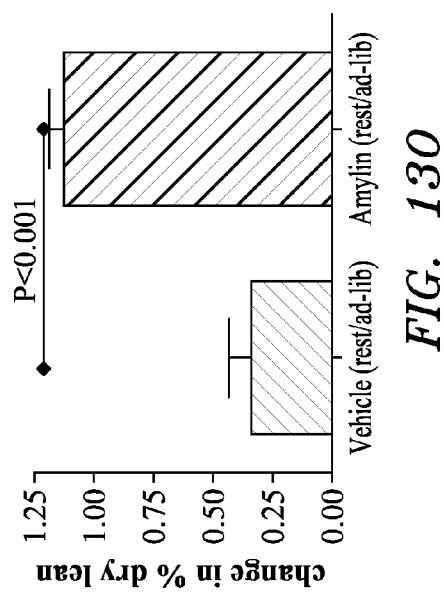
Figure 14A:
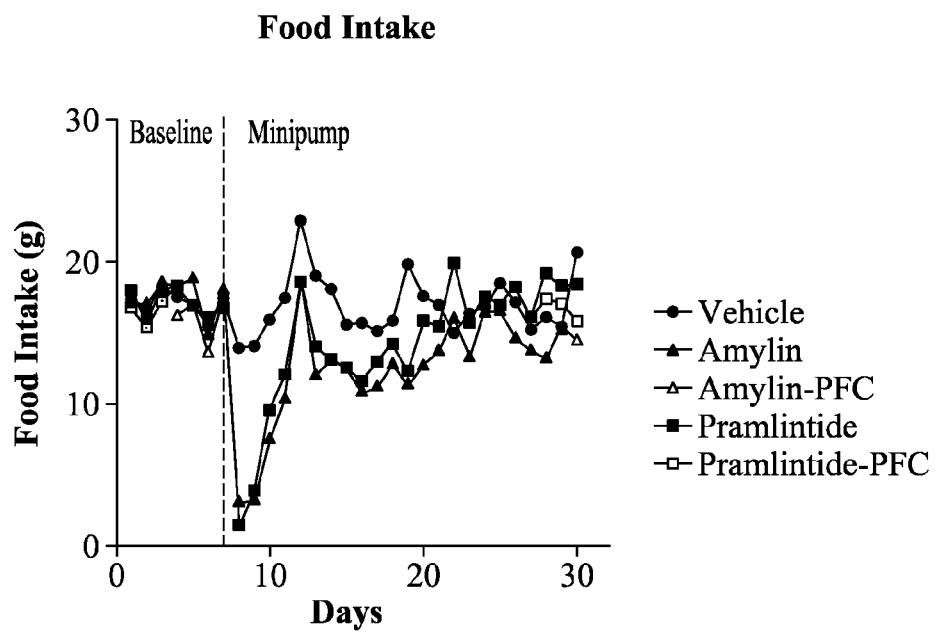
FIGS. 14A-14H depict the effect of amylin and pramlintide on food intake, body weight and body composition in rats.
Figure 14B:
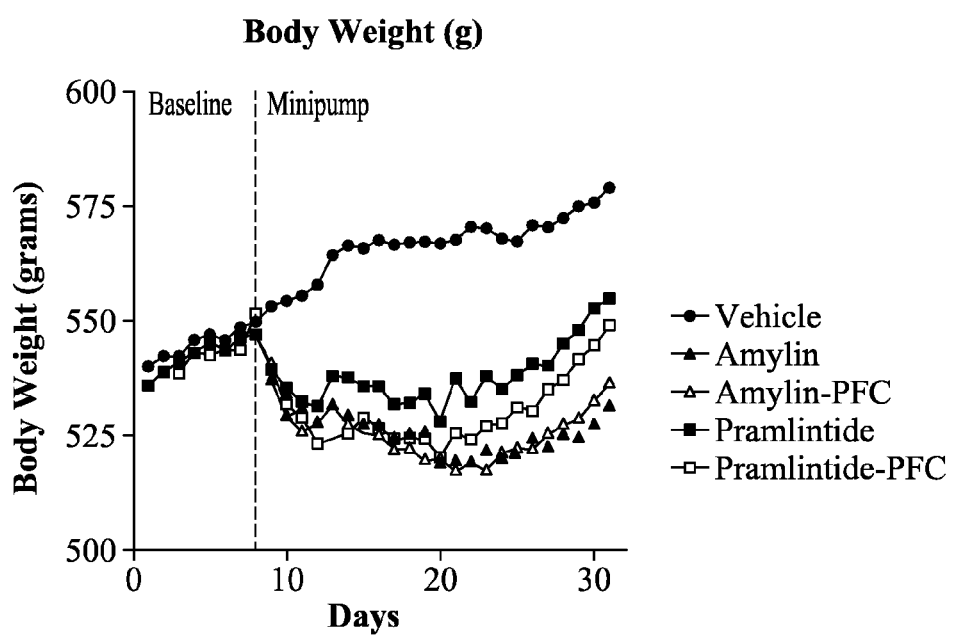
Figure 14C:
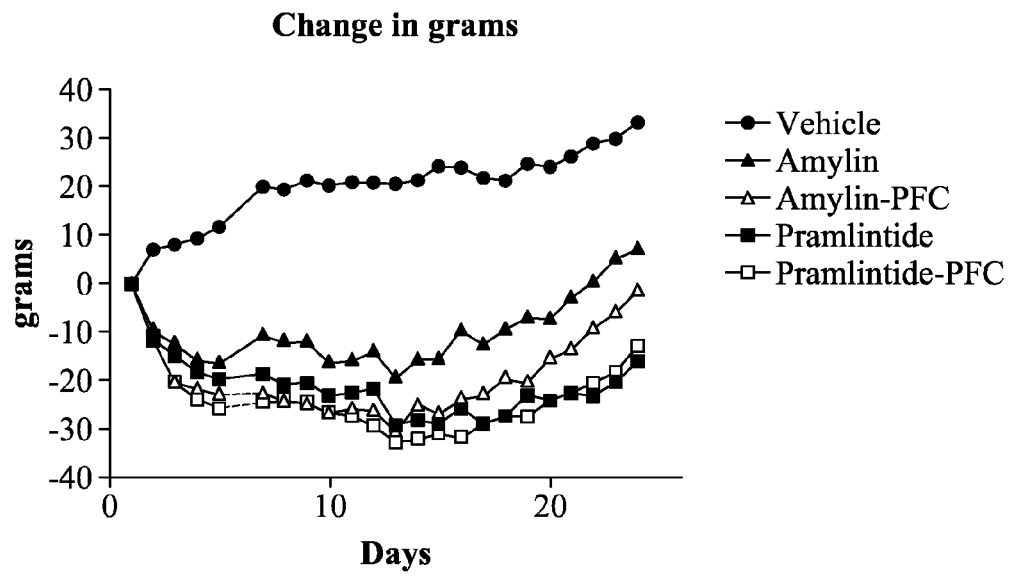
Figure 14D:
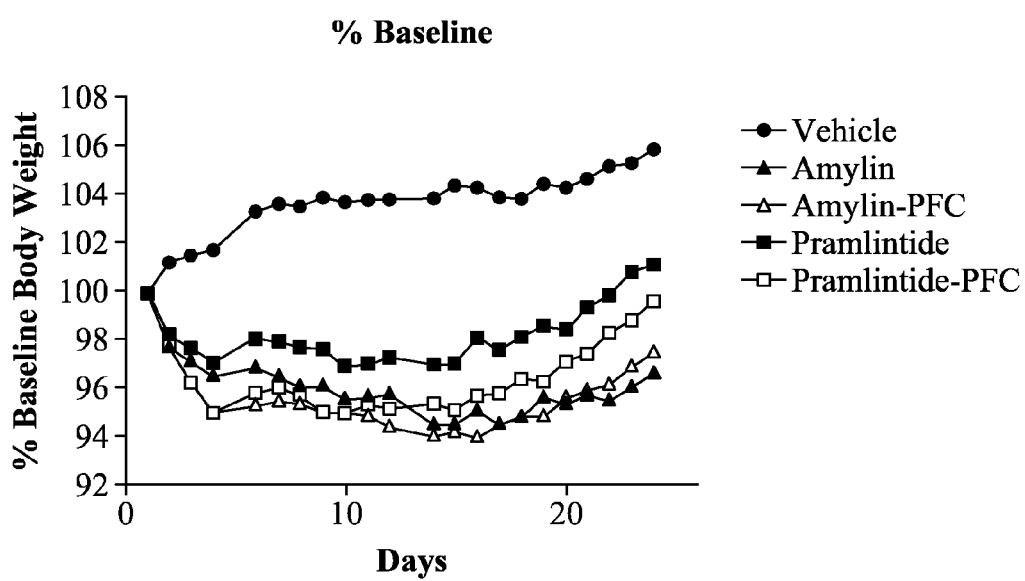
Figure 14E:
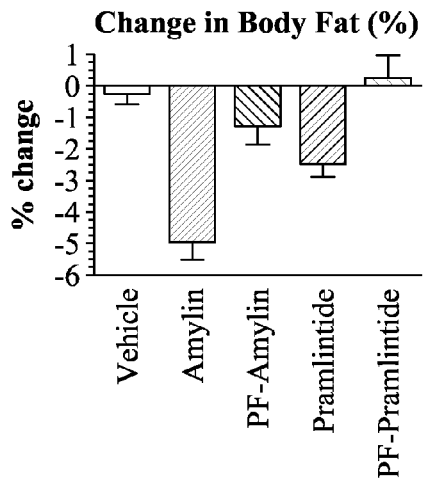
Figure 14F:
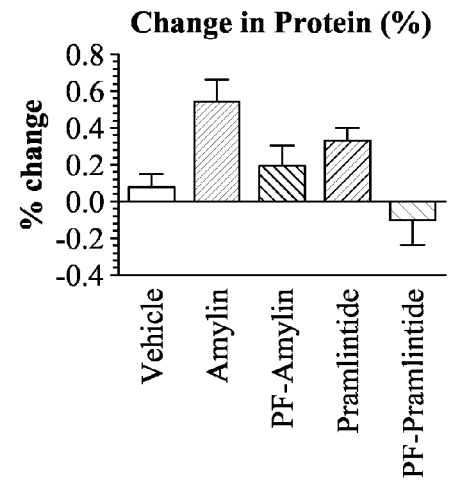
Figure 14G:
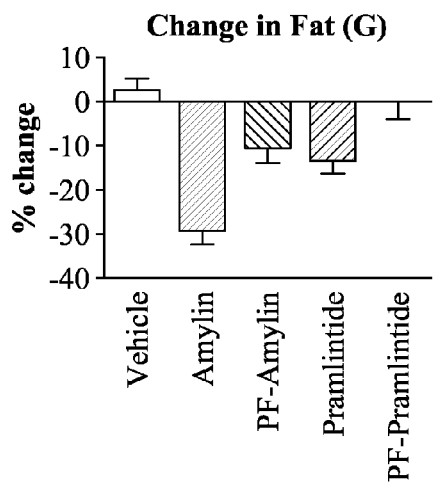
Figure 14H:
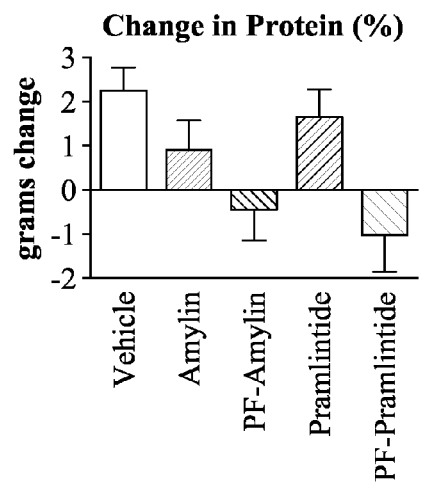

Changes in body weight and body composition are summarized in the table below and depicted in FIGS. 13A-13P. Amylin significantly reduced body weight under all treatment conditions. These changes in body weight were accompanied by significant decreases in percent body fat (except in chronically restricted animals—which approached statistical significance) and increases in percent protein (except in ad-lib fed then food restricted group). The ability of amylin to reduce body weight along with decreasing adiposity and/or preserving lean tissue can be extended to a variety of nutritive states in female rats.

TABLE 4

| Food access prior to treatment | Food access during treatment | Treatment (n) | Estimated Mean Weight change from treatment (g) | % Change in fat | % Change in protein |
|---|---|---|---|---|---|
| Ad-lib | Ad-lib | Vehicle (7) | −8.1 ± 1.4 | −5.9 ± 0.4 | 0.4 ± 0.1 |
|  |  | Amylin (7) | −21.8 ± 1.4 | −10.1 ± 0.5 | 0.8 ± 0.1 |
|  |  |  | (p < 0.001)* | (p < 0.001)* | (p = 0.007)* |
| Restricted | Restricted | Vehicle (7) | −9.3 ± 2.1 | −8.5 ± 0.5 | 0.5 ± 0.1 |
|  |  | Amylin (8) | −17.1 ± 2.0 | −11.1 ± 1.0 | 1.0 ± 0.1 |
|  |  |  | (p = .021)* | (p = 0.043) | (p = 0.001)* |
| Restricted | Ad-lib | Vehicle (8) | 3.5 ± 2.4 | −3.5 ± 0.6 | 0.3 ± 0.1 |
|  |  | Amylin (7) | −18.2 ± 2.5 | −11.5 ± 0.6 | 1.1 ± 0.1 |
|  |  |  | (p < 0.001)* | (p < 0.001)* | (p < 0.001)* |
| Ad-lib | Restricted | Vehicle (7) | −12.5 ± 2.3 | −7.6 ± 0.3 | 0.5 ± 0.1 |
|  |  | Amylin (6) | −23.1 ± 2.3 | −9.9 ± 0.9 | 0.7 ± 0.1 |
|  |  |  | (p = 0.007)* | (p = 0.017)* | (p = 0.463) |

*significant at 0.025 adjusted for the number of comparisons (one-tailed tests).

FIGS. 13A-13D depict the effect of amylin on body weight for each of the eight groups of rats. Amylin treated rats lost more weight than their vehicle treated counterparts. FIGS. 13E-13H depict the effect of amylin on food intake for each of the eight groups of rats. Amylin treated rats ate less than their vehicle treated counterparts. FIGS. 13I-13L depict the effect of amylin on body fat for each of the eight groups of rats. In general, amylin treated rats had a greater decrease in percent body fat than their vehicle treated counterparts. FIGS. 13M-13P depict the effect of amylin on dry lean mass for each of the eight groups of rats. In general, amylin treated rats had a greater increase in percent lean body mass than their vehicle treated counterparts.

Example 5

This experiment looked at the effect of amylin versus the effect of pramlintide (an amylin analog) on rats and also in comparison to pair-fed rats.

48 DIO Levin rats (an in-bred model of diet induced obesity) were used in this study. The rats were divided into five treatment groups (vehicle, n=10; amylin, n=10; pair-fed to amylin, n=9; pramlintide, n=10; pair-fed to pramlintide, n=9). The rats were treated with equimolar concentrations of pramlintide and amylin (76 nmol/kg/day or approximately 300 μg/kg/day) by osmotic mini-pump for 24 days. Food intake and body weight was measured daily. Vehicle, amylin and pramlintide-treated rats had ad-lib access to food during the study. The pair-fed groups were only allowed to consume the daily intakes of their respective drug-treated groups. For body composition, rats were scanned in a rodent NMR before treatment and after sacrifice (at the end of the study), allowing for the ability to calculate changes in carcass fat and protein (e.g., lean tissue). FIGS. 14A-14H depict results that show amylin and pramlintide having a significant effect on slowing body weight gain in this model and having favorable effects on body composition.

To assist in understanding the methods provided herein, the following further Examples 6-8 are included and describe the results of a series of experiments therein. The following examples should not, of course, be construed as specifically limiting the compounds and methods provided herein. Such variations, now known or later developed, which would be within the purview of one skilled in the art are considered to fall within the scope of the present invention.

Example 6

Preparation of $^{25,28,29}$Pro-h-Amylin

Peptides described herein can be synthesized by solid phase synthesis methods well known in the art. For example, solid phase synthesis of $^{25,28,29}$Pro-h-amylin using methyl-benzhydrylamine anchor-bond resin and $N^a$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved, the resin and side chain protecting groups were cleaved with liquid HF in the presence of dimethylsulfide and anisole. The $^{25,28,29}$Pro-h-amylin was purified by preparative reversed-phase HPLC. The peptide was found to be homogeneous by analytical HPLC and capillary electrophoresis and the structure was confirmed by amino acid analysis and sequence analysis. The product gave the desired mass ion. FAB mass spec: $(M+H)^+=3,949$.

Example 7

Receptor Binding Assay

Evaluation of the binding of compounds to amylin receptors was carried out as follows: $^{125}$I-rat amylin (Bolton-Hunter labeled at the N-terminal lysine) was purchased from Amersham Corporation (Arlington Heights, Ill.). Specific activities at time of use ranged from 1950 to 2000 Ci/mmol. Unlabeled peptides were obtained from BACHEM Inc. (Torrance, Calif.) and Peninsula Laboratories (Belmont, Calif.).

Male Sprague-Dawley rats (200-250) grams were sacrificed by decapitation. Brains were removed to cold phosphate-buffered saline (PBS). From the ventral surface, cuts were made rostral to the hypothalamus, bounded laterally by the olfactory tracts and extending at a 45° angle medially from these tracts. This basal forebrain tissue, containing the nucleus accumbens and surrounding regions, was weighed and homogenized in ice-cold 20 mM HEPES buffer (20 mM HEPES acid, pH adjusted to 7.4 with NaOH at 23° C.). Membranes were washed three times in fresh buffer by centrifugation for 15 minutes at 48,000×g. The final membrane pellet was resuspended in 20 mM HEPES buffer containing 0.2 mM phenylmethylsulfonyl fluoride (PMSF).

To measure $^{125}$I-amylin binding, membranes from 4 mg original wet weight of tissue were incubated with $^{125}$I-amylin at 12-16 pM in 20 mM HEPES buffer containing 0.5 mg/ml bacitracin, 0.5 mg/ml bovine serum albumin, and 0.2 mM PMSF. Solutions were incubated for 60 minutes at 23° C. Incubations were terminated by filtration through GFB glass fiber filters (Whatman Inc., Clifton, N.J.) which had been presoaked for 4 hours in 0.3% polyethyleneimine in order to reduce nonspecific binding of radiolabeled peptides. Filters were washed immediately before filtration with 5 ml cold PBS, and immediately after filtration with 15 ml cold PBS. Filters were removed and radioactivity assessed in a gamma-counter at a counting efficiency of 77%. Competition curves were generated by measuring binding in the presence of $10^{-12}$ to $10^{-6}$ M unlabeled test compound and were analyzed by nonlinear regression using a 4-parameter logistic equation (Inplot program; GraphPAD Software, San Diego).

In this assay, purified human amylin binds to its receptor at a measured $IC_{50}$ of about 50 pM. Results for test compounds are set forth in Table I, showing that each of the compounds has significant receptor binding activity.

Example 8

Soleus Muscle Assay

Evaluation of the amylin agonist activity of compounds was carried out using the soleus muscle assay as follows. Male Harlan Sprague-Dawley rats of approximately 200 g mass were used in order to maintain mass of the split soleus muscle less than 40 mg. The animals were fasted for 4 hours prior to sacrifice by decapitation. The skin was stripped from the lower limb which was then pinned out on corkboard. The tendo achilles was cut just above os calcis and *m. gastrocnemius* reflected out from the posterior aspect of the tibia. *M. soleus*, a small 15-20 mm long, 0.5 mm thick flat muscle on the bone surface of *m. gastrocnemius* was then stripped clear and the perimysium cleaned off using fine scissors and forceps. *M. soleus* was then split into equal parts using a blade passed antero-posteriorly through the belly of the muscle to obtain a total of 4 muscle strips from each animal. After dissecting the muscle from the animal, it was kept for a short period in physiological saline. It was not necessary that the muscle be held under tension as this had no demonstable effects on radioglucose incorporation into glycogen.

Muscles were added to 50 mL Erlenmeyer flasks containing 10 mL of a pregassed Krebs-Ringer bicarbonate buffer containing (each liter) NaCl 118.5 mmol (6.93 g), KCl 15.94 mmol (443 mg), CaCl$_2$ 2.54 mmol (282 mg), MgSO$_4$ 1.19 mmol (143 mg), KH$_2$PO$_4$ 1.19 mmol (162 mg), NaHCO$_3$ 25 mmol (2.1 g), 5.5 mmol glucose (1 g) and recombinant human insulin (Humulin-R, Eli Lilly, Ind.) and the test compound, as detailed below. pH at 37° C. was verified as being between 7.1 and 7.4. Muscles were assigned to different flasks so that the 4 muscle pieces from each animal were evenly distributed among the different assay conditions. The incubation media were gassed by gently blowing carbogen (95% O$_2$, 5% CO$_2$) over the surface while being continuously agitated at 37° C. in an oscillating water bath. After a half-hour "preincubation" period, 0.5 μCi of U-$^{14}$C-glucose was added to each flask which was incubated for a further 60 minutes. Each muscle piece was then rapidly removed, blotted and frozen in liquid N$_2$, weighed and stored for subsequent determination of $^{14}$C-glycogen.

$^{14}$C-glycogen determination was performed in a 7 mL scintillation vial. Each frozen muscle specimen was placed in a vial and digested in 1 mL 60% potassium hydroxide at 70° C. for 45 minutes under continuous agitation. Dissolved glycogen was precipitated out onto the vial by the addition of 3 mL absolute ethanol and overnight cooling at −20° C. The supernatant was gently aspirated, the glycogen washed again with ethanol, aspirated and the precipitate dried under vacuum. All ethanol is evaporated to avoid quenching during scintillation counting. The remaining glycogen was redissolved in 1 mL water and 4 mL scintillation fluid and counted for $^{14}$C.

The rate of glucose incorporation into glycogen (expressed in μmol/g/hr) was obtained from the specific activity of $^{14}$C-glucose in the 5.5 mM glucose of the incubation medium, and the total $^{14}$C counts remaining in the glycogen extracted from each muscle. Dose/response curves were fitted to a 4-parameter logistic model using a least-squares iterative routine (ALLFIT, v2.7, NIH, MD) to derive $EC_{50}$'s. Since $EC_{50}$ is log-normally distributed, it is expressed±standard error of the logarithm. Pairwise comparisons were performed using t-test based routines of SYSTAT (Wilkinson, "SYSTAT: the system for statistics," SYSTAT Inc., Evanston, Ill. (1989)).

Dose response curves were generated with muscles added to media containing 7.1 nM (1000 μU/mL) insulin and each test compound added at final (nominal) concentrations of 0, 1, 3, 10, 30, 100, 300 and 1000 nM. Each assay also contained internal positive controls consisting of a single batch of archived rat amylin, lyophilized and stored at −70° C.

Human amylin is a known hyperglycemic peptide, and $EC_{50}$ measurements of amylin preparations in the soleus muscle assay range typically from about 1-10 nM, although some commercial preparations which are less than 90% pure have higher $EC_{50}$'s due to the presence of contaminants that result in a lower measured activity. Results for test compounds are set forth in Table 5, showing that each of the compounds has amylin activity.

TABLE 5

| No. | Compound | Receptor Binding Assay $IC_{50}$(pM) | Soleus Muscle Assay $EC_{50}$(nM) |
|---|---|---|---|
| 1) | $^{28}$Pro-h-Amylin | 15.0 | 2.64 |
| 2) | $^{25}$Pro$^{26}$Val$^{28, 29}$Pro-h-Amylin | 18.0 | 4.68 |
| 3) | $^{2, 7}$Cyclo-[$^2$Asp,$^7$Lys]-h-Amylin | 310.0 | 6.62 |
| 4) | $^{2, 37}$h-Amylin | 236.0 | 1.63 |
| 5) | $^1$Ala-h-Amylin | 148.0 | 12.78 |
| 6) | $^1$Ser-h-Amylin | 33.0 | 8.70 |
| 7) | $^{29}$Pro-h-Amylin | 64.0 | 3.75 |
| 8) | $^{25, 28}$Pro-h-Amylin | 26.0 | 13.20 |
| 9) | des-$^1$Lys$^{25, 28}$Pro-h-Amylin | 85.0 | 7.70 |
| 10) | $^{18}$Arg$^{25, 28}$Pro-h-Amylin | 32.0 | 2.83 |
| 11) | des-$^1$Lys$^{18}$Arg$^{25, 28}$Pro-h-Amylin | 82.0 | 3.77 |
| 12) | $^{18}$Arg$^{25, 28, 29}$Pro-h-Amylin | 21.0 | 1.25 |
| 13) | des-$^1$Lys$^{18}$Arg$^{25, 28, 29}$Pro-h-Amylin | 21.0 | 1.86 |
| 14) | $^{25, 28, 29}$Pro-h-Amylin | 10.0 | 3.71 |
| 15) | des-$^1$Lys$^{25, 28, 29}$Pro-h-Amylin | 14.0 | 4.15 |

Clinical investigations described herein were conducted in compliance with current Good Clinical Practice (GCP) and the United States of America Code of Federal Regulations (CFR) Title 21 Part 56 relating to institutional review boards (IRBs). An IRB reviewed the study protocol and protocol amendments. All clinical studies were conducted in accordance with the "Recommendations Guiding Medical Doctors in Biomedical Research Involving Human Subjects" contained in the Declaration of Helsinki (1964), including all amendments up to and including the South Africa revision (1996). All clinical studies were conducted in compliance with CFR Title 21 Part 50 pertaining to informed consent and the Health Insurance Portability and Accountability Act (HIPAA) of 1996, as amended to protect patients' protected health information (PHI). At the first visit (Screening) of each study, prior to initiation of any study-related procedures, subjects gave their written informed consent to participate in the study and completed a HIPAA Authorization form (where applicable) to authorize the use and disclosure of their PHI after having been informed about the nature and purpose of the study, participation/termination conditions, and risks and benefits.

Abbreviations used herein include the following: ATC: Anatomic Therapeutic Chemistry; AUC: area under the concentration-time curve; BMI: body mass index; CFR: Code of Federal Regulations; $C_{max}$: maximum concentration observed during the blood sampling period; eCRF: electronic case report form; CRM: Continual Reassessment Method; CV: coefficient of variation; ECG: electrocardiogram; FDA: Food and Drug Administration; GCP: Good Clinical Practice; HBV: hepatitis B virus; HCV: hepatitis C virus; HIPAA: Health Information Portability and Accountability Act; HIV: human immunodeficiency virus; iAUC: incremental AUC; ICH: International Conference on Harmonisation; $iC_{max}$: maximum increment in concentration from the concentration at baseline; IRB: institutional review board; ITT: intent-to-treat; LLOQ: lower limit of quantitation; MedDRA: Medical Dictionary for Regulatory Activities; PHI: protected health information; PD: pharmacodynamic; PK: pharmacokinetic; SAP: statistical analysis plan; SC: subcutaneous; SD: standard deviation; SE: standard error; $t_{1/2}$: terminal half-life; $T_{max}$: time of the first observed maximum concentration.

Example 9

A randomized, single-blind, placebo-controlled, single-dose, dose-ranging study was conducted to evaluate the safety, tolerability, and pharmacokinetics of single doses of davalintide administered by subcutaneous (SC) injection to obese subjects with no other major health problems. Doses ranging from 0.03 mcg/kg to 10.0 mcg/kg were examined, with dosing in each cohort, subsequent to the initial cohort, based on clinical assessment of the safety and tolerability data from the previous cohort(s).

Study medication was investigated in consecutive cohorts of subjects, each comprising four individuals, according to a progressive dose escalation scheme, with planned davalintide doses of 0.03, 0.1, 0.3, 1, 3, and 10 mcg/kg. Doses were to be tested in up to 12 cohorts, with a maximum number of 48 subjects exposed to study medication. After the initial cohort, decisions concerning dosing of each subsequent cohort were made based on the clinical assessment of the safety and tolerability data from the previous cohort(s) and were guided by the Continual Reassessment Method. The protocol allowed for each cohort to be studied at either the same dose as the previous cohort, the next planned higher or lower dose, or a dose intermediate to the planned doses. The dosing rationale for this study was guided mainly by data from completed nonclinical pharmacology and toxicology studies. Specifically, it was based on the no observed adverse effect level (NOAEL) of 20 mcg/kg/day davalintide (administered SC twice daily for 14 days) in dogs, which corresponds to a human equivalent dose (HED), based on allometric conversion, of approximately 8 mcg/kg/day (or an 800-mcg total dose in a 100-kg human), according to FDA guidelines on estimating the maximum safe starting dose in initial clinical trials for therapeutics.

After the first dosing cohort was completed, the investigator, in consultation with the sponsor, determined each subsequent dose level based on the clinical assessment of the safety and tolerability data from the previous cohorts. The protocol allowed for each cohort to be studied at either the same dose as the previous cohort, the next planned higher or lower dose, or a dose intermediate to the planned doses, to enable a better understanding of potential adverse events. As a result of the clinical and CRM evaluation of each cohort, doses of 0.03, 0.1, 0.3, 0.6, 1.5, 3, 4.5, and 6 mcg/kg were examined. For calculation of davalintide doses, the subjects' body weight at Day −1 was employed.

Davalintide injection was formulated as a sterile, nonpreserved, clear, colorless, aqueous solution buffered to a pH of 4.0 for SC injection. Mannitol was added as a tonicity modifier. The concentration of davalintide injection used in this study was 1.0 mg/mL. Placebo was the same sterile formulation except that it does not contain the active ingredient, davalintide.

Subject eligibility was determined at screening (Visit 1) and on Day −1 (Visit 2). Eligible subjects were males or nonpregnant, nonlactating females; 19 to 55 years old; obese with a body mass index (BMI) from 30 kg/m$^2$ to 45 kg/m$^2$, and with no other major health problems as judged by the investigator. Females of childbearing potential were required to use appropriate contraceptive methods throughout the study.

The randomized population consisted of all randomized subjects. The Intent-to-Treat (ITT) population consisted of all randomized subjects who received an injection of study medication (davalintide or placebo). The Evaluable Population consisted of all ITT subjects who had adequate data for reliable evaluation of PK parameters. A minimum of three post-dose plasma davalintide concentration values were required for a subject's data to be considered adequate.

The study consisted of an inpatient period of approximately 24 hours (Day −1 through Day 1); following study termination, subjects remained under observation for approximately 12 hours to allow for monitoring of any residual effects of the study medication. Subjects deemed eligible based on screening were admitted to the study site on Day −1 and remained domiciled for approximately 36 hours through the 12-hour observation period. On dosing day (Day 1), subjects in each dosing cohort were randomly assigned to receive either a single dose of davalintide or an equivalent placebo volume in a 3:1 ratio (davalintide:placebo). Study medication was administered by SC injection 15 minutes prior to a standardized breakfast. Pharmacokinetic, pharmacodynamic (PD), and safety assessments were performed for up to approximately 12 hours post-dose. Plasma concentration measurements of davalintide were measured using a validated immunoenzymetric assay.

Figure 15:
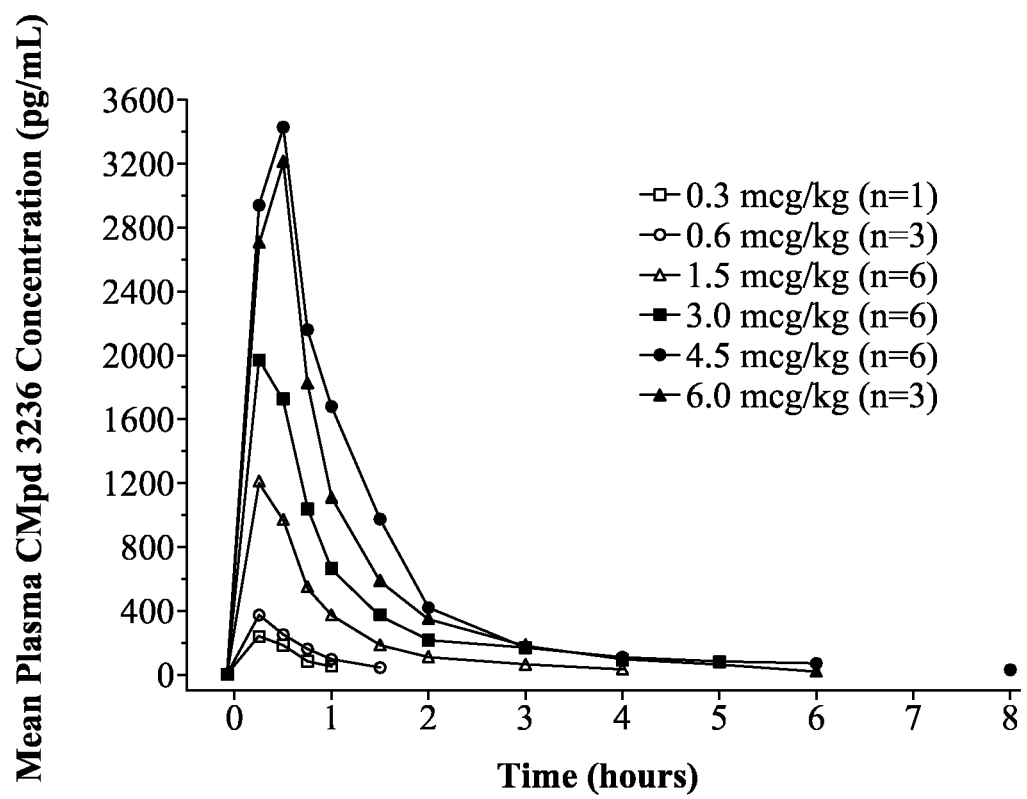
FIG. 15 depicts the mean plasma concentration-time profiles of davalintide (SEQ ID NO:138) on a linear scale following a single SC injection of davalintide at doses of 0.3, 0.6, 1.5, 3, 4.5, and 6 mcg/kg.

FIG. 15 depicts the mean plasma davalintide concentration-time profiles on a linear scale following a single SC injection of davalintide at doses of 0.3, 0.6, 1.5, 3, 4.5, and 6 mcg/kg. Plasma davalintide concentrations for the 0.03 mcg/kg and 0.1 mcg/kg doses were generally below the LLOQ in all subjects and are not provided in FIG. 15 or Table 6. Descriptive statistics for the mean PK parameters area under the concentration-time curve from time zero to infinity (AUC$_{(0-\infty)}$), maximum concentration observed during the 12-hour sampling period (C$_{max}$), time of the first observed maximum concentration (T$_{max}$), and terminal half-life (t$_{1/2}$), calculated for the 0.3 mcg/kg to 6 mcg/kg doses, are presented in Table 6.

As shown in Table 6, mean AUC$_{(0-\infty)}$ and C$_{max}$ values increased with increasing doses from 0.3 mcg/kg to 4.5 mcg/ kg. Exposure, in terms of $AUC_{(0-\infty)}$ and $C_{max}$, was similar for the 4.5 mcg/kg and 6 mcg/kg doses, with the range of individual $AUC_{(0-\infty)}$ and $C_{max}$ values for the 6 mcg/kg dose distributed within the range of the respective values for the 4.5 mcg/kg dose. Median $T_{max}$ values ranged between 0.25 hours and 0.5 hours, and median $t_{1/2}$ values ranged between 0.3 hours and 1.6 hours; there was a trend toward higher $T_{max}$ values at the highest doses (4.5 mcg/kg and 6 mcg/kg) and higher $t_{1/2}$ values for doses higher than 0.6 mcg/kg.

within the normal ranges at study termination (time≥12 hours post-dose) in all dose groups. Mild sinus tachycardia was reported in one of three subjects administered the 0.1 mcg/kg davalintide dose, one of six subjects administered the 1.5 mcg/kg dose, and four of six subjects administered the 4.5 mcg/kg dose; all other ECG parameters in these subjects were within the normal ranges. No safety concerns emerged at any of the davalintide doses tested. No deaths occurred and no serious adverse events were reported during the study.

TABLE 6

Pharmacokinetic Results of single-dose, dose-ranging study: davalintide

| Parameter Statistics | 0.3 mcg/kg (N = 1) | 0.6 mcg/kg (N = 3) | 1.5 mcg/kg (N = 6) | 3 mcg/kg (N = 6) | 4.5 mcg/kg (N = 6) | 6 mcg/kg (N = 3) |
|---|---|---|---|---|---|---|
| **AUC(0-∞) (pg*h/mL)** | | | | | | |
| Mean (SD) | 153.7 (—) | 261.5 (48.62) | 1111.7 (439.22) | 2109.4 (1410.3) | 4072.5 (2120.3) | 3364.4 (815.93) |
| CV % | — | 18.6 | 39.5 | 66.9 | 52.1 | 24.3 |
| Median | 153.7 | 275.6 | 1154.3 | 1434.5 | 3736.7 | 3213.7 |
| Min, Max | 153.7, 153.7 | 207.3, 301.4 | 368.7, 1747.6 | 912.9, 4228.5 | 1623.9, 7032.1 | 2634.3, 4245.1 |
| $C_{max}$ (pg/mL) | | | | | | |
| Mean (SD) | 238.0 (—) | 339.3 (110.62) | 1217.0 (436.04) | 2121.7 (828.14) | 3745.0 (1354.2) | 3213.3 (771.51) |
| CV % | — | 32.6 | 35.8 | 39.0 | 36.2 | 24.0 |
| Median | 238.0 | 279.0 | 1302.5 | 2165.0 | 3510.0 | 3060.0 |
| Min, Max | 238.0, 238.0 | 272.0, 467.0 | 462.0, 1670.0 | 1080.0, 3370.0 | 2240.0, 5380.0 | 2530.0, 4050.0 |
| $T_{max}$ (h) | | | | | | |
| Mean (SD) | 0.25 (—) | 0.34 (0.14) | 0.29 (0.10) | 0.34 (0.14) | 0.38 (0.14) | 0.50 (0.00) |
| CV % | — | 41.2 | 34.3 | 41.8 | 36.5 | 0.0 |
| Median | 0.25 | 0.27 | 0.25 | 0.25 | 0.38 | 0.50 |
| Min, Max | 0.3, 0.3 | 0.3, 0.5 | 0.3, 0.5 | 0.3, 0.6 | 0.3, 0.5 | 0.5, 0.5 |
| $t_{1/2}$ (h) | | | | | | |
| Mean (SD) | 0.3 (—) | 0.4 (0.07) | 0.9 (0.57) | 1.6 (1.63) | 1.9 (1.20) | 1.0 (0.12) |
| CV % | — | 15.7 | 60.2 | 103.4 | 64.2 | 11.7 |
| Median | 0.3 | 0.4 | 0.8 | 0.6 | 1.6 | 1.0 |
| Min, Max | 0.3, 0.3 | 0.4, 0.5 | 0.5, 2.1 | 0.4, 4.0 | 0.7, 3.6 | 0.9, 1.2 |

Plasma glucose concentrations were measured prior to and over a period of approximately 4.75 hours after a standardized meal (administered at time=0.25 h relative to study medication injection [time=0 h]). Seventeen of the 33 davalintide-treated ITT subjects ate less than 50% of their allocated amount (based on individual caloric requirements), and 7 of the 11 placebo-treated subjects also ate less than their allocated amount of the standardized meal.

No serious adverse events were reported during this study. No subjects were withdrawn due to a treatment-emergent adverse event in this study. There were no clinically significant changes or trends from baseline to study termination in mean or individual values for hematology, chemistry, or urinalysis in any dose groups. There were no clinically significant changes or trends from baseline in mean or individual values for serum electrolyte concentrations over the 12-hour post-dose observation period in any dose groups. There were no clinically significant changes from baseline to study termination in physical examination findings in any dose groups. During the 12-hour post-dose observation period, there were no clinically significant changes or trends from baseline in mean or individual values for systolic or diastolic blood pressure, temperature, or ECG parameters, except for heart rate, in any dose groups. Changes in mean heart rate ranging from −6.0 bpm to 23.5 bpm were documented (by either measurement of vital signs or ECG) during the 12-hour post-dose observation period, but mean values were generally Example 10

Figures 16, 17:
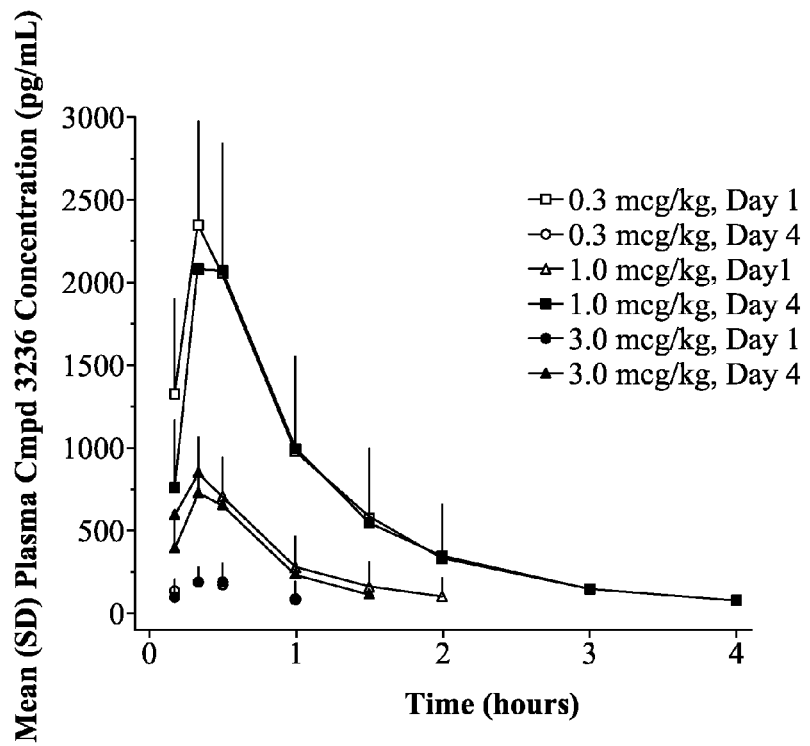
FIG. 16 depicts a 4×4 Latin Square/Williams design for the experiment described in Example 10.
FIG. 17 depicts the mean plasma davalintide (SEQ ID NO:138) concentration-time profile on a linear scale following SC injection of davalintide at doses of 0.3, 1, and 3 mcg/kg, administered as four treatment sequences in a crossover fashion, with each treatment (0.3, 1, and 3 mcg/kg, and placebo) administered during a 4-day period.

A randomized, single-blind, placebo-controlled, multi-dose, four-period, crossover study was conducted to evaluate the safety, tolerability, and pharmacokinetics of davalintide administered by SC injection to obese subjects. The study was conducted at a single clinical study site and consisted of an 18-day inpatient period (Day −1 to Day 17). Eligible subjects (based on screening) were admitted to the study site on Day −1. On Day 1, subjects were enrolled and randomized to one of eight treatment sequences, A, B, C, D, E, F, G, or H, in a ratio of 4:4:4:4:1:1:1:1. See FIG. 16. Randomization was stratified by screening body mass index (BMI) (<35 kg/m² versus≥35 kg/m²) to ensure a 1:1:1:1 ratio for treatment sequences A, B, C, and D within each BMI stratum. Subjects in treatment sequences A, B, C, and D received four separate treatments (one dose of placebo [3 μL/kg] and three doses of davalintide [0.3, 1, and 3 mcg/kg]) over four 4-day periods (I, II, III, and IV), according to a 4×4 Latin Square/Williams design (FIG. 16). Subjects randomized to treatment sequences E, F, G, and H received weight-adjusted placebo injection volumes corresponding to the volumes of study medication (davalintide or placebo) administered in treatment sequences A, B, C, and D, respectively. With reference to FIG. 16, subjects in treatment sequences A, B, C, and D received davalintide and placebo in a crossover fashion; subjects in treatment sequences E, F, G, and H received weight-adjusted placebo injection volumes corresponding to the volumes of study medication (davalintide or placebo) administered in treatment sequences A, B, C, and D, respectively. The dose and volume per injection was calculated using the subject's body weight recorded at Day −1 (Visit 2). The placebo-only sequences were included in the study design for safety comparisons and blinding purposes. Study medication (davalintide or placebo) was administered by SC injection ~15 min prior to the morning and evening meals; the injections were ~10 h apart. Pharmacokinetic (PK), pharmacodynamic (PD) and safety assessments were performed on select study days for up to 12 h after the morning dose of study medication.

The planned sample size was 20 individuals (4 subjects to be randomized to each of the treatment sequences A, B, C, and D; and 1 subject to be randomized to each of the treatment sequences E, F, G, and H), as shown in the FIG. 16. A total of 18 subjects were randomized to treatment, 14 subjects in the davalintide treatment sequences A, B, C, and D, and 4 subjects in the pooled placebo group treatment sequences E, F, G, and H combined. All 18 subjects completed the study; there were no early withdrawals. Since all randomized subjects received an injection of study medication, the Randomized and ITT Populations are identical and include all 18 subjects. The evaluable population included, by definition, only davalintide-treated subjects, and all 14 subjects assigned to the davalintide treatment sequences were considered evaluable.

Study subjects were males or nonpregnant, nonlactating females 19 to 55 years old, obese with a BMI≥30 kg/m$^2$ to ≥45 kg/m$^2$ at screening, and with no other major health problems as judged by the investigator. Females of childbearing potential were required to use appropriate contraceptive methods throughout the study.

Plasma davalintide concentrations were measured from blood samples collected from davalintide-treated subjects on the first and fourth day of each treatment period (Days 1, 4, 5, 8, 9, 12, 13, and 16) prior to and over ~8 h after the morning dose of study medication.

Caloric intake was measured daily from ad libitum breakfast, lunch, dinner, and optional evening snack, which were served at pre-specified times (~0.25 h, 4.25 h, 10.25 h, and 13.25 h±15 min, respectively) relative to the morning dose of study medication (time=0 h) on each of the 16 days of treatment (Day 1 through Day 16).

Subjective ratings of hunger, fullness, and nausea were obtained on 100-mm Visual Analog Scales (VAS) repeatedly over ~12 h, beginning 0.25 h prior to the morning dose of study medication, on the last day of each 4-day period (Days 4, 8, 12, and 16).

For data summarization, the placebo sequences E, F, G, and H were combined and treated as a single sequence; data from the placebo period in sequences A, B, C, and D were combined and, similarly, data from each of the three davalintide doses administered during treatment sequences A, B, C, and D were combined across the sequences when appropriate. Data were summarized descriptively by treatment (0.3, 1, and 3 mcg/kg, and within-sequence placebo; and each corresponding placebo volume) and, as appropriate, by sequence or relative day within each period. A minimum of three quantifiable values was required to calculate the PK parameters.

PK analyses were performed for the evaluable population. For each treatment, data across sequences were pooled appropriately for data summarization and analysis. Noncompartmental PK parameters for plasma davalintide concentrations were calculated and summarized for each davalintide dose by relative day within each period. To investigate the occurrence of drug accumulation, 95% confidence intervals (CIs) for the ratio of AUC on Day 4 to that on Day 1 of each treatment period were constructed based on a mixed-effect model for the log-transformed values with a factor for relative day of the period and a random effect for subject.

The study was powered for changes in daily total caloric intake. PD analyses were performed for the Evaluable Population; data summaries were also produced for the ITT Population. The daily caloric intake was summarized by treatment (0.3, 1, and 3 mcg/kg, and within-sequence placebo) and relative day within each period. For each subject in sequences A, B, C, and D, the average caloric intake at each meal (breakfast, lunch, dinner, or evening snack) and over 24 h across the 4 days of each treatment period was calculated and summarized by treatment, and the difference between the mean average daily caloric intake associated with each davalintide treatment and that of the within-sequence placebo treatment was tested using a repeated-measure analysis of variance (ANOVA) model with factors for treatment, period, and sequence; and an unstructured variance-covariance matrix for the repeated measures from the same subject. Additionally, the average daily caloric intake across the 4 days of each treatment period was calculated and summarized by treatment for each davalintide sequence (A, B, C, and D). A post-hoc analysis was conducted to test whether the absolute change by meal and percent change in daily and by-meal average caloric intake between each davalintide treatment and the within-sequence placebo treatment were statistically significant; percentages were estimated based on a repeated-measure ANOVA model for log-transformed data. Noncompartmental PD parameters for hunger, fullness, and nausea were calculated for each subject and summarized for each treatment (0.3, 1, and 3 mcg/kg, and within-sequence placebo; and corresponding placebo volumes). For each of these assessments, the difference between the mean areas under the VAS rating curve over the 12-h observation period ($AUC_{(-0.25-12.25\,h)}$) associated with each davalintide treatment and that of the within-sequence placebo treatment was tested in a similar manner as for mean average daily caloric intake.

Following subcutaneous injection of davalintide (morning dose), the mean PK profiles of plasma davalintide for each dose (0.3, 1, and 3 mcg/kg) on Day 1 and Day 4 were generally similar. Mean plasma davalintide concentrations for all doses increased rapidly, peaking at ~0.33 h (20 min) after injection, and declined steadily thereafter through the 8-h blood sampling period. Mean plasma davalintide concentrations increased with increasing doses.

As shown in Table 7 and consistent with the PK profile, mean AUC and $C_{max}$ values increased with increasing doses. Mean $AUC_{(0-tlast)}$, $AUC_{(0-\infty)}$, and $C_{max}$ for the 0.3 mcg/kg and 3 mcg/kg doses on Day 1 and Day 4 were similar. Although mean $AUC_{(0-tlast)}$ and $AUC_{(0-\infty)}$ for the 1 mcg/kg dose were higher on Day 4 compared with Day 1 (p=0.0015 and 0.0030, respectively), these differences are unlikely to reflect drug accumulation, given the short half-life of Cmpd 3236 ($t_{1/2}$<1 h for this dose) and the dosing frequency (BID). Median $T_{max}$ and $t_{1/2}$ values of Cmpd 3236 concentrations were similar on Day 1 and Day 4 for each dose.

TABLE 7

Pharmacokinetic results of plasma Cmpd 3236 concentrations following SC administration by dose.

| Parameter | DAY 1 | | | DAY 4 | | |
|---|---|---|---|---|---|---|
| | 0.3 mcg/kg (N = 14) | 1 mcg/kg (N = 14) | 3 mcg/kg (N = 14) | 0.3 mcg/kg (N = 14) | 1 mcg/kg (N = 14) | 3 mcg/kg (N = 14) |
| $AUC_{(0-tlast)}$ (pg*h/mL)[1] | | | | | | |
| Mean (SD) | 198.80 (154.51) | 665.83 (338.05) | 2499.57 (1208.83) | 190.25 (121.35) | 825.31 (387.61) | 2681.27 (1082.71) |
| Median | 152.93 | 580.42 | 2147.17 | 154.71 | 727.83 | 2359.88 |
| Min, Max | 39.50, 580.17 | 333.50, 1512.67 | 1017.17, 5287.25 | 76.25, 493.92 | 403.25, 1702.92 | 1338.50, 4641.50 |
| $AUC_{(0-\infty)}$ (pg*h/mL)[2] | | | | | | |
| Mean (SD) | 318.46 (157.01) | 651.69 (259.09) | 2568.16 (1217.41) | 250.47 (145.65) | 877.42 (411.66) | 2802.58 (1123.44) |
| Median | 311.65 | 556.57 | 2219.51 | 199.22 | 784.39 | 2436.08 |
| Min, Max | 131.80, 614.76 | 355.15, 1130.00 | 1035.84, 5343.03 | 96.00, 552.73 | 425.55, 1775.90 | 1464.04, 4767.18 |
| $C_{max}$ (pg/mL) | | | | | | |
| Mean (SD) | 226.21 (108.71) | 788.57 (253.11) | 2223.57 (705.15) | 210.79 (75.61) | 872.50 (196.78) | 2421.43 (671.90) |
| Median | 217.50 | 752.50 | 2025.00 | 212.00 | 832.50 | 2505.00 |
| Min, Max | 92, 493 | 350, 1410 | 1270, 4310 | 100, 402 | 585, 1320 | 1250, 3440 |
| $T_{max}$ (h) | | | | | | |
| Mean (SD) | 0.37 (0.08) | 0.38 (0.11) | 0.42 (0.09) | 0.30 (0.12) | 0.31 (0.09) | 0.37 (0.10) |
| Median | 0.33 | 0.33 | 0.42 | 0.33 | 0.33 | 0.33 |
| Min, Max | 0.25, 0.50 | 0.20, 0.62 | 0.33, 0.53 | 0.17, 0.50 | 0.17, 0.50 | 0.17, 0.50 |
| $t_{1/2}$ (h)[3] | | | | | | |
| Mean (SD) | 0.60 (0.18) | 0.64 (0.34) | 0.99 (0.38) | 0.61 (0.29) | 0.74 (0.34) | 1.33 (0.50) |
| Median | 0.57 | 0.59 | 00.96 | 0.53 | 0.65 | 1.16 |
| Min, Max | 0.40, 1.00 | 0.31, 1.36 | 0.34, 1.99 | 0.26, 1.31 | 0.29, 1.45 | 0.73, 2.34 |

[1]Area under the concentration-time curve from time 0 to the time of the last quantifiable sample.
[2]Day 1: N = 8 for 0.3 mcg/kg, and N = 13 for 1 mcg/kg; Day 4: N = 11 for 0.3 mcg/kg, and N = 13 for 3 mcg/kg.
[3]Day 1: N = 8 for 0.3 mcg/kg, and N = 13 for 1 mcg/kg; Day 4: N = 11 for 3 mcg/kg, and N = 13 for 3 mcg/kg.

FIG. 17 depicts the mean plasma Cmpd 3236 concentration-time profile on a linear scale following SC injection of Cmpd 3236 at doses of 0.3, 1, and 3 mcg/kg, administered as four treatment sequences in a crossover fashion, with each treatment (Cmpd 3236 0.3, 1, and 3 mcg/kg, and placebo) administered during a 4-day period. Pharmacokinetic analysis was performed from blood collected prior to and over ~8 hours after the morning dose of study medication on Day 1 and Day 4 of each treatment period. For each treatment, data across sequences were pooled for summarization and analysis. Data points shown in FIG. 17 are those with quantifiable values from at least 9 of the 14 evaluable subjects. Following SC injection of davalintide (morning dose), the mean PK profiles of plasma davalintide for each dose (0.3, 1, and 3 mcg/kg) on Day 1 and Day 4 were generally similar. Mean plasma davalintide concentrations for all doses increased rapidly, peaking at approximately 0.33 hours (20 minutes) after injection, and declined steadily thereafter through the 8-hour blood sampling period. Mean plasma Davalintide concentrations increased with increasing doses.

Statistically significant absolute and percent reductions in mean average daily caloric intake were observed with all Davalintide treatments compared with the within-sequence placebo treatment. The LS mean reductions from placebo amounted to ~401 kcal (p=0.0117) (~15%, p=0.0290), ~378 kcal (p=0.0003) (~14%, p=0.0015), and ~1068 kcal (p<0.0001) (~36%, p<0.0001) with 0.3, 1, and 3 mcg/kg BID, respectively. For all Davalintide treatments, the cumulative reductions in daily caloric intake were attributable to reductions in caloric intake at each meal (breakfast, lunch, dinner, and evening snack). Although these reductions did not reach statistical significance in all cases, they were statistically significant at each meal at the highest dosage (3 mcg/kg BID).

Mean hunger and fullness rating profiles for each Davalintide treatment (0.3, 1, and 3 mcg/kg) and for the within-sequence placebo treatment were similar. Consistent with the mean hunger and fullness rating profiles, there were no statistically significant differences in LS mean $AUC_{(-0.25-12.25\,h)}$ or LS mean maximum VAS rating for hunger or fullness for each Davalintide treatment compared with the within-sequence placebo treatment. Similar results were observed for mean nausea rating profiles, and LS mean $AUC_{(-0.25-12.25\,h)}$ and maximum VAS rating for nausea.

As shown in Table 8, average daily total caloric intake over four days of each period (averaged for each subject) decreases at a 3 mcg/kg level relative to 1 mcg/kg dosage.

TABLE 8

Average Daily Total Caloric Intake Pharmacodynamic Parameters - Inferential Statistics

| Average Daily Total Caloric Intake (kcal) [2]/ Comparison Pair/ Statistics | 0.3 mcg/kg (N = 14) | 1 mcg/kg (N = 14) | 3 mcg/kg (N = 14) |
|---|---|---|---|
| Davalintide dose/ Placebo (%) [1] | | | |
| N | 14 | 14 | 14 |
| Mean (SD) | −13.2 (18.28) | −10.7 (18.62) | −32.0 (19.55) |
| SE | 4.89 | 4.98 | 5.22 |
| Median | −4.1 | −8.5 | −34.1 |
| Min, Max | −49.7, 7.1 | −39.0, 16.3 | −59.3, 10.6 |

TABLE 8-continued

Average Daily Total Caloric Intake Pharmacodynamic
Parameters - Inferential Statistics

| Average Daily Total Caloric Intake (kcal) [2]/ Comparison Pair/ Statistics | 0.3 mcg/kg (N = 14) | 1 mcg/kg (N = 14) | 3 mcg/kg (N = 14) |
|---|---|---|---|
| Estimate of Percent Change from Placebo [2] | −15.39 | −14.38 | −35.91 |
| 95% CI [2] | −26.95, −2.01 | −21.04, −7.15 | −45.42, −24.75 |
| p-value [2] | 0.0290 | 0.0015 | <.0001 |

[1] Data over four days of each period were averaged for each subject prior to summarization or model fitting.
[2] Based on a repeated measures analysis of variance model on the log-transformed average daily food intake for a period with factors for sequence, period and treatment and unstructured variance-covariance matrix for the repeated measures across treatments for a subject. The LS means and confidence limits for differences in the logarithmic scale are exponentiated and reduced by one to give estimate and corresponding confidence limits of percent change in average daily food intake from placebo period to active treatment period. p-value is for testing percent change = 0.

No safety concerns were identified with repeated dosing of Davalintide (0.3 mcg/kg to 3 mcg/kg) BID for up to 12 days. Davalintide was generally well tolerated at all dosages tested. Among treatment-emergent adverse events, mild to moderate nausea had the highest incidence. The incidence of nausea and vomiting adverse events was the highest at 3 mcg/kg BID. The results of this study indicate that the occurrence of nausea and vomiting associated with Davalintide treatment was mitigated by dose escalation and generally subsided within ~2 days of treatment, suggesting that tolerance may develop with repeated dosing of Davalintide BID. The overall adverse event profile of Davalintide from this study is consistent with that observed in a previous single-dose study with Davalintide (Example 9) and with the adverse event profile of the amylinomimetic pramlintide, as well as with the pharmacological actions of Davalintide in nonclinical models, which include effects on gastric emptying and on cardiovascular parameters (transient decreases in blood pressure and sinus tachycardia), the latter likely due to vasodilatation and mediated by calcitonin gene-related peptide (CGRP) agonism. Nausea, vomiting, diarrhea, and injection site erythema are treatment-emergent adverse events frequently observed in previous studies in obese nondiabetic subjects treated with pramlintide by SC injection. The nausea, vomiting, loose stools, injection site adverse events, erythema, feeling hot, and flushing reported in this study were deemed to be not clinically significant and were not considered to have safety or dose-limiting implications. The erythema, feeling hot, and flushing adverse events were not accompanied by changes in blood pressure or other cardiovascular parameters, nor were they associated with changes in body temperature; these effects are likely to be due to peripheral vasodilatation, consistent with the receptor pharmacology of Davalintide.

Consistent with the PK profile observed in Example 9, Davalintide was rapidly absorbed (median Tmax of less than 1 h) and rapidly eliminated (median t1/2 of 0.5 h to 1.2 h). Following SC injection (0.3, 1, and 3 mcg/kg), Davalintide exposure (mean AUC(0-tlast), AUC(0-∞), and Cmax of plasma Davalintide concentrations) increased with increasing doses. Consistent with the short half-life of Davalintide, the results of this study indicate that there is no drug accumulation with repeated BID dosing of Davalintide at 0.3 mcg/kg to 3 mcg/kg for 4 days.

Davalintide treatment for 4 days at each of the dosages tested in this study (0.3, 1, and 3 mcg/kg) was associated with statistically and clinically significant reductions from the placebo treatment in mean daily ad libitum caloric intake. The acute effect of Davalintide to decrease caloric intake seen in this study is consistent with that observed in nonclinical models. The reduction (~36%) in mean daily caloric intake observed with the highest Davalintide dosage is greater in magnitude than that reported following 1 day of treatment with the amylinomimetic pramlintide at 180 mcg TID (~19%).

Despite the significant reductions in food intake, hunger and fullness levels during Davalintide treatment were similar to those reported during placebo treatment, suggesting that Davalintide may enhance the satiating effect of meals.

Example 11

A randomized, single-blind, placebo-controlled, multidose, four-period, crossover study was conducted to evaluate the safety, tolerability, and pharmacokinetics of Davalintide administered by SC injection to obese subjects. This study was conducted at a single clinical study site and consisted of two 8-day inpatient periods (Treatment Period 1 and Treatment Period 2) separated by a 7-day, outpatient washout period. Eligible subjects (based on screening) were admitted to the study site on Day −1. On Day 1, subjects were enrolled and randomized to one of two treatment sequences (Sequence A or Sequence B) in a 1:1 ratio. During the study, subjects in either sequence A or B received doses of 1, 2, 4, and 6 mcg/kg Davalintide and corresponding volumes of placebo QD in a dose-rising manner and in a crossover fashion, with each dose and placebo volume administered for 2 days, and with a 7-day washout period between Davalintide and placebo treatments during which subjects did not receive any study medication (see study design FIG. 18). The dose and volume per injection for Treatment Period 1 and Treatment Period 2 were calculated using the subject's body weight recorded at Visit 2 (Day −1) and Visit 3 (Day −1), respectively. Study medication (Davalintide or placebo) was administered by SC injection ~15 minutes prior to breakfast. PK, PD, and safety assessments were performed on select study days for up to 14 hours after dosing.

Figure 18:
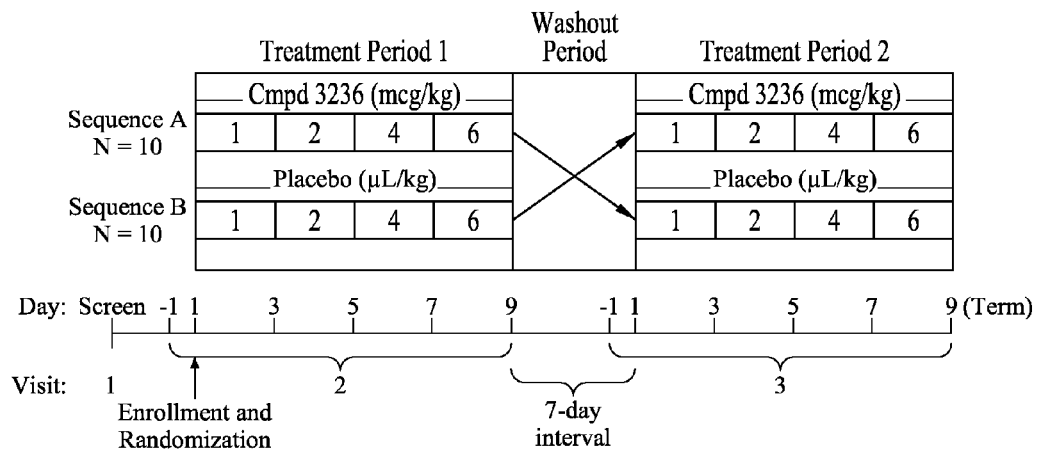
FIG. 18 depicts the cross-over design of the experiment described in Example 11.

The planned sample size was 20 individuals (10 subjects to be randomized to each of two treatment sequences, A and B), as shown in the Study Design figure (FIG. 18). A total of 20 subjects were randomized to treatment (10 subjects in each treatment sequence). All 20 subjects completed the study; there were no early withdrawals. Since all randomized subjects received an injection of study medication, the randomized and ITT populations are identical and include all 20 subjects. All 20 ITT subjects were considered evaluable.

Study subjects were males or nonpregnant, nonlactating females 19 to 55 years old, obese with a BMI≥30 kg/m$^2$ to ≤45 kg/m$^2$ at screening, and with no other major health problems as judged by the investigator. Females of childbearing potential were required to use appropriate contraceptive methods throughout the study.

Figure 19:
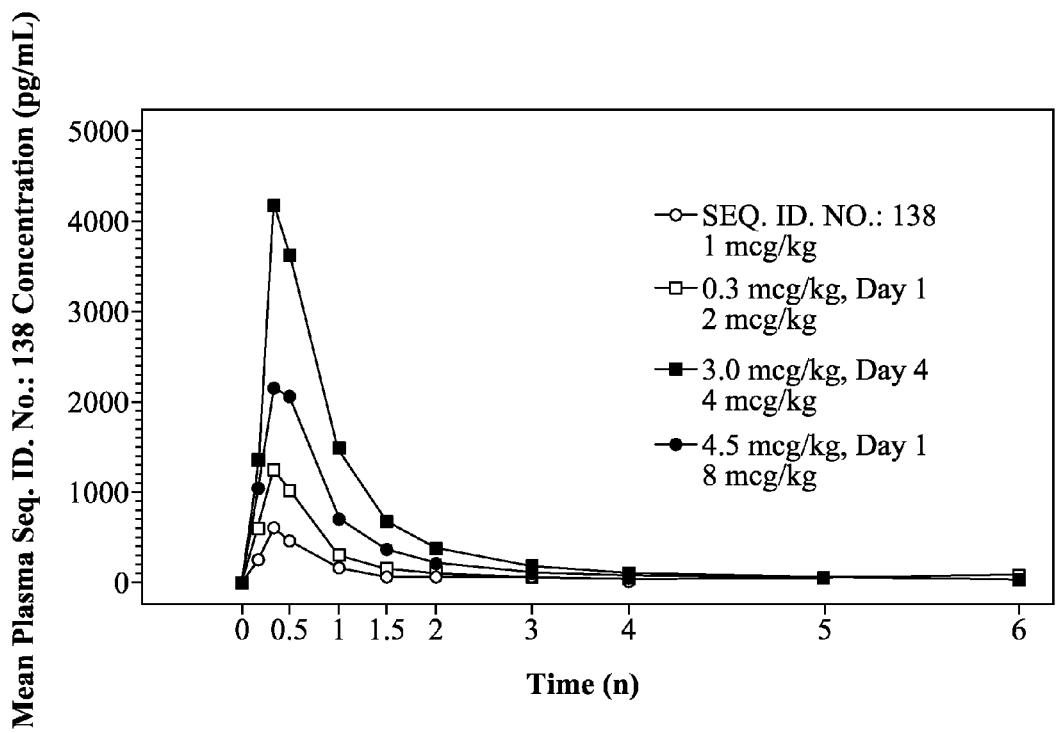
FIG. 19 depicts the plasma concentration as a function of time for the experiment described in Example 11.

Following SC injection of Davalintide (1, 2, 4, and 6 mcg/kg), the mean plasma Davalintide concentrations for all doses increased rapidly, peaking at ~0.33 h (20 min) after injection, and declined steadily thereafter through the 8-h blood sampling period. Mean plasma Davalintide concentrations increased with increasing doses. As shown in Table 9 and consistent with the PK profile (FIG. 19), mean $AUC_{(0-tlast)}$, $AUC_{(0-\infty)}$, and $C_{max}$ values increased with increasing doses.

TABLE 9

Plasma Davalintide Pharmacokinetic Parameters by Dose: Descriptive Statistics

| Parameter/ Statistics | 1 mcg/kg (N = 20) | 2 mcg/kg (N = 20) | 4 mcg/kg (N = 20) | 6 mcg/kg (N = 20) |
|---|---|---|---|---|
| AUC(0-tlast) (pg*h/mL) | | | | |
| n | 20 | 20 | 20 | 20 |
| Mean (SD) | 447.67 (294.13) | 982.16 (514.25) | 2114.34 (1346.70) | 3922.57 (1705.84) |
| SE | 65.77 | 114.99 | 301.13 | 381.44 |
| Geometric Mean (SE) [1] | 390.51 (43.07) | 896.11 (81.68) | 1873.61 (191.32) | 3665.42 (289.99) |
| CV % | 65.70 | 52.36 | 63.69 | 43.49 |
| Min, Max | 193.92, 1268.33 | 483.17, 2540.08 | 863.92, 6398.67 | 2235.83, 8409.17 |
| AUC(0-oo) (pg*h/mL) | | | | |
| n | 15 | 20 | 20 | 20 |
| Mean (SD) | 527.39 (335.40) | 1029.97 (531.15) | 2166.00 (1357.19) | 4008.93 (1731.44) |
| SE | 86.60 | 118.77 | 303.48 | 387.16 |
| Geometric Mean (SE) [1] | 459.86 (60.28) | 943.17 (83.92) | 1925.98 (193.96) | 3750.14 (294.18) |
| CV % | 63.60 | 51.57 | 62.66 | 43.19 |
| Min, Max | 223.74, 1336.56 | 523.67, 2609.03 | 902.06, 6477.66 | 2281.41, 8587.91 |
| Cave (pg/mL) | | | | |
| n | 20 | 20 | 20 | 20 |
| Mean (SD) | 226.38 (54.32) | 356.32 (120.10) | 522.30 (136.22) | 771.56 (216.12) |
| SE | 12.15 | 26.85 | 30.46 | 48.33 |
| Geometric Mean (SE) [1] | 220.24 (11.93) | 337.54 (25.65) | 507.63 (27.07) | 741.64 (48.72) |
| CV % | 23.99 | 33.71 | 26.08 | 28.01 |
| Min, Max | 138.08, 338.39 | 193.33, 635.02 | 367.19, 893.59 | 411.48, 1174.74 |
| Cmax (pg/mL) | | | | |
| n | 20 | 20 | 20 | 20 |
| Mean (SD) | 637.70 (274.43) | 1328.50 (493.74) | 2472.50 (787.59) | 4423.50 (993.33) |
| SE | 61.36 | 110.40 | 176.11 | 222.12 |
| Geometric Mean (SE) [1] | 592.22 (50.71) | 1262.62 (88.74) | 2367.47 (157.14) | 4322.40 (212.12) |
| CV % | 43.03 | 37.17 | 31.85 | 22.46 |
| Min, Max | 313.00, 1470.00 | 660.00, 3110.00 | 1420.00, 4670.00 | 2860.00, 6600.00 |
| Tmax (h) | | | | |
| n | 20 | 20 | 20 | 20 |
| Mean (SD) | 0.35 (0.08) | 0.37 (0.07) | 0.43 (0.17) | 0.38 (0.08) |
| SE | 0.02 | 0.02 | 0.04 | 0.02 |
| Geometric Mean (SE) [1] | 0.34 (0.02) | 0.37 (0.01) | 0.40 (0.03) | 0.38 (0.02) |
| CV % | 21.69 | 19.74 | 39.28 | 20.27 |
| Min, Max | 0.17, 0.52 | 0.33, 0.50 | 0.17, 1.00 | 0.33, 0.50 |
| T½ (h) | | | | |
| n | 15 | 20 | 20 | 20 |
| Mean (SD) | 0.49 (0.21) | 0.73 (0.28) | 0.83 (0.18) | 1.22 (0.39) |
| SE | 0.05 | 0.06 | 0.04 | 0.09 |
| Geometric Mean (SE) [1] | 0.46 (0.04) | 0.68 (0.06) | 0.81 (0.04) | 1.16 (0.08) |
| CV % | 42.01 | 38.84 | 22.20 | 32.46 |
| Min, Max | 0.25, 1.00 | 0.33, 1.41 | 0.46, 1.17 | 0.63, 2.03 |

[1] Geometric Mean (X) = exp[(logX1 + . . . + logXn)/n], Geometric SE(X) = Geometric Mean * SE (logX).

As shown in Table 10, inferential statistical analysis demonstrates that AUC(0-tlast), AUC(0-inf.) and Cmax increase with increasing dose of Davalintide administered BID.

TABLE 10

Plasma Davalintide Pharmacokinetic Parameters - Inferential Statistics - Parametric Statistics [1]

| Parameter/ Statistics | 1 mcg/kg (N = 20) | 2 mcg/kg (N = 20) | 4 mcg/kg (N = 20) | 6 mcg/kg (N = 20) |
|---|---|---|---|---|
| AUC(0-tlast) (pg*h/mL) | | | | |
| n | 20 | 20 | 20 | 20 |
| Geometric Mean (SE) [2] | 390.51 (43.071) | 896.11 (81.678) | 1873.61 (191.318) | 3665.42 (289.991) |
| %95 CI for Geometric Mean [3] | 310.01, 491.92 | 740.47, 1084.46 | 1513.08, 2320.05 | 3106.05, 4325.52 |
| Geometric LS Mean (SE) [4] [5] | 390.51 (43.394) | 896.11 (79.639) | 1873.61 (197.943) | 3665.42 (301.650) |
| %95 CI for Geometric LS Mean [3] [6] | 309.42, 492.87 | 743.04, 1080.71 | 1500.16, 2340.04 | 3081.31, 4360.25 |

TABLE 10-continued

Plasma Davalintide Pharmacokinetic Parameters - Inferential Statistics - Parametric Statistics [1]

| Parameter/<br>Statistics | 1 mcg/kg<br>(N = 20) | 2 mcg/kg<br>(N = 20) | 4 mcg/kg<br>(N = 20) | 6 mcg/kg<br>(N = 20) |
|---|---|---|---|---|
| AUC(0-oo) (pg*h/mL) | | | | |
| n | 15 | 20 | 20 | 20 |
| Geometric Mean (SE) [2] | 459.86 (60.279) | 943.17 (83.916) | 1925.98 (193.961) | 3750.14 (294.178) |
| %95 CI for Geometric Mean [3] | 347.16, 609.15 | 782.91, 1136.22 | 1559.94, 2377.90 | 3182.31, 4419.29 |
| Geometric LS Mean (SE) [4] [5] | 451.51 (47.363) | 943.17 (81.095) | 1925.98 (204.147) | 3750.14 (312.055) |
| %95 CI for Geometric LS Mean [3] [6] | 362.67, 562.12 | 787.35, 1129.81 | 1539.60, 2409.31 | 3142.61, 4475.11 |
| Cmax (pg/mL) | | | | |
| n | 20 | 20 | 20 | 20 |
| Geometric Mean (SE) [2] | 592.22 (50.706) | 1262.62 (88.738) | 2367.47 (157.136) | 4322.40 (212.117) |
| %95 CI for Geometric Mean [3] | 495.06, 708.45 | 1089.90, 1462.70 | 2060.40, 2720.30 | 3900.48, 4789.97 |
| Geometric LS Mean (SE) [4] [5] | 592.22 (49.020) | 1262.62 (85.912) | 2367.47 (154.651) | 4322.40 (214.791) |
| %95 CI for Geometric LS Mean [3] [6] | 497.84, 704.49 | 1094.71, 1456.29 | 2064.68, 2714.67 | 3894.10, 4797.82 |

[1] It is assumed that the distributions of AUC and Cmax are log-normal.
[2] Geometric Mean (GM) = exp(mean of log-transformed data). SE of GM is calculated as GM*SE(mean of the log-transformed data).
[3] Obtained by exponentiating the 95% confidence limits for the mean of log-transformed data.
[4] Based on a repeated measure ANOVA model on the log-transformed data with factors for dose and sequence, and an unstructured variance-covariance matrix for the repeated measures for a subject.
[5] Geometric LS mean is obtained by exponentiating the LS mean corresponding to the treatment. SE of Geometric LS mean is calculated as Geometric LS Mean × SE(of LS Mean).
[6] Obtained by exponentiating the confidence limits corresponding to the LS mean associated with the treatment.

Caloric intake was measured daily on Day 1 through Day 8 of each treatment period from ad libitum breakfast, lunch, dinner, and optional evening snack, served at specified times (~0.25 h, 4.25 h, 10.25 h, and 13.25 h±15 min, respectively) relative to study medication administration (time=0 h). Subjective ratings of hunger, fullness, thirst, and nausea were obtained on 100-mm Visual Analog Scales (VAS) repeatedly over ~14 hours, beginning 0.25 hours prior to study medication administration, on Day 1 through Day 8 of each treatment period. Plasma concentrations of Davalintide were measured from blood samples collected on the first day of each treatment period (Days 1, 3, 5, and 7) prior to and over ~8 hours after study medication administration.

Data across sequences were pooled as appropriate for data summarization and analyses. Data were summarized descriptively by treatment and, as appropriate, by sequence. All hypotheses were tested against two-sided alternatives, and the results were interpreted at a significance level of 0.05. Unless otherwise indicated, the baseline value of a characteristic was defined as the last value prior to the first injection of any dose of study medication (Davalintide or placebo). Since the ITT and Evaluable Populations in this study are identical, all analyses are presented for the ITT population.

The study was powered to determine changes in daily caloric intake. The daily and by-meal (breakfast, lunch, dinner, or evening snack) caloric intake was summarized by treatment (each Davalintide dose and placebo volume). The absolute placebo-corrected daily and by-meal caloric intake were calculated by subtracting the daily caloric intake associated with a placebo volume from those associated with the corresponding Davalintide dose. The average daily caloric intake across Day 1 and Day 2 was calculated for each subject and then summarized by treatment. Similar summaries were produced for absolute and percent placebo-corrected average daily caloric intake associated with each Davalintide dose. Average daily caloric intake data were analyzed using a repeated measures analysis of variance (ANOVA) model with factors for sequence, period, and treatment; and an unstructured variance-covariance matrix for the repeated measures from the same subject. Similarly, daily caloric intake and average caloric intake at each meal on each day (Day 1 and Day 2) were analyzed to examine the duration of the effect of a QD injection.

Statistically significant reductions in mean absolute placebo-corrected average daily caloric intake were observed with Davalintide treatment at dosages from 2 mcg/kg BID. As shown in Table 11, the LS mean reductions from placebo amounted to 352.6 kcal (p=0.0286), −344.7 kcal (p=0.0799), and −593.4 kcal (p=0.0071) for 2, 4, and 6 mcg/kg QD, respectively. For all Davalintide treatments, the cumulative reductions in daily caloric intake were primarily attributable to reductions in caloric intake at breakfast.

TABLE 11

Absolute Placebo-Corrected Average Caloric Intake Pharmacodynamic Parameters by Treatment: Parametric Statistics [3]

| Meal/<br>Treatment/<br>Statistics | 1 mcg/kg<br>(N = 20) | 2 mcg/kg<br>(N = 20) | 4 mcg/kg<br>(N = 20) | 6 mcg/kg<br>(N = 20) |
|---|---|---|---|---|
| Daily Total | | | | |
| Matching Placebo [1] | | | | |
| N | 20 | 20 | 20 | 20 |
| Mean (SE) | 3174.5 (211.70) | 3305.5 (222.34) | 3015.9 (222.20) | 3249.3 (195.25) |
| Placebo-Corrected | | | | |
| N | 20 | 20 | 20 | 20 |
| Mean (SE) [2] | 61.0 (151.97) | −352.6 (150.39) | −344.7 (174.32) | −593.5 (180.61) |

TABLE 11-continued

Absolute Placebo-Corrected Average Caloric Intake Pharmacodynamic
Parameters by Treatment: Parametric Statistics [3]

| Meal/<br>Treatment/<br>Statistics | 1 mcg/kg<br>(N = 20) | 2 mcg/kg<br>(N = 20) | 4 mcg/kg<br>(N = 20) | 6 mcg/kg<br>(N = 20) |
|---|---|---|---|---|
| LS Mean (SE) | 60.9 (137.28) | −352.6 (148.86) | −344.7 (184.82) | −593.4 (192.78) |
| 95% CI of LS Mean | −234.16, 356.06 | −664.20, −40.95 | −735.14, 45.79 | −1001.4, −185.46 |
| p-value | 0.6640 | 0.0286 | 0.0799 | 0.0071 |

[1] Caloric intake over the two days of the corresponding placebo volume were averaged for each subject prior to summarization or model fitting.
[2] Caloric intake on each day were subtracted by the caloric intake on the corresponding placebo day for each subject first, then averaged over the two days of each dose, prior to summarization.
[3] Based on a repeated measure ANOVA model on the average caloric intake at each dose and volume with factors for sequence, period, and treatment, and unstructured matrix for the repeated measures for a subject.

Noncompartmental PK parameters of plasma Davalintide concentrations were calculated and summarized for each Davalintide dose by relative day within each period. Point estimates of mean log(AUC) and mean log(Cmax) and their 95% confidence intervals (CIs) were constructed by dose, assuming that the logarithms of AUC and $C_{max}$ are normally distributed. These point estimates and confidence limits were exponentiated back to the original scale. The exponentiated point estimate are referred to as the geometric mean (GM); its standard error (SE) was calculated based on the delta method as GM×SE of the mean of the log-transformed data. In addition, log(AUC) and mean log($C_{max}$) were analyzed using a repeated-measure ANOVA model with a factor for dose (4 levels) and sequence (A or B), and an unstructured variance-covariance matrix for the repeated measures from the same subject. The LS means, SEs of the LS means, and 95% CIs of the LS means were derived from the fitted model for the log-transformed data for each Davalintide dose. The antilogs of the LS means, SEs, and confidence limits were then exponentiated back to the original scale to provide the geometric LS means, SEs of the geometric LS means, and the geometric 95% CIs Noncompartmental PD parameters for hunger, fullness, thirst, and nausea were calculated for each subject. For each of these assessments, the mean areas under the VAS rating curve over the 14-h observation period (AUC(−0.25-14.25 h)) associated with each Davalintide treatment was compared to that of the within-sequence placebo treatment using similar methods as for caloric intake.

Mean hunger and fullness rating profiles over a 14-h observation period were similar for each Davalintide treatment (1, 2, 4, and 6 mcg/kg) and corresponding placebo treatments. Consistent with the mean hunger and fullness rating profiles, there were no statistically significant differences in either mean placebo-corrected $AUC_{(-0.25-14.25\,h)}$ or mean maximum VAS rating for hunger or fullness for any of the Davalintide treatments, despite the significant reductions in mean daily caloric intake observed with the 2, 4, and 6 mcg/kg BID dosages. Similar results were observed for mean thirst rating profiles and pharmacodynamic parameters.

Change in weight, absolute and percent, after administration of Davalintide as a function of dosage during the trial described in Example 11 is provided in Table 12.

TABLE 12

Change and percent change in weight for Davalintide
and placebo according to protocol of Example 11.

| | Davalintide | | | |
|---|---|---|---|---|
| Statistics | 1 mcg/kg | 2 mcg/kg | 4 mcg/kg | 6 mcg/kg |
| Change in Weight (kg) from Baseline [1] [2] | | | | |
| n | 20 | 20 | 20 | 20 |
| Mean (SD) | −0.13 (0.862) | −0.48 (0.862) | −0.85 (1.148) | −0.79 (1.308) |
| SE | 0.193 | 0.193 | 0.257 | 0.292 |
| Median | 0.00 | −0.35 | −0.75 | −0.85 |
| Min, Max | −1.6, 1.9 | −2.0, 1.3 | −2.9, 0.6 | −3.5, 1.9 |
| Percent Change in Weight from Baseline [1] [3] | | | | |
| n | 20 | 20 | 20 | 20 |
| Mean (SD) | −0.19 (0.850) | −0.51 (0.892) | −0.87 (1.169) | −0.74 (1.341) |
| SE | 0.190 | 0.199 | 0.261 | 0.300 |
| Median | 0.00 | −0.34 | −0.73 | −0.95 |
| Min, Max | −1.6, 1.5 | −2.2, 1.0 | −3.2, 0.5 | −3.1, 2.4 |
| | Placebo | | | |
| Statistics | 1 μL/kg | 2 μL/kg | 4 μL/kg | 6 μL/kg |
| Change in Weight (kg) from Baseline [1] [2] | | | | |
| n | 20 | 20 | 20 | 20 |
| Mean (SD) | −0.24 (1.292) | 0.03 (1.198) | 0.06 (1.317) | 0.56 (1.531) |
| SE | 0.289 | 0.268 | 0.294 | 0.342 |
| Median | −0.10 | 0.05 | 0.30 | 0.30 |

TABLE 12-continued

Change and percent change in weight for Davalintide
and placebo according to protocol of Example 11.

| Min, Max | −3.3, 1.7 | −3.3, 1.6 | −3.9, 1.7 | −2.9, 3.6 |
|---|---|---|---|---|
| Percent Change in Weight from Baseline [1] [3] | | | | |
| n | 20 | 20 | 20 | 20 |
| Mean (SD) | −0.28 (1.289) | −0.05 (1.276) | −0.01 (1.442) | 0.46 (1.590) |
| SE | 0.288 | 0.285 | 0.322 | 0.355 |
| Median | −0.14 | 0.04 | 0.29 | 0.28 |
| Min, Max | −3.2, 1.8 | −4.0, 1.7 | −4.7, 1.7 | −3.5, 3.8 |

[1] Baseline body weight is body weight recorded at Day 1 of the period.
[2] Absolute change from baseline is calculated as the change in body weight (kg) from Baseline of each treatment period to the next measurement after the last dose of interest.
[3] Percent change (%) is calculated by dividing the absolute change in body weight by the baseline body weight multiplied by 100.

No safety concerns were identified with repeated dosing of Davalintide (1 mcg/kg to 6 mcg/kg) for up to 8 days. Davalintide was generally well tolerated at all dosages tested. Among treatment-emergent adverse events, mild to moderate nausea and mild injection site adverse events had the highest incidence. The results of this study indicate that the occurrence of nausea and vomiting associated with Davalintide treatment was mitigated by dose escalation and generally subsided over time. No deaths occurred during this study. No serious adverse events were reported during this study. No subjects were withdrawn due to a treatment-emergent adverse event in this study.

Example 12

The Continual Reassessment Method (CRM) is a one-parameter, dose-finding model utilized in Phase 1 studies, particularly oncology trials. Here the CRM was used to guide dose escalation in the first human trial of Davalintide, a new molecular entity with amylin mimetic properties.

Obese subjects were enrolled in consecutive cohorts, each comprising four individuals, at a single clinical study site. Study medication (davalintide or placebo) was investigated according to a progressive dose escalation scheme, with planned davalintide doses of 0.03, 0.1, 0.3, 1, 3, and 10 mcg/kg, administered subcutaneously, twice per day, pre-meal. After the initial cohort, the protocol allowed for each subsequent cohort to be studied at (1) the same dose as the previous cohort, (2) the next planned higher or lower dowse, or (3) a dose intermediate to the planned doses, to enable a better understanding of potential adverse events. Decisions concerning the dosing of each subsequent cohort were made by the investigator based on clinical assessment of safety and tolerability data from the previous cohort(s) and guided by the CRM. The CRM was used to identify a target dose with a pre-defined safety/tolerability rate of ~20%.

Figure 20:
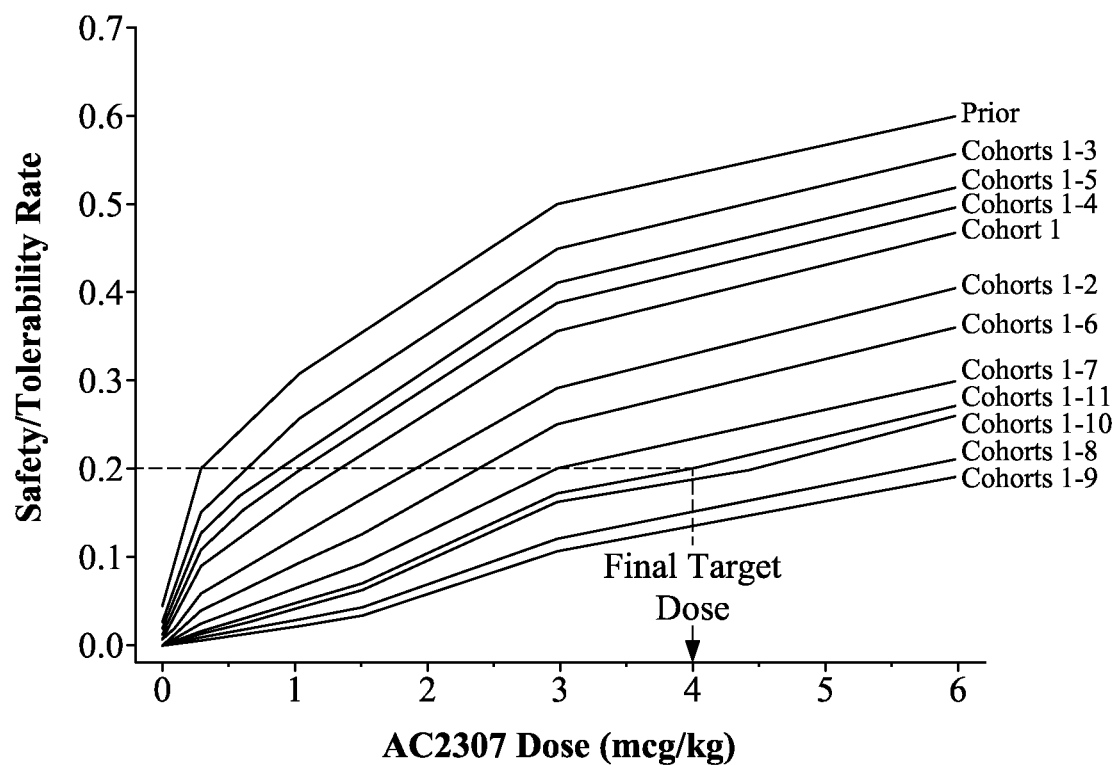
FIG. 20 depicts the Safety or Tolerability Rate for the trial discussed in Example 12.

A total of 44 subjects were studied in 11 consecutive dosing cohorts. As a result of the clinical and CRM evaluation, doses of 0.03, 0.1, 0.3, 0.6, 1.5, 1.5, 3, 6, 3, 4.5 and 4.5 mcg/kg were examined in cohorts 1 through 11, respectively. At the conclusion of the study, the final target dose defined by the CRM was ~4 ug/kg for single dose administration of davalintide (FIG. 20), which was consistent with clinical judgment.

While the foregoing description discloses the present invention, with examples provided for the purpose of illustration, it will be understood that the practice of the present invention encompasses all of the usual variations, adaptations, or modifications as being within the scope of the claimed invention.

---

We claim:

1. A method for reducing body fat or body fat gain in a subject in need of treatment while maintaining or increasing lean body mass; of altering a body composition of a subject in need of treatment, wherein body fat is reduced and lean body mass is maintained or increased; for reducing body weight in a subject in need of, or desirous of, weight reduction; or for reducing caloric intake in a subject in need of reduction thereof, the method comprising administering an effective amount to the subject an amylin agonist, wherein the amylin agonist comprises the sequence set forth in SEQ ID NO:138, thereby reducing body fat or body fat gain while maintaining or increasing lean body mass; altering a body composition while reducing body fat and maintaining or increasing lean body mass; reducing body weight; or reducing caloric intake, wherein the amylin agonist is administered in a manner sufficient to maintain an average plasma concentration of the amylin agonist of at least about 50 pg/mL for a period of time selected from the group consisting of at least about 1 hr, at least about 2 hrs, at least about 3 hrs, at least about 4 hrs, at least about 5 hrs, at least about 6 hrs, at least about 7 hrs, at least about 8 hrs, at least about 12 hrs, at least about 1 day, at least about 2 days, at least about 3 days, at least about 1 week, at least about 2 weeks, and at least about 1 month.

2. The method of claim 1, wherein the amylin agonist is administered parenterally.

3. The method of claim 1, wherein the amylin agonist is davalintide.

* * * * *

SEQUENCE LISTING

```
<160> NUMBER OF SEQ ID NOS: 145

<210> SEQ ID NO 1
<211> LENGTH: 37
<212> TYPE: PRT
<213> ORGANISM: Homo sapiens

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 2
<211> LENGTH: 37
<212> TYPE: PRT
<213> ORGANISM: Rattus sp.

<400> SEQUENCE: 2
```

```
Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
                20                  25                  30

Gly Ser Asn Thr Tyr
            35

<210> SEQ ID NO 3
<211> LENGTH: 32
<212> TYPE: PRT
<213> ORGANISM: Unknown
<220> FEATURE:
<223> OTHER INFORMATION: Description of Unknown: Salmon calcitonin
      peptide

<400> SEQUENCE: 3

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
                20                  25                  30

<210> SEQ ID NO 4
<211> LENGTH: 32
<212> TYPE: PRT
<213> ORGANISM: Homo sapiens

<400> SEQUENCE: 4

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
                20                  25                  30

<210> SEQ ID NO 5
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: hydrogen Lys, Ser, Ala, des-alpha-amino Lys, or
      acetylated Lys
<220> FEATURE:
<221> NAME/KEY: MOD_RES
<222> LOCATION: (2)..(2)
<223> OTHER INFORMATION: Independently selected residue having a side
      chain chemically bonded to the residue at position 7 to form an
      intramolecular linkage
<220> FEATURE:
<221> NAME/KEY: MOD_RES
<222> LOCATION: (7)..(7)
<223> OTHER INFORMATION: Independently selected residue having a side
      chain chemically bonded to the residue at position 2 to form an
      intramolecular linkage
<220> FEATURE:
<221> NAME/KEY: MOD_RES
<222> LOCATION: (13)..(13)
<223> OTHER INFORMATION: Ala, Ser or Thr
<220> FEATURE:
<221> NAME/KEY: MOD_RES
<222> LOCATION: (17)..(17)
<223> OTHER INFORMATION: Val, Leu or Ile
<220> FEATURE:
<221> NAME/KEY: MOD_RES
<222> LOCATION: (18)..(18)
<223> OTHER INFORMATION: His or Arg
<220> FEATURE:
<221> NAME/KEY: MOD_RES
```

```
<222> LOCATION: (19)..(19)
<223> OTHER INFORMATION: Ser or Thr
<220> FEATURE:
<221> NAME/KEY: MOD_RES
<222> LOCATION: (20)..(20)
<223> OTHER INFORMATION: Ser, Thr, Gln or Asn
<220> FEATURE:
<221> NAME/KEY: MOD_RES
<222> LOCATION: (21)..(21)
<223> OTHER INFORMATION: Asn, Gln or His
<220> FEATURE:
<221> NAME/KEY: MOD_RES
<222> LOCATION: (23)..(23)
<223> OTHER INFORMATION: Phe, Leu or Tyr
<220> FEATURE:
<221> NAME/KEY: MOD_RES
<222> LOCATION: (25)..(25)
<223> OTHER INFORMATION: Ala or Pro
<220> FEATURE:
<221> NAME/KEY: MOD_RES
<222> LOCATION: (26)..(26)
<223> OTHER INFORMATION: Ile, Val, Ala or Leu
<220> FEATURE:
<221> NAME/KEY: MOD_RES
<222> LOCATION: (28)..(28)
<223> OTHER INFORMATION: Ser, Pro, Leu, Ile or Thr
<220> FEATURE:
<221> NAME/KEY: MOD_RES
<222> LOCATION: (29)..(29)
<223> OTHER INFORMATION: Ser, Pro or Thr
<220> FEATURE:
<221> NAME/KEY: MOD_RES
<222> LOCATION: (31)..(31)
<223> OTHER INFORMATION: Asn, Asp or Gln
<220> FEATURE:
<221> NAME/KEY: MOD_RES
<222> LOCATION: (38)..(38)
<223> OTHER INFORMATION: hydroxy, amino, alkylamino, dialkylamino,
      cycloalkylamino, arylamino, aralkylamino, alkyloxy, aryloxy or
      aralkyloxy or not present
<220> FEATURE:
<223> OTHER INFORMATION: see specification as filed for detailed
      description of substitutions and preferred embodiments

<400> SEQUENCE: 5

Xaa Xaa Asn Thr Ala Thr Xaa Ala Thr Gln Arg Leu Xaa Asn Phe Leu
1               5                   10                  15

Xaa Xaa Xaa Xaa Xaa Asn Xaa Gly Xaa Xaa Leu Xaa Xaa Thr Xaa Val
            20                  25                  30

Gly Ser Asn Thr Tyr Xaa
        35

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Independently selected residue having a side
      chain chemically bonded to the residue at position 8 to form an
      intramolecular linkage
<220> FEATURE:
<221> NAME/KEY: MOD_RES
<222> LOCATION: (2)..(2)
<223> OTHER INFORMATION: Any amino acid or absent
<220> FEATURE:
<221> NAME/KEY: MOD_RES
<222> LOCATION: (3)..(3)
<223> OTHER INFORMATION: Ala, Gly, Ser, Asp or absent
<220> FEATURE:
<221> NAME/KEY: MOD_RES
<222> LOCATION: (4)..(4)
```

```
<223> OTHER INFORMATION: Asn, Ala, Asp, Gly or absent
<220> FEATURE:
<221> NAME/KEY: MOD_RES
<222> LOCATION: (5)..(5)
<223> OTHER INFORMATION: Ala, Leu, Thr, or Ser
<220> FEATURE:
<221> NAME/KEY: MOD_RES
<222> LOCATION: (6)..(6)
<223> OTHER INFORMATION: Ala, Ser, or Thr
<220> FEATURE:
<221> NAME/KEY: MOD_RES
<222> LOCATION: (7)..(7)
<223> OTHER INFORMATION: Ala, Ser, Val, Hse, (S)-2-amino-3-hydroxy-
      methylbutanoic acid (Ahb), (2S,3R)-2-amino-3-hydroxy-
      methylpentanoic acid (Ahp), D-Thr, Thr, or a derivative thereof
<220> FEATURE:
<221> NAME/KEY: MOD_RES
<222> LOCATION: (8)..(8)
<223> OTHER INFORMATION: Independently selected residue having a side
      chain chemically bonded to the residue at position 1 to form an
      intramolecular linkage
<220> FEATURE:
<223> OTHER INFORMATION: see specification as filed for detailed
      description of substitutions and preferred embodiments

<400> SEQUENCE: 6

Xaa Xaa Xaa Xaa Xaa Xaa Xaa Xaa
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any amino acid or absent
<220> FEATURE:
<223> OTHER INFORMATION: see specification as filed for detailed
      description of substitutions and preferred embodiments

<400> SEQUENCE: 7

Xaa Xaa Xaa Xaa Xaa Xaa
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Asn Thr Ala Thr Cys
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Ala Thr Ala Thr Cys
1               5
```

```
<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Asp Thr Ala Thr Cys
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Gly Thr Ala Thr Cys
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Asn Ala Ala Thr Cys
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Asn Thr Ser Thr Cys
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: D-Thr

<400> SEQUENCE: 14

Cys Asn Thr Ala Xaa Cys
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<221> NAME/KEY: MOD_RES
<222> LOCATION: (5)..(5)
<223> OTHER INFORMATION: T(OPO3H2)

<400> SEQUENCE: 15

Cys Asn Thr Ala Xaa Cys
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Asn Thr Ala Ser Cys
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Asn Thr Ala Ala Cys
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Asn Thr Ala Val Cys
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hse

<400> SEQUENCE: 19

Cys Asn Thr Ala Xaa Cys
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (5)..(5)
<223> OTHER INFORMATION: Ahb

<400> SEQUENCE: 20

Cys Asn Thr Ala Xaa Cys
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ahp

<400> SEQUENCE: 21

Cys Asn Thr Ala Xaa Cys
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Ser Asn Leu Ser Thr Cys
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Gly Asn Leu Ser Thr Cys
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Ala Asn Leu Ser Thr Cys
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25
```

```
Cys Ser Ala Leu Ser Thr Cys
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Ser Asn Ala Ser Thr Cys
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Cys Ser Asn Leu Ala Thr Cys
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Ser Asn Leu Ser Ala Cys
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Cys Asn Thr Ala Thr Cys
1               5

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Leu Gln Gln Leu Gln Lys Leu Leu Gln Lys Leu Lys Gln Tyr
1               5                   10                  15

<210> SEQ ID NO 31
<211> LENGTH: 28
<212> TYPE: PRT
<213> ORGANISM: Artificial Sequence
<220> FEATURE:
<223> OTHER INFORMATION: Description of Artificial Sequence: Synthetic
```

-continued

```
                peptide
<220> FEATURE:
<221> NAME/KEY: MOD_RES
<222> LOCATION: (1)..(4)
<223> OTHER INFORMATION: Any amino acid or absent and this region may
      encompass 1 to 4 residues
<220> FEATURE:
<221> NAME/KEY: MOD_RES
<222> LOCATION: (7)..(7)
<223> OTHER INFORMATION: Gly or Aib
<220> FEATURE:
<221> NAME/KEY: MOD_RES
<222> LOCATION: (8)..(8)
<223> OTHER INFORMATION: Lys, Arg, Orn, hArg, Cit, hLys, or Lys(for)
<220> FEATURE:
<221> NAME/KEY: MOD_RES
<222> LOCATION: (12)..(12)
<223> OTHER INFORMATION: Glu or Phe
<220> FEATURE:
<221> NAME/KEY: MOD_RES
<222> LOCATION: (14)..(14)
<223> OTHER INFORMATION: His or Aib
<220> FEATURE:
<221> NAME/KEY: MOD_RES
<222> LOCATION: (15)..(15)
<223> OTHER INFORMATION: Lys, Arg, Orn, hArg, Cit, hLys, Lys(for),
      Lys(PEG 5000)
<220> FEATURE:
<221> NAME/KEY: MOD_RES
<222> LOCATION: (19)..(19)
<223> OTHER INFORMATION: Tyr or Leu
<220> FEATURE:
<221> NAME/KEY: MOD_RES
<222> LOCATION: (21)..(21)
<223> OTHER INFORMATION: Arg or Pro
<220> FEATURE:
<221> NAME/KEY: MOD_RES
<222> LOCATION: (25)..(28)
<223> OTHER INFORMATION: Any amino acid or absent and this region may
      encompass 1 to 4 residues
<220> FEATURE:
<223> OTHER INFORMATION: see specification as filed for detailed
      description of substitutions and preferred embodiments

<400> SEQUENCE: 31

Xaa Xaa Xaa Xaa Val Leu Xaa Xaa Leu Ser Gln Xaa Leu Xaa Xaa Leu
1               5                   10                  15

Gln Thr Xaa Pro Xaa Thr Asn Thr Xaa Xaa Xaa Xaa
            20                  25

<210> SEQ ID NO 32
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any amino acid or absent and this region may
      encompass 1 to 4 residues
<220> FEATURE:
<221> NAME/KEY: MOD_RES
<222> LOCATION: (5)..(5)
<223> OTHER INFORMATION: Ala or Val
<220> FEATURE:
<221> NAME/KEY: MOD_RES
<222> LOCATION: (6)..(6)
<223> OTHER INFORMATION: Thr, Met or Leu
<220> FEATURE:
<221> NAME/KEY: MOD_RES
<222> LOCATION: (7)..(7)
<223> OTHER INFORMATION: Gln, Gly or His
<220> FEATURE:
<221> NAME/KEY: MOD_RES
<222> LOCATION: (9)..(9)
```

```
<223> OTHER INFORMATION: Leu or Thr
<220> FEATURE:
<221> NAME/KEY: MOD_RES
<222> LOCATION: (10)..(10)
<223> OTHER INFORMATION: Ala, Thr, Asn, Phe, Tyr, Ser, or Thr
<220> FEATURE:
<221> NAME/KEY: MOD_RES
<222> LOCATION: (11)..(11)
<223> OTHER INFORMATION: Asn, Arg, Ala, Asp, Glu, Gln, Thr, or Gly
<220> FEATURE:
<221> NAME/KEY: MOD_RES
<222> LOCATION: (12)..(12)
<223> OTHER INFORMATION: Phe, Leu, Ser, Glu, Ala, Asp, or Tyr
<220> FEATURE:
<221> NAME/KEY: MOD_RES
<222> LOCATION: (13)..(13)
<223> OTHER INFORMATION: Leu or Asp
<220> FEATURE:
<221> NAME/KEY: MOD_RES
<222> LOCATION: (14)..(14)
<223> OTHER INFORMATION: Val, His, Ser, Phe, or Aib
<220> FEATURE:
<221> NAME/KEY: MOD_RES
<222> LOCATION: (15)..(15)
<223> OTHER INFORMATION: His, Arg, Lys, Orn, hArg, Cit, hLys, Lys(for),
      or Lys(PEG5000)
<220> FEATURE:
<221> NAME/KEY: MOD_RES
<222> LOCATION: (16)..(16)
<223> OTHER INFORMATION: Leu, Ser or Phe
<220> FEATURE:
<221> NAME/KEY: MOD_RES
<222> LOCATION: (17)..(17)
<223> OTHER INFORMATION: Gln or His
<220> FEATURE:
<221> NAME/KEY: MOD_RES
<222> LOCATION: (18)..(18)
<223> OTHER INFORMATION: Thr or Asn
<220> FEATURE:
<221> NAME/KEY: MOD_RES
<222> LOCATION: (19)..(19)
<223> OTHER INFORMATION: Tyr, Val, Phe, Leu or Met
<220> FEATURE:
<221> NAME/KEY: MOD_RES
<222> LOCATION: (21)..(21)
<223> OTHER INFORMATION: Arg or Pro
<220> FEATURE:
<221> NAME/KEY: MOD_RES
<222> LOCATION: (25)..(28)
<223> OTHER INFORMATION: Any amino acid or absent and this region may
      encompass 1 to 4 residues
<220> FEATURE:
<223> OTHER INFORMATION: see specification as filed for detailed
      description of substitutions and preferred embodiments

<400> SEQUENCE: 32

Xaa Xaa Xaa Xaa Xaa Xaa Xaa Arg Xaa Xaa Xaa Xaa Xaa Xaa Xaa
1               5                   10                  15

Xaa Xaa Xaa Pro Xaa Thr Asn Thr Xaa Xaa Xaa Xaa
            20                  25

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Tyr, or absent
<220> FEATURE:
<221> NAME/KEY: MOD_RES
<222> LOCATION: (2)..(2)
<223> OTHER INFORMATION: Ser, Pro, or absent
<220> FEATURE:
```

```
<221> NAME/KEY: MOD_RES
<222> LOCATION: (3)..(3)
<223> OTHER INFORMATION: Ser, Pro, Arg, or absent
<220> FEATURE:
<221> NAME/KEY: MOD_RES
<222> LOCATION: (4)..(4)
<223> OTHER INFORMATION: Thr or absent
<220> FEATURE:
<221> NAME/KEY: MOD_RES
<222> LOCATION: (5)..(5)
<223> OTHER INFORMATION: Asn or absent
<220> FEATURE:
<221> NAME/KEY: MOD_RES
<222> LOCATION: (6)..(6)
<223> OTHER INFORMATION: Val, Thr, or absent
<220> FEATURE:
<221> NAME/KEY: MOD_RES
<222> LOCATION: (8)..(8)
<223> OTHER INFORMATION: Ser or Glu
<220> FEATURE:
<221> NAME/KEY: MOD_RES
<222> LOCATION: (9)..(9)
<223> OTHER INFORMATION: Asn, Lys, or Gly
<220> FEATURE:
<221> NAME/KEY: MOD_RES
<222> LOCATION: (10)..(10)
<223> OTHER INFORMATION: Thr, Phe, or Ala
<220> FEATURE:
<221> NAME/KEY: MOD_RES
<222> LOCATION: (11)..(11)
<223> OTHER INFORMATION: Tyr, Phe, Pro, or absent
<220> FEATURE:
<223> OTHER INFORMATION: when the loop region is from a calcitonin or
      calcitonin analog and the alpha-helix region is from a calcitonin
      or calcitonin analog, the last position of the C-terminal tail is
      not Pro, Hyp, homoSerine (Hse) or derivatives of Hse
<220> FEATURE:
<223> OTHER INFORMATION: see specification as filed for detailed
      description of substitutions and preferred embodiments

<400> SEQUENCE: 33

Xaa Xaa Xaa Xaa Xaa Xaa Gly Xaa Xaa Xaa Xaa
1               5                   10

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Ser Asn Phe Val Pro Thr Asn
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Asn Phe Val Pro Thr Asn Val
1               5

<210> SEQ ID NO 36
<211> LENGTH: 32
<212> TYPE: PRT
<213> ORGANISM: Artificial Sequence
<220> FEATURE:
<223> OTHER INFORMATION: Description of Artificial Sequence: Synthetic
```

-continued

```
      polypeptide
<220> FEATURE:
<221> NAME/KEY: MOD_RES
<222> LOCATION: (1)..(1)
<223> OTHER INFORMATION: Ala, Cys, homoCys, Asp, Glu, Phe, Ile, Leu,
      Lys, homoLys, Arg, homoArg, Ser, Hse(homoSER), Thr, Gly, Gln, Asn,
      Met, Tyr, Trp, Pro, Hyp(hydroxyProline), His, Val or absent
<220> FEATURE:
<221> NAME/KEY: MOD_RES
<222> LOCATION: (2)..(2)
<223> OTHER INFORMATION: Independently selected residue having a side
      chain chemically bonded to the residue at position 7 to form an
      intramolecular linkage
<220> FEATURE:
<221> NAME/KEY: MOD_RES
<222> LOCATION: (3)..(3)
<223> OTHER INFORMATION: Ala, Asp, Glu, Asn, Gln, Gly, Val, Arg, Lys,
      homoLys, homoArg, His, Ile, Leu, Met, or absent
<220> FEATURE:
<221> NAME/KEY: MOD_RES
<222> LOCATION: (4)..(4)
<223> OTHER INFORMATION: Ala, Ile, Leu, Ser, Hse, Thr, Val, Met, or
      absent
<220> FEATURE:
<221> NAME/KEY: MOD_RES
<222> LOCATION: (5)..(5)
<223> OTHER INFORMATION: Ala, Ser, Thr, Hse, Tyr, Val, Ile, Leu, or Met
<220> FEATURE:
<221> NAME/KEY: MOD_RES
<222> LOCATION: (6)..(6)
<223> OTHER INFORMATION: Thr, Ala, Ser, Hse, Tyr, Val, Ile, Leu, or Met
<220> FEATURE:
<221> NAME/KEY: MOD_RES
<222> LOCATION: (7)..(7)
<223> OTHER INFORMATION: Independently selected residue having a side
      chain chemically bonded to the residue at position 2 to form an
      intramolecular linkage
<220> FEATURE:
<221> NAME/KEY: MOD_RES
<222> LOCATION: (8)..(8)
<223> OTHER INFORMATION: Ala, Val, Ile, Leu, Phe, or Met
<220> FEATURE:
<221> NAME/KEY: MOD_RES
<222> LOCATION: (9)..(9)
<223> OTHER INFORMATION: Leu, Thr, Ser, Hse, Val, Ile, or Met
<220> FEATURE:
<221> NAME/KEY: MOD_RES
<222> LOCATION: (10)..(10)
<223> OTHER INFORMATION: Gly, His, Gln, Lys, Arg, Asn, homoLys, or
      homoArg
<220> FEATURE:
<221> NAME/KEY: MOD_RES
<222> LOCATION: (11)..(11)
<223> OTHER INFORMATION: Lys, Arg, Gln, Asn, homoLys, homoArg, or His
<220> FEATURE:
<221> NAME/KEY: MOD_RES
<222> LOCATION: (12)..(12)
<223> OTHER INFORMATION: Leu, Ile, Val, Phe, Met, Trp, or Tyr
<220> FEATURE:
<221> NAME/KEY: MOD_RES
<222> LOCATION: (13)..(13)
<223> OTHER INFORMATION: Ala, Phe, Tyr, Asn, Gln, Ser, Hse, or Thr
<220> FEATURE:
<221> NAME/KEY: MOD_RES
<222> LOCATION: (14)..(14)
<223> OTHER INFORMATION: Ala, Asp, Glu, Gly, Asn, Lys, Gln, Arg, His,
      homoArg, or homoLys
<220> FEATURE:
<221> NAME/KEY: MOD_RES
<222> LOCATION: (15)..(15)
<223> OTHER INFORMATION: Ala, Asp, Glu, Phe, Leu, Ser, Tyr, Ile, Val, or
      Met
<220> FEATURE:
<221> NAME/KEY: MOD_RES
<222> LOCATION: (16)..(16)
<223> OTHER INFORMATION: Leu, Phe, Met, Val, Tyr, or Ile
<220> FEATURE:
<221> NAME/KEY: MOD_RES
<222> LOCATION: (17)..(17)
<223> OTHER INFORMATION: His, Gln, Asn, Ser, Hse, Thr, or Val
```

```
<220> FEATURE:
<221> NAME/KEY: MOD_RES
<222> LOCATION: (18)..(18)
<223> OTHER INFORMATION: Lys, homoLys, Arg, homoArg, His, Cit or Orn
<220> FEATURE:
<221> NAME/KEY: MOD_RES
<222> LOCATION: (19)..(19)
<223> OTHER INFORMATION: Phe, Leu, Ser, Hse, Val, Ile, Thr, or absent
<220> FEATURE:
<221> NAME/KEY: MOD_RES
<222> LOCATION: (20)..(20)
<223> OTHER INFORMATION: His, Arg, Lys, homoArg, homoLys, Asn, Gln, or
      absent
<220> FEATURE:
<221> NAME/KEY: MOD_RES
<222> LOCATION: (21)..(21)
<223> OTHER INFORMATION: Thr, Ser, Hse, Val, Ile, Leu, Gln, Asn, or
      absent
<220> FEATURE:
<221> NAME/KEY: MOD_RES
<222> LOCATION: (22)..(22)
<223> OTHER INFORMATION: Phe, Leu, Met, Val, Tyr, or Ile
<220> FEATURE:
<221> NAME/KEY: MOD_RES
<222> LOCATION: (23)..(23)
<223> OTHER INFORMATION: Pro or Hyp
<220> FEATURE:
<221> NAME/KEY: MOD_RES
<222> LOCATION: (24)..(24)
<223> OTHER INFORMATION: Pro, Hyp, Arg, Lys, homoArg, homoLys, or His
<220> FEATURE:
<221> NAME/KEY: MOD_RES
<222> LOCATION: (25)..(25)
<223> OTHER INFORMATION: Thr, Ser, Hse, Val, Ile, Leu, Phe, or Tyr
<220> FEATURE:
<221> NAME/KEY: MOD_RES
<222> LOCATION: (26)..(26)
<223> OTHER INFORMATION: Asn, Gln, Asp, or Glu
<220> FEATURE:
<221> NAME/KEY: MOD_RES
<222> LOCATION: (27)..(27)
<223> OTHER INFORMATION: Thr, Val, Ser, Phe, Ile, or Leu
<220> FEATURE:
<221> NAME/KEY: MOD_RES
<222> LOCATION: (28)..(28)
<223> OTHER INFORMATION: Gly or Ala
<220> FEATURE:
<221> NAME/KEY: MOD_RES
<222> LOCATION: (29)..(29)
<223> OTHER INFORMATION: Ser, Hse, Thr, Val, Ile, Leu, or Tyr
<220> FEATURE:
<221> NAME/KEY: MOD_RES
<222> LOCATION: (30)..(30)
<223> OTHER INFORMATION: Glu, Gly, Lys, Asn, Asp, Arg, homoArg, homoLys,
      His, or Gln
<220> FEATURE:
<221> NAME/KEY: MOD_RES
<222> LOCATION: (31)..(31)
<223> OTHER INFORMATION: Ala, Thr, Ser, Hse, Val, Ile, Leu, Phe, or Tyr
<220> FEATURE:
<221> NAME/KEY: MOD_RES
<222> LOCATION: (32)..(32)
<223> OTHER INFORMATION: Phe, Pro, Tyr, Hse, Ser, Thr, or Hyp
<220> FEATURE:
<223> OTHER INFORMATION: see specification as filed for detailed
      description of substitutions and preferred embodiments

<400> SEQUENCE: 36

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

<210> SEQ ID NO 37
<211> LENGTH: 32
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ala, Cys, Asp, Phe, Ile, Lys, Ser, Thr, or
      absent
<220> FEATURE:
<221> NAME/KEY: MOD_RES
<222> LOCATION: (2)..(2)
<223> OTHER INFORMATION: Cys, Asp, Ser, or absent
<220> FEATURE:
<221> NAME/KEY: MOD_RES
<222> LOCATION: (3)..(3)
<223> OTHER INFORMATION: Ala, Asp, Asn, or absent
<220> FEATURE:
<221> NAME/KEY: MOD_RES
<222> LOCATION: (4)..(4)
<223> OTHER INFORMATION: Ala, Leu, Thr, or absent
<220> FEATURE:
<221> NAME/KEY: MOD_RES
<222> LOCATION: (5)..(5)
<223> OTHER INFORMATION: Ala or Ser
<220> FEATURE:
<221> NAME/KEY: MOD_RES
<222> LOCATION: (6)..(6)
<223> OTHER INFORMATION: Thr, Ala, Ser, or Val
<220> FEATURE:
<221> NAME/KEY: MOD_RES
<222> LOCATION: (7)..(7)
<223> OTHER INFORMATION: Cys, Lys, or Ala
<220> FEATURE:
<221> NAME/KEY: MOD_RES
<222> LOCATION: (8)..(8)
<223> OTHER INFORMATION: Ala, Val, Leu, or Met
<220> FEATURE:
<221> NAME/KEY: MOD_RES
<222> LOCATION: (9)..(9)
<223> OTHER INFORMATION: Leu or Thr
<220> FEATURE:
<221> NAME/KEY: MOD_RES
<222> LOCATION: (10)..(10)
<223> OTHER INFORMATION: Gly, His, or Gln
<220> FEATURE:
<221> NAME/KEY: MOD_RES
<222> LOCATION: (11)..(11)
<223> OTHER INFORMATION: Lys, Arg, Gln, or homoArg
<220> FEATURE:
<221> NAME/KEY: MOD_RES
<222> LOCATION: (12)..(12)
<223> OTHER INFORMATION: Leu, Trp, or Tyr
<220> FEATURE:
<221> NAME/KEY: MOD_RES
<222> LOCATION: (13)..(13)
<223> OTHER INFORMATION: Ala, Phe, Asn, Gln, Ser, or Thr
<220> FEATURE:
<221> NAME/KEY: MOD_RES
<222> LOCATION: (14)..(14)
<223> OTHER INFORMATION: Ala, Asp, Glu, Gly, Asn, Lys, Gln, or Arg
<220> FEATURE:
<221> NAME/KEY: MOD_RES
<222> LOCATION: (15)..(15)
<223> OTHER INFORMATION: Ala, Asp, Glu, Phe, Leu, Ser, or Tyr
<220> FEATURE:
<221> NAME/KEY: MOD_RES
<222> LOCATION: (16)..(16)
<223> OTHER INFORMATION: Leu or Phe
<220> FEATURE:
<221> NAME/KEY: MOD_RES
<222> LOCATION: (17)..(17)
<223> OTHER INFORMATION: His, Gln, Ser, or Val
<220> FEATURE:
<221> NAME/KEY: MOD_RES
<222> LOCATION: (18)..(18)
<223> OTHER INFORMATION: Lys, Arg, homoArg, Cit or Orn
<220> FEATURE:
<221> NAME/KEY: MOD_RES
<222> LOCATION: (19)..(19)
<223> OTHER INFORMATION: Phe, Leu, Ser, or absent
```

```
<220> FEATURE:
<221> NAME/KEY: MOD_RES
<222> LOCATION: (20)..(20)
<223> OTHER INFORMATION: His, Gln, or absent
<220> FEATURE:
<221> NAME/KEY: MOD_RES
<222> LOCATION: (21)..(21)
<223> OTHER INFORMATION: Thr, Asn, or absent
<220> FEATURE:
<221> NAME/KEY: MOD_RES
<222> LOCATION: (22)..(22)
<223> OTHER INFORMATION: Phe, Leu, Met, Val, or Tyr
<220> FEATURE:
<221> NAME/KEY: MOD_RES
<222> LOCATION: (24)..(24)
<223> OTHER INFORMATION: Pro or Arg
<220> FEATURE:
<221> NAME/KEY: MOD_RES
<222> LOCATION: (27)..(27)
<223> OTHER INFORMATION: Thr or Val
<220> FEATURE:
<221> NAME/KEY: MOD_RES
<222> LOCATION: (30)..(30)
<223> OTHER INFORMATION: Glu, Gly, Lys, or Asn
<220> FEATURE:
<221> NAME/KEY: MOD_RES
<222> LOCATION: (31)..(31)
<223> OTHER INFORMATION: Ala or Thr
<220> FEATURE:
<221> NAME/KEY: MOD_RES
<222> LOCATION: (32)..(32)
<223> OTHER INFORMATION: Phe, Pro, or Tyr
<220> FEATURE:
<223> OTHER INFORMATION: see specification as filed for detailed
      description of substitutions and preferred embodiments

<400> SEQUENCE: 37

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Pro Xaa Thr Asn Xaa Gly Ser Xaa Xaa Xaa
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ala, Cys, Phe, Ile, Lys, Ser, or absent
<220> FEATURE:
<221> NAME/KEY: MOD_RES
<222> LOCATION: (2)..(2)
<223> OTHER INFORMATION: Cys, Asp, or Ser
<220> FEATURE:
<221> NAME/KEY: MOD_RES
<222> LOCATION: (3)..(3)
<223> OTHER INFORMATION: Ala, Asp, or Asn
<220> FEATURE:
<221> NAME/KEY: MOD_RES
<222> LOCATION: (4)..(4)
<223> OTHER INFORMATION: Ala, Leu, or Thr
<220> FEATURE:
<221> NAME/KEY: MOD_RES
<222> LOCATION: (5)..(5)
<223> OTHER INFORMATION: Ala or Ser
<220> FEATURE:
<221> NAME/KEY: MOD_RES
<222> LOCATION: (7)..(7)
<223> OTHER INFORMATION: Cys or Lys
<220> FEATURE:
<221> NAME/KEY: MOD_RES
<222> LOCATION: (8)..(8)
<223> OTHER INFORMATION: Ala or Val
```

```
<220> FEATURE:
<221> NAME/KEY: MOD_RES
<222> LOCATION: (9)..(9)
<223> OTHER INFORMATION: Leu or Thr
<220> FEATURE:
<221> NAME/KEY: MOD_RES
<222> LOCATION: (10)..(10)
<223> OTHER INFORMATION: Gly, His, or Gln
<220> FEATURE:
<221> NAME/KEY: MOD_RES
<222> LOCATION: (11)..(11)
<223> OTHER INFORMATION: Lys, Arg, or homoArg
<220> FEATURE:
<221> NAME/KEY: MOD_RES
<222> LOCATION: (13)..(13)
<223> OTHER INFORMATION: Ala, Phe, Asn, Ser, or Thr
<220> FEATURE:
<221> NAME/KEY: MOD_RES
<222> LOCATION: (14)..(14)
<223> OTHER INFORMATION: Ala, Asp, Glu, Gly, Asn, Gln, or Arg
<220> FEATURE:
<221> NAME/KEY: MOD_RES
<222> LOCATION: (15)..(15)
<223> OTHER INFORMATION: Ala, Glu, Phe, Leu, Ser, or Tyr
<220> FEATURE:
<221> NAME/KEY: MOD_RES
<222> LOCATION: (17)..(17)
<223> OTHER INFORMATION: His, Ser, or Val
<220> FEATURE:
<221> NAME/KEY: MOD_RES
<222> LOCATION: (18)..(18)
<223> OTHER INFORMATION: Lys, Arg, homoArg, Cit or Orn
<220> FEATURE:
<221> NAME/KEY: MOD_RES
<222> LOCATION: (19)..(19)
<223> OTHER INFORMATION: Phe, Leu, or Ser
<220> FEATURE:
<221> NAME/KEY: MOD_RES
<222> LOCATION: (20)..(20)
<223> OTHER INFORMATION: His or Gln
<220> FEATURE:
<221> NAME/KEY: MOD_RES
<222> LOCATION: (21)..(21)
<223> OTHER INFORMATION: Thr or Asn
<220> FEATURE:
<221> NAME/KEY: MOD_RES
<222> LOCATION: (22)..(22)
<223> OTHER INFORMATION: Phe, Leu, Met, Val, or Tyr
<220> FEATURE:
<221> NAME/KEY: MOD_RES
<222> LOCATION: (24)..(24)
<223> OTHER INFORMATION: Pro or Arg
<220> FEATURE:
<221> NAME/KEY: MOD_RES
<222> LOCATION: (27)..(27)
<223> OTHER INFORMATION: Thr or Val
<220> FEATURE:
<221> NAME/KEY: MOD_RES
<222> LOCATION: (30)..(30)
<223> OTHER INFORMATION: Glu, Gly, Lys, or Asn
<220> FEATURE:
<221> NAME/KEY: MOD_RES
<222> LOCATION: (31)..(31)
<223> OTHER INFORMATION: Ala or Thr
<220> FEATURE:
<221> NAME/KEY: MOD_RES
<222> LOCATION: (32)..(32)
<223> OTHER INFORMATION: Phe, Pro, or Tyr
<220> FEATURE:
<223> OTHER INFORMATION: see specification as filed for detailed
      description of substitutions and preferred embodiments

<400> SEQUENCE: 38

Xaa Xaa Xaa Xaa Xaa Thr Xaa Xaa Xaa Xaa Xaa Leu Xaa Xaa Xaa Leu
1               5                   10                  15

Xaa Xaa Xaa Xaa Xaa Xaa Pro Xaa Thr Asn Xaa Gly Ser Xaa Xaa Xaa
            20                  25                  30
```

```
<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Gln Thr Tyr
1

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ala, Cys, Asp, Phe, Lys, Thr, or absent
<220> FEATURE:
<221> NAME/KEY: MOD_RES
<222> LOCATION: (2)..(2)
<223> OTHER INFORMATION: Ala, Cys, Asp, Ser, or absent
<220> FEATURE:
<221> NAME/KEY: MOD_RES
<222> LOCATION: (3)..(3)
<223> OTHER INFORMATION: Ala, Asp, Asn, or absent
<220> FEATURE:
<221> NAME/KEY: MOD_RES
<222> LOCATION: (4)..(4)
<223> OTHER INFORMATION: Ala, Leu, Thr, or absent
<220> FEATURE:
<221> NAME/KEY: MOD_RES
<222> LOCATION: (5)..(5)
<223> OTHER INFORMATION: Ala or Ser
<220> FEATURE:
<221> NAME/KEY: MOD_RES
<222> LOCATION: (6)..(6)
<223> OTHER INFORMATION: Ala, Ser, Thr, or Val
<220> FEATURE:
<221> NAME/KEY: MOD_RES
<222> LOCATION: (7)..(7)
<223> OTHER INFORMATION: Ala, Cys, or Lys
<220> FEATURE:
<221> NAME/KEY: MOD_RES
<222> LOCATION: (8)..(8)
<223> OTHER INFORMATION: Ala, Leu, Met, or Val
<220> FEATURE:
<221> NAME/KEY: MOD_RES
<222> LOCATION: (9)..(9)
<223> OTHER INFORMATION: Leu or Thr
<220> FEATURE:
<221> NAME/KEY: MOD_RES
<222> LOCATION: (10)..(10)
<223> OTHER INFORMATION: Gly, His, or Gln
<220> FEATURE:
<221> NAME/KEY: MOD_RES
<222> LOCATION: (11)..(11)
<223> OTHER INFORMATION: Lys, Gln, or Arg
<220> FEATURE:
<221> NAME/KEY: MOD_RES
<222> LOCATION: (12)..(12)
<223> OTHER INFORMATION: Leu, Trp, or Tyr
<220> FEATURE:
<221> NAME/KEY: MOD_RES
<222> LOCATION: (13)..(13)
<223> OTHER INFORMATION: Ala, Asn, Gln, Ser, or Thr
<220> FEATURE:
<221> NAME/KEY: MOD_RES
<222> LOCATION: (14)..(14)
<223> OTHER INFORMATION: Ala, Asp, Glu, Gly, Lys, Asn, Gln, or Arg
<220> FEATURE:
<221> NAME/KEY: MOD_RES
```

```
<222> LOCATION: (15)..(15)
<223> OTHER INFORMATION: Ala, Asp, Glu, Phe, Leu, Ser, or Tyr
<220> FEATURE:
<221> NAME/KEY: MOD_RES
<222> LOCATION: (16)..(16)
<223> OTHER INFORMATION: Phe or Leu
<220> FEATURE:
<221> NAME/KEY: MOD_RES
<222> LOCATION: (17)..(17)
<223> OTHER INFORMATION: His, Gln, Ser or Val
<220> FEATURE:
<221> NAME/KEY: MOD_RES
<222> LOCATION: (18)..(18)
<223> OTHER INFORMATION: Lys or Arg
<220> FEATURE:
<221> NAME/KEY: MOD_RES
<222> LOCATION: (19)..(19)
<223> OTHER INFORMATION: Phe, Leu, Ser, or absent
<220> FEATURE:
<221> NAME/KEY: MOD_RES
<222> LOCATION: (20)..(20)
<223> OTHER INFORMATION: His, Lys, Gln, or absent
<220> FEATURE:
<221> NAME/KEY: MOD_RES
<222> LOCATION: (21)..(21)
<223> OTHER INFORMATION: Gln, Thr, or absent
<220> FEATURE:
<221> NAME/KEY: MOD_RES
<222> LOCATION: (22)..(22)
<223> OTHER INFORMATION: Phe, Leu, or Tyr
<220> FEATURE:
<221> NAME/KEY: MOD_RES
<222> LOCATION: (24)..(24)
<223> OTHER INFORMATION: Pro or Arg
<220> FEATURE:
<221> NAME/KEY: MOD_RES
<222> LOCATION: (27)..(27)
<223> OTHER INFORMATION: Thr or Val
<220> FEATURE:
<221> NAME/KEY: MOD_RES
<222> LOCATION: (30)..(30)
<223> OTHER INFORMATION: Glu, Lys, or Asn
<220> FEATURE:
<221> NAME/KEY: MOD_RES
<222> LOCATION: (31)..(31)
<223> OTHER INFORMATION: Ala or Thr
<220> FEATURE:
<221> NAME/KEY: MOD_RES
<222> LOCATION: (32)..(32)
<223> OTHER INFORMATION: Phe, Tyr, or absent
<220> FEATURE:
<223> OTHER INFORMATION: see specification as filed for detailed
      description of substitutions and preferred embodiments

<400> SEQUENCE: 40

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Pro Xaa Thr Asn Xaa Gly Ser Xaa Xaa Xaa
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Lys Cys Asn Thr Ala Thr Cys Val Leu Gly Lys Leu Ser Gln Glu Leu
1               5                   10                  15

His Arg Leu Gln Thr Tyr Pro Arg Thr Asn Thr Gly Ser Asn Thr Tyr
            20                  25                  30
```

<210> SEQ ID NO 42
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Lys Cys Asn Thr Ala Thr Cys Val Leu Gly Arg Leu Ser Gln Glu Leu
1               5                   10                  15

His Arg Leu Gln Thr Leu Pro Arg Thr Asn Thr Gly Ser Asn Thr Tyr
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Lys Cys Asn Thr Ala Thr Cys Val Leu Gly Arg Leu Ser Gln Glu Leu
1               5                   10                  15

His Arg Leu Gln Thr Tyr Pro Pro Thr Asn Thr Gly Ser Asn Thr Tyr
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Lys Cys Asn Thr Ala Thr Cys Val Leu Gly Arg Leu Ser Gln Glu Leu
1               5                   10                  15

His Arg Leu Gln Thr Tyr Pro Arg Thr Asn Val Gly Ser Asn Thr Tyr
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Lys Cys Asn Thr Ala Thr Cys Val Leu Gly Arg Leu Ser Gln Glu Leu
1               5                   10                  15

His Arg Leu Gln Thr Leu Pro Pro Thr Asn Val Gly Ser Asn Thr Tyr
            20                  25                  30

<210> SEQ ID NO 46
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Lys Cys Asn Thr Ala Thr Cys Val Leu Gly Arg Leu Ala Asn Phe Leu
1               5                   10                  15

His Arg Leu Gln Thr Tyr Pro Arg Thr Asn Thr Gly Ser Asn Thr Tyr
            20                  25                  30

<210> SEQ ID NO 47
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ala Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Lys Cys Asn Ala Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Lys Cys Asn Thr Ala Ala Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Cys Ala Asn Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (1)..(1)
<223> OTHER INFORMATION: Isocaproyl-Ser

<400> SEQUENCE: 51

Xaa Thr Ala Val Leu Gly Arg Leu Ser Gln Glu Leu His Arg Leu Gln
1               5                   10                  15

Thr Tyr Pro Arg Thr Asn Thr Gly Ser Asn Thr Tyr
            20                  25

<210> SEQ ID NO 52
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Cys Ser Asn Ala Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Cys Ser Asn Leu Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 54
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Cys Ser Asn Leu Ser Ala Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Lys Cys Asn Thr Ala Thr Cys Val Leu Gly Arg Leu Ser Gln Glu Leu
1               5                   10                  15

His Lys Leu Gln Thr Tyr Pro Arg Thr Asn Thr Gly Ser Asn Thr Tyr
            20                  25                  30
```

```
<210> SEQ ID NO 56
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Gly Thr Pro
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Cys Ser Ala Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Agy
<220> FEATURE:
<221> NAME/KEY: MOD_RES
<222> LOCATION: (7)..(7)
<223> OTHER INFORMATION: Agy

<400> SEQUENCE: 58

Xaa Ser Asn Leu Ser Thr Xaa Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 59
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (2)..(2)
<223> OTHER INFORMATION: Agy
<220> FEATURE:
<221> NAME/KEY: MOD_RES
<222> LOCATION: (7)..(7)
<223> OTHER INFORMATION: Agy
```

<400> SEQUENCE: 59

Lys Xaa Asn Thr Ala Thr Xaa Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 60
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Isocaproyl-Ser
<220> FEATURE:
<221> NAME/KEY: MOD_RES
<222> LOCATION: (6)..(6)
<223> OTHER INFORMATION: Aib

<400> SEQUENCE: 60

Xaa Thr Ala Val Leu Xaa Arg Leu Ser Gln Glu Leu Arg Leu Gln Thr
1               5                   10                  15

Tyr Pro Arg Thr Asn Thr Gly Ser Gly Thr Pro
            20                  25

<210> SEQ ID NO 61
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Isocaproyl-Ser
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (14)..(14)
<223> OTHER INFORMATION: Lys(For)

<400> SEQUENCE: 61

Xaa Thr Ala Val Leu Gly Xaa Leu Ser Gln Glu Leu His Xaa Leu Gln
1               5                   10                  15

Thr Tyr Pro Arg Thr Asn Thr Gly Ser Gly Thr Pro
            20                  25

<210> SEQ ID NO 62
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Isocaproyl-Ser
<220> FEATURE:
<221> NAME/KEY: MOD_RES
<222> LOCATION: (6)..(6)
<223> OTHER INFORMATION: Aib
<220> FEATURE:

```
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(For)

<400> SEQUENCE: 62

Xaa Thr Ala Val Leu Xaa Xaa Leu Ser Gln Glu Leu Xaa Xaa Leu Gln
1               5                   10                  15

Thr Tyr Pro Arg Thr Asn Thr Gly Ser Asn Thr Tyr
            20                  25

<210> SEQ ID NO 63
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Isocaproyl-Ser
<220> FEATURE:
<221> NAME/KEY: MOD_RES
<222> LOCATION: (6)..(6)
<223> OTHER INFORMATION: Aib
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(For)

<400> SEQUENCE: 63

Xaa Thr Ala Val Leu Xaa Xaa Leu Ser Gln Glu Leu Xaa Xaa Leu Gln
1               5                   10                  15

Thr Tyr Pro Arg Thr Asn Val Gly Ser Asn Thr Tyr
            20                  25

<210> SEQ ID NO 64
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Lys Cys Asn Thr Ala Thr Cys Leu Leu Gln Gln Leu Gln Lys Leu Leu
1               5                   10                  15

Gln Lys Leu Lys Gln Tyr Pro Arg Thr Asn Thr Gly Ser Asn Thr Tyr
            20                  25                  30

<210> SEQ ID NO 65
<211> LENGTH: 32
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 65

Lys Cys Asn Thr Ala Ser Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 66
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Lys Cys Asn Thr Ala Val Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 67
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Lys Cys Asn Thr Ala Thr Cys Val Leu Gly Arg Leu Ser Gln Glu Leu
1               5                   10                  15

His Arg Tyr Pro Arg Thr Asn Thr Gly Ser Asn Thr Tyr
            20                  25

<210> SEQ ID NO 68
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Lys(For)
<220> FEATURE:
<221> NAME/KEY: MOD_RES
<222> LOCATION: (18)..(18)
<223> OTHER INFORMATION: Lys(For)

<400> SEQUENCE: 68

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 69
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (6)..(6)
<223> OTHER INFORMATION: D-Thr

<400> SEQUENCE: 69

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 70
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: dAh

<400> SEQUENCE: 70

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term acetylated
<220> FEATURE:
<221> NAME/KEY: MOD_RES
<222> LOCATION: (18)..(18)
<223> OTHER INFORMATION: Lys(PEG5000)

<400> SEQUENCE: 71

Ala Cys Asn Thr Ala Thr Cys Val Leu Gly Arg Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 72
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Lys Cys Asn Thr Ala Thr Cys Val Leu Gly Arg Leu Ser Gln Glu Leu
1               5                   10                  15

His Arg Leu Gln Thr Leu Gln Thr Tyr Pro Arg Thr Asn Thr Gly Ser
            20                  25                  30

Asn Thr Tyr
        35

<210> SEQ ID NO 73
<211> LENGTH: 36
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 73

Lys Cys Asn Thr Ala Thr Cys Val Leu Gly Arg Leu Ser Gln Glu Leu
1               5                   10                  15

His Arg Leu Gln Thr Leu Leu Gln Thr Tyr Pro Arg Thr Asn Thr Gly
            20                  25                  30

Ser Asn Thr Tyr
            35

<210> SEQ ID NO 74
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Lys Cys Asn Thr Ala Thr Cys Val Leu Gly Lys Leu Ser Gln Glu Leu
1               5                   10                  15

His Lys Leu Gln Thr Tyr Pro Arg Thr Asn Thr Gly Ser Asn Thr Tyr
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Lys Cys Asn Thr Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 76
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Lys Cys Asn Thr Ala Thr Cys Ala Thr Gln Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 77
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Lys Cys Asn Thr Ala Thr Cys Ala Thr Gln Arg Leu Ser Gln Glu Leu
1               5                   10                  15
```

His Arg Leu Gln Thr Tyr Pro Arg Thr Asn Val Gly Ser Asn Thr Tyr
            20                  25                  30

<210> SEQ ID NO 78
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Lys Cys Asn Thr Ser Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 79
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Hse

<400> SEQUENCE: 79

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 80
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Ahb

<400> SEQUENCE: 80

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 81
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Ahp

<400> SEQUENCE: 81

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 82
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Thr(OPO3H2)

<400> SEQUENCE: 82

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 83
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Orn
<220> FEATURE:
<221> NAME/KEY: MOD_RES
<222> LOCATION: (18)..(18)
<223> OTHER INFORMATION: Orn

<400> SEQUENCE: 83

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 84
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Cit
<220> FEATURE:
<221> NAME/KEY: MOD_RES
<222> LOCATION: (18)..(18)
<223> OTHER INFORMATION: Cit

<400> SEQUENCE: 84

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 85
<211> LENGTH: 32
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: homoK
<220> FEATURE:
<221> NAME/KEY: MOD_RES
<222> LOCATION: (18)..(18)
<223> OTHER INFORMATION: homoK

<400> SEQUENCE: 85

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 86
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: L-Octylglycine

<400> SEQUENCE: 86

Xaa Lys Cys Asn Thr Ala Thr Cys Val Leu Gly Arg Leu Ser Gln Glu
1               5                   10                  15

Leu His Arg Leu Gln Thr Tyr Pro Arg Thr Asn Thr Gly Ser Asn Thr
            20                  25                  30

Tyr

<210> SEQ ID NO 87
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: N-3,6-dioxaoctanoyl-Cys

<400> SEQUENCE: 87

Xaa Asn Thr Ala Thr Cys Val Leu Gly Arg Leu Ser Gln Glu Leu His
1               5                   10                  15

Arg Leu Gln Thr Val Pro Arg Thr Asn Thr Gly Ser Asn Thr Tyr
            20                  25                  30

<210> SEQ ID NO 88
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Lys Cys Asn Thr Ala Thr Cys Met Leu Gly Arg Tyr Thr Gln Asp Phe
1               5                   10                  15

His Arg Leu Gln Thr Tyr Pro Arg Thr Asn Thr Gly Ser Asn Thr Tyr
            20                  25                  30
```

<210> SEQ ID NO 89
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Ser Asn Leu Ser Thr Lys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 90
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Lys Asp Asn Thr Ala Thr Lys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 91
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Cys Asn Thr Ala Thr Cys Val Leu Gly Arg Leu Ser Gln Glu Leu His
1               5                   10                  15

Arg Leu Gln Thr Tyr Pro Arg Thr Asn Thr Gly Ser Asn Thr Tyr
            20                  25                  30

<210> SEQ ID NO 92
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: 9Anc

<400> SEQUENCE: 92

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa

<210> SEQ ID NO 93
<211> LENGTH: 33
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: L-octylglycine

<400> SEQUENCE: 93

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa

<210> SEQ ID NO 94
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: N-isocaproyl-Lys

<400> SEQUENCE: 94

Xaa Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 95
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: homoR
<220> FEATURE:
<221> NAME/KEY: MOD_RES
<222> LOCATION: (18)..(18)
<223> OTHER INFORMATION: homoR

<400> SEQUENCE: 95

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 96
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Phe Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

-continued

```
<210> SEQ ID NO 97
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: Cit

<400> SEQUENCE: 97

Lys Cys Asn Thr Ala Thr Cys Val Leu Gly Arg Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 98
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: Orn

<400> SEQUENCE: 98

Lys Cys Asn Thr Ala Thr Cys Val Leu Gly Arg Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 99
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Ile Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 100
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 1-Octylglycine

<400> SEQUENCE: 100

Xaa Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

```
<210> SEQ ID NO 101
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Isocaproyl-Cys

<400> SEQUENCE: 101

Xaa Asn Thr Ala Thr Cys Val Leu Gly Arg Leu Ser Gln Glu Leu His
1               5                   10                  15

Arg Leu Gln Thr Tyr Pro Arg Thr Asn Thr Gly Ser Asn Thr Tyr
            20                  25                  30

<210> SEQ ID NO 102
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Cit

<400> SEQUENCE: 102

Lys Cys Asn Thr Ala Thr Cys Val Leu Gly Xaa Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 103
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: 4ABU

<400> SEQUENCE: 103

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa

<210> SEQ ID NO 104
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Isocaproyl-Lys
<220> FEATURE:
<221> NAME/KEY: MOD_RES
<222> LOCATION: (33)..(33)
```

<223> OTHER INFORMATION: 4ABU

<400> SEQUENCE: 104

Xaa Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa

<210> SEQ ID NO 105
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Lys Cys Asn Thr Ser Thr Cys Ala Thr Gln Arg Leu Ala Asn Glu Leu
1               5                   10                  15

Val Arg Leu Gln Thr Tyr Pro Arg Thr Asn Val Gly Ser Glu Ala Phe
            20                  25                  30

<210> SEQ ID NO 106
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Lys Cys Asn Thr Ala Thr Cys Val Leu Gly Arg Leu Ser Gln Glu Leu
1               5                   10                  15

His Arg Leu Gln Thr Tyr Pro Thr Asn Val Gly Ser Glu Ala Phe
            20                  25                  30

<210> SEQ ID NO 107
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Lys Cys Asn Thr Ala Thr Cys Val Leu Gly Arg Leu Ser Arg Ser Leu
1               5                   10                  15

His Arg Leu Gln Thr Tyr Pro Arg Thr Asn Thr Gly Ser Asn Thr Tyr
            20                  25                  30

<210> SEQ ID NO 108
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Lys Cys Asn Thr Ala Thr Cys Val Thr His Arg Leu Ser Gln Glu Leu
1               5                   10                  15

His Arg Leu Gln Thr Tyr Pro Arg Thr Asn Thr Gly Ser Asn Thr Tyr
            20                  25                  30

```
<210> SEQ ID NO 109
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Lys Cys Asn Thr Ala Thr Cys Val Leu Gly Arg Leu Ala Asp Phe Leu
1               5                   10                  15

His Arg Leu Gln Thr Tyr Pro Arg Thr Asn Thr Gly Ser Asn Thr Tyr
            20                  25                  30

<210> SEQ ID NO 110
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Cys Asn Thr Ala Thr Cys Val Leu Gly Arg Leu Ser Gln Glu Leu His
1               5                   10                  15

Arg Leu Gln Thr Tyr Pro Arg Thr Asn Thr Gly Ser Asn Thr
            20                  25                  30

<210> SEQ ID NO 111
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Lys Cys Asn Thr Ala Thr Cys Val Leu Gly Arg Leu Ser Gln Glu Leu
1               5                   10                  15

His Arg Leu Gln Asn Phe Val Pro Arg Thr Asn Thr Gly Ser Asn Thr
            20                  25                  30

Tyr

<210> SEQ ID NO 112
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Glu Thr Phe
            20                  25                  30

<210> SEQ ID NO 113
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113
```

```
Ala Cys Asp Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

<210> SEQ ID NO 114
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

```
Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Lys Ala Phe
            20                  25                  30
```

<210> SEQ ID NO 115
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

```
Lys Cys Asp Thr Ala Thr Cys Val Thr His Arg Leu Ala Gly Leu Leu
1               5                   10                  15

Ser Arg Ser Gln Thr Tyr Pro Arg Thr Asn Thr Gly Ser Asn Thr Tyr
            20                  25                  30
```

<210> SEQ ID NO 116
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Lys Cys Asn Thr Ala Thr Cys Val Leu Gly Arg Leu Ala Asp Ala Leu
1               5                   10                  15

His Arg Leu Gln Thr Tyr Pro Arg Thr Asn Thr Gly Ser Asn Thr Tyr
            20                  25                  30
```

<210> SEQ ID NO 117
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Lys Cys Asn Thr Ala Thr Cys Val Leu Gly Arg Leu Ala Ala Phe Leu
1               5                   10                  15

His Arg Leu Gln Thr Tyr Pro Arg Thr Asn Thr Gly Ser Asn Thr Tyr
            20                  25                  30
```

<210> SEQ ID NO 118
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 118

Ser Cys Asn Thr Ala Thr Cys Val Leu Gly Arg Leu Ala Asp Phe Leu
1               5                   10                  15

His Arg Leu Gln Thr Tyr Pro Arg Thr Asn Thr Gly Ser Asn Thr Tyr
            20                  25                  30

<210> SEQ ID NO 119
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Lys Cys Asn Thr Ala Thr Cys Val Leu Gly Arg Leu Ser Gln Glu Leu
1               5                   10                  15

His Arg Leu Gln Thr Met Pro Arg Thr Asn Thr Gly Ser Asn Thr Tyr
            20                  25                  30

<210> SEQ ID NO 120
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Lys Cys Asn Thr Ala Thr Cys Val Leu Gly Arg Leu Ser Gln Glu Leu
1               5                   10                  15

His Arg Leu Gln Thr Val Pro Arg Thr Asn Thr Gly Ser Asn Thr Tyr
            20                  25                  30

<210> SEQ ID NO 121
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Lys Cys Asn Thr Ala Thr Cys Val Leu Gly Arg Leu Asn Glu Tyr Leu
1               5                   10                  15

His Arg Leu Gln Thr Tyr Pro Arg Thr Asn Thr Gly Ser Asn Thr Tyr
            20                  25                  30

<210> SEQ ID NO 122
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ser Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

<210> SEQ ID NO 123
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Lys Cys Asn Thr Ala Thr Cys Val Leu Gly Arg Leu Thr Glu Phe Leu
1               5                   10                  15

His Arg Leu Gln Thr Tyr Pro Arg Thr Asn Thr Gly Ser Asn Thr Tyr
            20                  25                  30

<210> SEQ ID NO 124
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Lys Cys Asn Thr Ala Thr Cys Val Leu Gly Arg Leu Ala Glu Phe Leu
1               5                   10                  15

His Arg Leu Gln Thr Tyr Pro Arg Thr Asn Thr Gly Ser Asn Thr Tyr
            20                  25                  30

<210> SEQ ID NO 125
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Lys Cys Asn Thr Ala Thr Cys Val Leu Gly Arg Leu Thr Asp Tyr Leu
1               5                   10                  15

His Arg Leu Gln Thr Tyr Pro Arg Thr Asn Thr Gly Ser Asn Thr Tyr
            20                  25                  30

<210> SEQ ID NO 126
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Lys Cys Asn Thr Ala Thr Cys Val Leu Gly Arg Leu Ala Gln Phe Leu
1               5                   10                  15

His Arg Leu Gln Thr Tyr Pro Arg Thr Asn Thr Gly Ser Asn Thr Tyr
            20                  25                  30

<210> SEQ ID NO 127
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Lys Cys Asn Thr Ala Thr Cys Val Leu Gly Arg Leu Ala Asp Phe Leu

```
1               5                   10                  15
His Arg Phe Gln Thr Phe Pro Arg Thr Asn Thr Gly Ser Asn Thr Tyr
            20                  25                  30

<210> SEQ ID NO 128
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Lys Cys Asn Thr Ala Thr Cys Val Leu Gly Arg Leu Ala Asp Phe Leu
1               5                   10                  15

His Arg Phe His Thr Phe Pro Arg Thr Asn Thr Gly Ser Asn Thr Tyr
            20                  25                  30

<210> SEQ ID NO 129
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Lys Cys Asn Thr Ala Thr Cys Val Leu Gly Arg Leu Ala Asp Phe Leu
1               5                   10                  15

His Arg Phe Gln Thr Phe Pro Arg Thr Asn Thr Gly Ser Gly Thr Pro
            20                  25                  30

<210> SEQ ID NO 130
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Cys Asn Thr Ala Thr Cys Val Leu Gly Arg Leu Ala Asp Phe Leu His
1               5                   10                  15

Arg Leu Gln Thr Tyr Pro Arg Thr Asn Thr Gly Ser Asn Thr Tyr
            20                  25                  30

<210> SEQ ID NO 131
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Lys Cys Asp Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 132
<211> LENGTH: 32
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 132

Lys Cys Asn Thr Ala Thr Cys Val Leu Gly Arg Leu Phe Asp Phe Leu
1               5                   10                  15

His Arg Leu Gln Thr Tyr Pro Arg Thr Asn Thr Gly Ser Asn Thr Tyr
            20                  25                  30

<210> SEQ ID NO 133
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Lys Cys Asn Thr Ala Thr Cys Val Leu Gly Arg Leu Ala Ala Ala Leu
1               5                   10                  15

His Arg Leu Gln Thr Tyr Pro Arg Thr Asn Thr Gly Ser Asn Thr Tyr
            20                  25                  30

<210> SEQ ID NO 134
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Thr Cys Asp Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 135
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Cys Ser Asn Leu Ser Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 136
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Lys Cys Asn Thr Ala Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 137

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Cys Ser Asn Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 138
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (2)..(7)
<223> OTHER INFORMATION: Cyclic

<400> SEQUENCE: 138

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 139
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Lys Cys Asn Thr Ala Thr Cys Ala Thr Gln Arg Leu Ala Asn Phe Leu
1               5                   10                  15

Val Arg Ser Ser Asn Asn Leu Thr Asn Val Gly Ser Asn Thr Tyr
            20                  25                  30

<210> SEQ ID NO 140
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Lys Cys Asn Thr Ala Thr Cys Ala Thr Gln Arg Leu Ala Asn Ala Leu
1               5                   10                  15

Val His Ser Ser Asn Asn Phe Gly Ala Ile Leu Pro Ser Thr Asn Val
            20                  25                  30

Gly Ser Asn Thr Tyr
        35

<210> SEQ ID NO 141
<211> LENGTH: 22
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 141

Lys Cys Asn Thr Ala Thr Cys Ala Thr Ala Arg Leu Ala Ala Phe Leu
1               5                   10                  15

Ala Arg Ser Ser Gly Tyr
            20

<210> SEQ ID NO 142
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Lys Cys Asn Thr Ala Thr Cys Ala Thr Gln Arg Leu Ala Asn Phe Leu
1               5                   10                  15

Val His Ser Gly Asn Asn Phe Gly Ala Ile Leu Ser Ser Thr Asn Val
            20                  25                  30

Gly Ser Asn Thr Tyr
        35

<210> SEQ ID NO 143
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Cys Asn Thr Ala Thr Cys Ala Thr Ala Arg Leu Ala Ala Phe Leu Ala
1               5                   10                  15

Arg Ser

<210> SEQ ID NO 144
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Lys Cys Ala Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 145
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Lys Cys Asn Thr Ala Thr Cys Ala Thr Gln Arg Leu Ser Gln Glu Leu
1               5                   10                  15

His Arg Leu Gln Thr Tyr Pro Arg Thr Asn Thr Gly Ser Gly Thr Pro
            20                  25                  30